United States Patent
Stafford et al.

(10) Patent No.: US 11,014,983 B2
(45) Date of Patent: May 25, 2021

(54) ANTI-TIM-3 ANTIBODIES, COMPOSITIONS COMPRISING ANTI-TIM-3 ANTIBODIES AND METHODS OF MAKING AND USING ANTI-TIM-3 ANTIBODIES

(71) Applicant: SUTRO BIOPHARMA, INC., South San Francisco, CA (US)

(72) Inventors: Ryan Stafford, Emeryville, CA (US); Alice Yam, Tiburon, CA (US); John Lee, San Francisco, CA (US); Junhao Yang, Foster City, CA (US); Aaron Sato, Burlingame, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 481 days.

(21) Appl. No.: 15/752,873

(22) PCT Filed: Aug. 17, 2016

(86) PCT No.: PCT/US2016/047417
§ 371 (c)(1),
(2) Date: Feb. 14, 2018

(87) PCT Pub. No.: WO2017/031242
PCT Pub. Date: Feb. 23, 2017

(65) Prior Publication Data
US 2018/0251547 A1  Sep. 6, 2018

Related U.S. Application Data

(60) Provisional application No. 62/207,845, filed on Aug. 20, 2015.

(51) Int. Cl.
| | | |
|---|---|---|
| *C07K 16/00* | (2006.01) | |
| *C07K 16/28* | (2006.01) | |
| *A61P 35/00* | (2006.01) | |
| *A61K 39/395* | (2006.01) | |

(52) U.S. Cl.
CPC .... *C07K 16/2803* (2013.01); *A61K 39/39541* (2013.01); *A61P 35/00* (2018.01); *C07K 2317/21* (2013.01); *C07K 2317/24* (2013.01); *C07K 2317/55* (2013.01); *C07K 2317/565* (2013.01); *C07K 2317/622* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2015/0218274 A1 | 8/2015 | Sabatos-Peyton et al. |
| 2017/0121409 A1 | 5/2017 | Verona et al. |

FOREIGN PATENT DOCUMENTS

| | | |
|---|---|---|
| EP | 2 417 984 A1 | 2/2012 |
| EP | 2 581 113 A1 | 4/2013 |
| WO | WO 2004/056875 A1 | 7/2004 |
| WO | WO 2010/084999 A1 | 7/2010 |
| WO | WO 2011/159877 A2 | 12/2011 |
| WO | WO 2013/006490 A2 | 1/2013 |
| WO | WO 2013/166604 A1 | 11/2013 |
| WO | WO 2014/179664 A2 | 11/2014 |
| WO | WO 2015/048312 A1 | 4/2015 |
| WO | WO 2015/095418 A1 | 6/2015 |
| WO | WO 2015/117002 A1 | 8/2015 |
| WO | WO 2016/068803 A1 | 5/2016 |
| WO | WO 2016/077397 A2 | 5/2016 |
| WO | WO 2016/153572 A1 | 9/2016 |
| WO | WO 2016/179194 A1 | 11/2016 |
| WO | WO 2017/011580 A2 | 1/2017 |
| WO | WO 2017/031242 A1 | 2/2017 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Lee et al., "High-affinity Human Antibodies from Phage-displayed Synthetic Fab Libraries with a Single Framework Scaffold", Journal of Molecular Bio, Academic Press, United Kingdom, vol. 340, No. 5, Jul. 23, 2004, pp. 1073-1093.
Ponsel et al., "High affinity, developability and functional size: the holy grail of combinatorial antibody library generation", Molecules: A Journal of Synthetic Organic and Natural Product Chemi, vol. 16, No. 5, Jan. 1, 2011, pp. 3675-3700.
International Search Report and Written Opinion of PCT/US2016/047417 dated Nov. 18, 2016; 17 pages.

* cited by examiner

*Primary Examiner* — Meera Natarajan
(74) *Attorney, Agent, or Firm* — Squire Patton Boggs (US) LLP

(57) ABSTRACT

Provided herein are antibodies that selectively bind to Tim-3 and its isoforms and homologs, and compositions comprising the antibodies. Also provided are methods of using the antibodies, such as therapeutic and diagnostic methods.

27 Claims, 5 Drawing Sheets

Specification includes a Sequence Listing.

Hybridoma Variable Domains

Hybridoma Antibodies - VHs

```
h22E11-VH5-51-VH    EVQLVQSGAEVKKPGESLKISCKVSGFSLTSYGVHWVRQMPGKGLEWLVVIWS-DGSTTY
h22E11-VH1-69-VH    QVQLVQSGAEVKKPGSSVKVSCKVSGFSLTSYGVHWVRQAPGQGLEWLVVIWS-DGSTTY
22E11-VH            QVQLKESGPDLVAPSQSLSITCTVSGFSLTSYGVHWVRQPPGKGLEWLVVIWS-DGSTTY
h22E11-VH4-30-4-VH  QVQLQESGPGLIVKPSQTLSLTCTVSGFSLTSYGVHWIRQPPGKGLEWLVVIWS-DGSTTY
h22E11-VH3-23-VH    EVQLLESGGGLVQPGGSLRLSCAVSGFSLTSYGVHWVRQAPGKGLEWLVVIWS-DGSTTY
h22E11-VH3-5-VH     EVQLVESGGGLVQPGGSLRLSCAVSGFSLTSYGVHWVRQAPGKGLEWLVVIWS-DGSTTY
2D5-VH              EVQLQQSGPELVKPGTSMKISCRASGYPFIGYTMNWVKQSHGGNLEWIGLINPYNGITTY
                    : :* :*** :  :      * *:      *    * :   * :*  *  :   ** * h22E11-VH5-51-VH    NPSFQGQVTISKDKSISTVYLQWSSLKASDTAMYYCARQGGYR-YDDAMDYWGQGTLVTVSS
h22E11-VH1-69-VH    NQKFQGRVTITKDESTSTVYMELSSLRSEDTAVYYCARQGGYR-YDDAMDYWGQGTLVTVSS
22E11-VH            NSALKSRLTIISKDNSKSQVFLKMNSLQTDDTAMYYCARQGGYR-YDDAMDYWGQGTSVAVSS
h22E11-VH4-30-4-VH  NPSLKSRVTISKDTSKNQVSLKLSSVTAADTAVYYCARQGGYR-YDDAMDYWGQGTLVTVSS
h22E11-VH3-23-VH    NDSVKGRFTISKDNSKNTVYLQMNSLRAEDTAVYYCARQGGYR-YDDAMDYWGQGTLVTVSS
h22E11-VH3-5-VH     NSALKSRFTISKDNAKNSVYLQMNSLRAEDTAVYYCARQGGYR-YDDAMDYWGQGTLVTVSS
2D5-VH              NQKFKGRATLSVDTSSTIAYMELLSLTSDDSAEYYCARSFFYGSSNDWLVYWGQGTLVTVSA
                    *  : .: ::: .: .:  :  .*:: *:: :***   : :.  . ****** ****:
```

FIG. 2A

Hybridoma Antibodies - VLs

```
h22E11-Vk3-11-VL    EIVLTQSPATLSLSPGERATLSCKASQSVDYD-GNSYVNWYQQKPGQAPRLLIYAASNLE
h22E11-5-VL         EIVLTQSPGTLSLSPGERATLSCKASQSVDYD-GNSYVAWYQQKPGQAPRLLIYAASNLE
h22E11-Vk1-39-VL    DIQLTQSPSSLSASVGDRVTITCKASQSVDYD-GNSYVNWYQQKPGKAPKLLIYAASNLE
h22E11-Vk4-1-VL     DIVLTQSPDSLAVSLGERATINCKASQSVDYD-GNSYVNWYQQKPGQPPKLLIYAASNLE
22E11-VL            DIVLTQSPASLAVSLGQRATISCKASQSVDYD-GNSYVNWYQQKPGQPPKLLIYAASNLE
h22E11-Vk2-28-VL    DIVLTQSPLSLPVTPGEPASISCKASQSVDYD-GNSYVNWYLQKPGQSPQLLIYAASNLE
2D5-VL              DVLMTQTPLSLPVSLGDQASISCRSSQSIVHTNGNTYLEWYLQKPGQSPKLLIYKVSNRF
                     : :**:* ::** ::  * :: . ::*:  * *    .*:*.**** **:*** ****..:

h22E11-Vk3-11-VL    SGIPARFSGSGSGTDFTLTISSLEPEDFAVYYCQQSNEDPYTFGQGTKVEIK
h22E11-5-VL         SGIPDRFSGSGSGTDFTLTISRLEPEDFAVYYCQQSNEDPYTFGQGTKVEIK
h22E11-Vk1-39-VL    SGVPSRFSGSGSGTDFTLTISSLQPEDFATYYCQQSNEDPYTFGQGTKVEIK
h22E11-Vk4-1-VL     SGVPDRFSGSGSGTDFTLTISSLQAEDVAVYYCQQSNEDPYTFGQGTKVEIK
22E11-VL            SGIPARFSGSGSGTDFTLNIHPVEEDAATYYCQQSNEDPYTFGGGTKLEIK
h22E11-Vk2-28-VL    SGVPDRFSGSGSGTDFTLKISRVEAEDVGVYYCQQSNEDPYTFGQGTKVEIK
2D5-VL              SGVPDRFSGSGSGTDFTLKISRVEAEDLGVYYCFQGSHVPWTFGGGTELEIK
                    **:*.**********:.. **::*.:*.****   ..  : ** *:***
```

FIG. 2B

Ribosome Display Variable Domains

Ribosome Display Antibody - VHs

```
SRP1649-A01    EVQLVESGGGLVQPGGSLRLSCAASGFNISRYYIHWVRQAPGKGLEWVAGITPVRGYTEY
SRP1649-F06    EVQLVESGGGLVQPGGSLRLSCAASGFNIGNYAIHWVRQAPGKGLEWVADITPGQGYTEY
SRP1649-G08    EVQLVESGGGLVQPGGSLRLSCAASGFNISNYVIHWVRQAPGKGLEWVAAITPDGGITEY
SRP1649-C05    EVQLVESGGGLVQPGGSLRLSCAASGFNIGKHVIHWVRQAPGKGLEWVADIVPNGGYTEY
SRP1649-D11    EVQLVESGGGLVQPGGSLRLSCAASGFNISGYVIHWVRQAPGKGLEWVADIIPTAGYTEY
SRP1497-A02    EVQLVESGGGLVRPGGSLRLSCAASGFNISNYAIHWVRQAPGKGLEWVADITPDGGYTDY
SRP1497-A01    EVQLVESGGGLVQPGGSLRLSCAASGFNISNYAIHWVRQAPGKGLEWVADITPDGGYTDY
SRP1497-A05    EVQLVESGGGLVQPGGSLRLSCAASGFNISNYAIHWVRQAPGKGLEWVADITPDGGYTDY
SRP1649-B06    EVQLVESGGGLVQPGGSLRLSCAASGFNISNHAIHWVRQAPGKGLEWVADISPAVGYTDY
SRP1649-D06    EVQLVESGGGLVQPGGSLRLSCAASGFNIRNHAIHWVRQAPGKGLEWVADIAPAGGYTDY
SRP1649-H02    EVQLVESGGGLVQPGGSLRLSCAASGFNIRSYAIHWVRQAPGKGLEWVADITPAGGDTEY
SRP1649-B09    EVQLVESGGGLVQPGGSLRLSCAASGFNIRNNAIHWVRQAPGKGLEWVADITPAGGYTGY
SRP1649-E10    EVQLVESGGGLVQPGGSLRLSCAASGFNISNNVIHWVRQAPGKGLEWVGDIMPGGGSTDY
SRP1649-E08    EVQLVESGGGLVQPGGSLRLSCAASGFSISNYVIHWVRQAPGKGLEWVADISPDGGFTDY
               ************:**.********.*:*  : :*************..*: .  *: *
```

FIG. 3A

| SRP1649-A01 | ADSVKDRFTISADTSKNTAYLQMNSLRAEDTAVYYCARGYVYRMWDSYDYWGQGTLVTVSS |
| SRP1649-F06 | ADSVKDRFTISADTSKNTAYLQMNSLRAEDTAVYYCARGYVYRMWDSYDYWGQGTLVTVSS |
| SRP1649-G08 | ADSVKGRFAISADTSKNTAYLQMNSLRAEDTAVYYCARGYVYRMWDSYDYWGQGTLVTVSS |
| SRP1649-C05 | ADSVKDRFTISADTSKNTAYLQMNSLRAEDTAVYYCARGYVYRMWDSFDYWGQGTLVTVSS |
| SRP1649-D11 | ADSVKGRFTISADTSKNTAYLQMNSLRAEDTAVYYCARGYVYRMWDSFDYWGQGTLVTVSS |
| SRP1497-A02 | ADSVKGRFTISADTSKNTAYLQMNSLRAEDTAVYYCARGYVYRMWDSFDYWGQGTLVTVSS |
| SRP1497-A01 | ADSVKGRFTISADTSKNTAYLQMNSLRAEDTAVYYCARGYVYRMWDSFDYWGQGTLVTVSS |
| SRP1497-A05 | ADSVKDRFTISADTSKNTAYLQMNSLRAEDTAVYYCARGYVYRMWDSFDHWGQGTLVTVSS |
| SRP1649-B06 | ADSVKDRFTISADTSKNTAYLQMNSLRAEDTAVYYCARGYVYRMWDSFDYWGQGTLVTVSS |
| SRP1649-D06 | ADSVKGRFTISADTSKNTAYLQMNSLRAEDTAVYYCARGYVYRMWDSYDYWGQGTLVTVSS |
| SRP1649-H02 | ADSVKGRFTISADTSKNTAYLQMNSLRAEDTAVYYCARGYIYRMWDSYDYWGQGTLVTVSS |
| SRP1649-B09 | ADSVKDRFTISADTSKNTAYLQMNSLRAEDTAVYYCARGYIYRMWDSLDYWGQGTLVTVSS |
| SRP1649-E10 | ADSVKDRFTISADTSKNTAYLQMNSLRAEDTAVYYCARGYVYRMWDSYDYWGQGTLVTVSS |
| SRP1649-E08 | ADSVKDRFTISADTSKNTAYLQMNSLRAEDTAVYYCARGHVYRLWDSFDYWGRGTLVTVSS |
|             | ***: ************************.*::*:**: ******** |

FIG. 3B

ANTI-TIM-3 ANTIBODIES, COMPOSITIONS COMPRISING ANTI-TIM-3 ANTIBODIES AND METHODS OF MAKING AND USING ANTI-TIM-3 ANTIBODIES

REFERENCE TO SEQUENCE LISTING SUBMITTED VIA EFS-WEB

This application includes an electronically submitted sequence listing in .txt format. The .txt file contains a sequence listing entitled "2020-12-28_108843_00138_ST25.txt" created on Dec. 28, 2020 and is 89,069 bytes in size. The sequence listing contained in this .txt file is part of the specification and is hereby incorporated by reference herein in its entirety.

FIELD

Provided herein are antibodies with binding specificity for T cell immunoglobulin domain- and mucin domain-containing molecule 3 (Tim-3) and compositions comprising the antibodies, including pharmaceutical compositions, diagnostic compositions, and kits. Also provided are methods of making anti-Tim-3 antibodies, and methods of using anti-Tim-3 antibodies, for example, for therapeutic purposes, diagnostic purposes, and research purposes.

BACKGROUND

T cell immunoglobulin domain- and mucin domain-containing molecule 3 (Tim-3) is a cell surface protein molecule that belongs to the immunoglobulin superfamily. It is expressed as a transmembrane protein on differentiated type 1 T helper lymphocytes (Th1 cells). See Monney et al., *Nature* 2002, 415:536-541. The Tim-3 protein contains an immunoglobulin variable-like domain and a mucin-like domain. See id. In a mouse model of autoimmune disease, experimental autoimmune encephalomyelitis, antibodies to Tim-3 were shown to increase the number and activation of macrophages, and to enhance clinical and pathologic severity. See id. From this, it has been proposed that Tim-3 is a regulator of immune function. See id. Later studies have shown that Tim-3 is constitutively expressed on cells of the innate immune system and can regulate Th1 immunity. Anderson et al., 2007, *Science* 318:1141-3. Tim-3 has been shown to negatively regulate Th1 cells in several studies. See Sabatos et al., *Nature Immunol.* 4:1102-110; Sanchez-Fueyo et al., 2003, *Nature Immunol.* 4:1093-1101; Sakuishi et al., 2010, *J. Exp. Med.* 207:2187-2194. Galectin-9 and CEACAM1 have been proposed as ligands for Tim-3. Zhu et al., 2005, *Nature Immunol.* 6:1245-1252; Huang et al., 2015, *Nature* 517:386-390.

In addition to its roles in immune regulation, autoimmune conditions, and inflammation, Tim-3 has been proposed as a target for cancer therapeutics. See, e.g., Anderson, 2014, *Cancer Immunol. Res.* 2:393-397. It has been shown that cancer cells can use immune checkpoint regulators such as Tim-3 to suppress the immune response against themselves. See id. Therapeutics that block other checkpoint regulators such as CTLA-4 have proved successful in treating certain cancers. See id. Indeed, target Tim-3 has shown promise for therapies in models of sarcoma, fibrosarcoma, prostate cancer, colon carcinoma, melanoma, and leukemia.

In view of the role of Tim-3 in multiple disease processes, there is a need for improved methods of modulating the immune regulation of Tim-3 and the downstream signaling processes activated by Tim-3. Moreover, given the role of Tim-3 in several diseases, there is also a need for therapeutics that specifically target cells and tissues that express Tim-3.

SUMMARY

Provided herein are antibodies that selectively bind Tim-3. In some embodiments, the antibodies bind human Tim-3. In some embodiments, the antibodies also bind homologs of human Tim-3. In some aspects, the homologs include a cynomolgus monkey homolog.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with one or more conservative amino acid substitutions.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-Tim-3 antibodies provided herein. In some embodiments, the method is a method of treatment. In some embodiments, the method is a diagnostic method. In some embodiments, the method is an analytical method. In some embodiments, the method is a method of purifying and/or quantifying Tim-3.

In some embodiments, the antibodies are used to treat a disease or condition. In some aspects, the disease or condition is selected from a cancer, autoimmune disease, and infection.

BRIEF DESCRIPTION OF THE DRAWINGS

FIG. 2 provides alignments of the VH sequences (SEQ ID NOs: 130-136) and VL sequences (SEQ ID NOs: 151-157) from the hybridomas provided herein. CDRs according to Chothia are bolded, and CDRs according to Kabat are underlined.

FIG. 3 provides an alignment of the VH sequences (SEQ ID NOs: 137-150) from the ribosome display selections provided herein. CDRs according to Chothia are bolded, and CDRs according to Kabat are underlined.

DETAILED DESCRIPTION

1. Definitions

Figure 1:
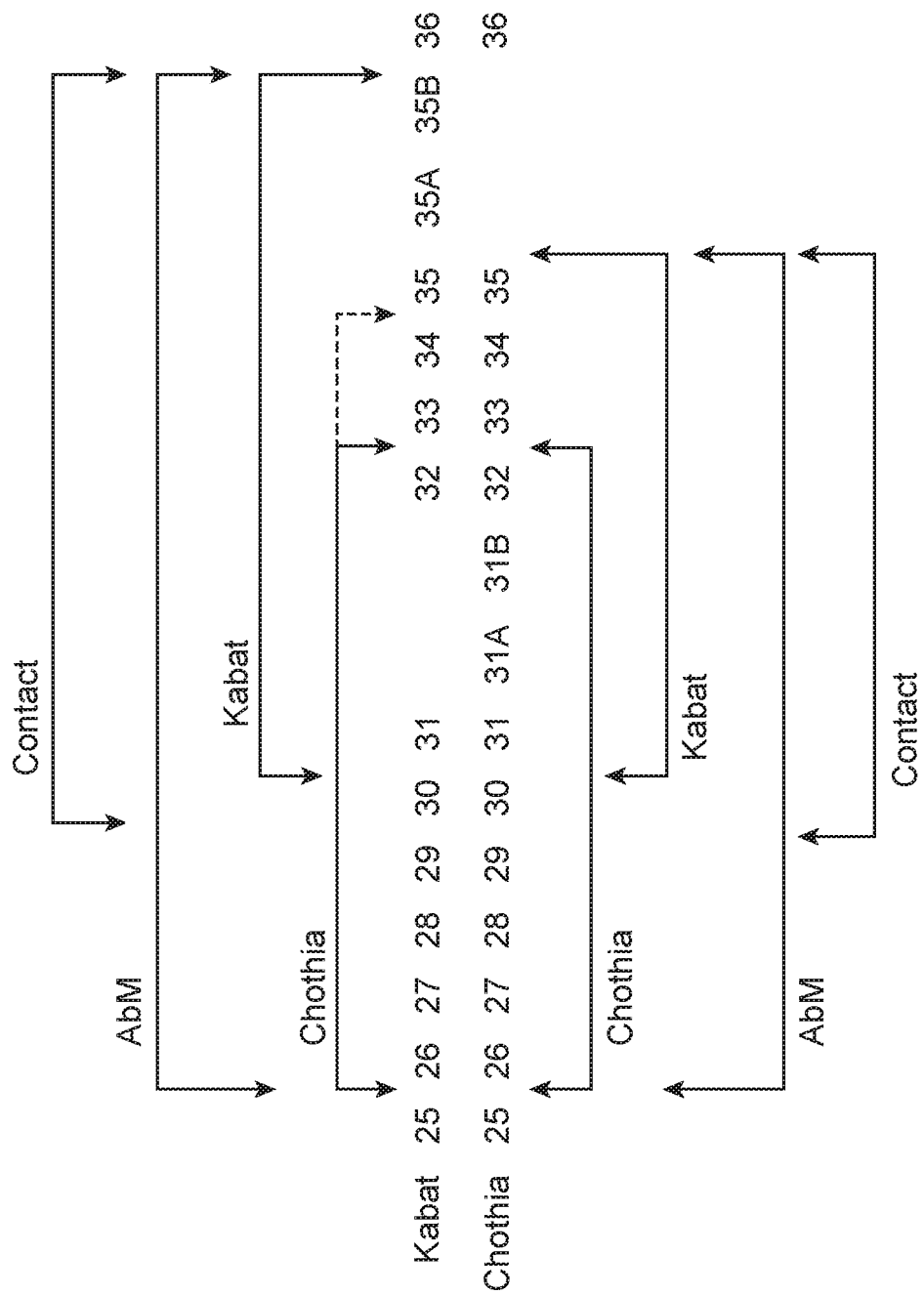
FIG. 1 provides a comparison of the Kabat and Chothia numbering systems for CDR-H1. Adapted from Martin A. C. R. (2010). Protein Sequence and Structure Analysis of Antibody Variable Domains. In R. Kontermann & S. Dubel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "combinations thereof" includes every possible combination of elements to which the term refers to. For example, a sentence stating that "if $\alpha_2$ is A, then $\alpha_3$ is not D; as is not S; or $\alpha_6$ is not S; or combinations thereof" includes the following combinations when $\alpha_2$ is A: (1) $\alpha_3$ is not D; (2) as is not S; (3) $\alpha_6$ is not S; (4) $\alpha_3$ is not D; as is not S; and $\alpha_6$ is not S; (5) $\alpha_3$ is not D and as is not S; (6) $\alpha_3$ is not D and $\alpha_6$ is not S; and (7) as is not S and $\alpha_6$ is not S.

The terms "Tim-3" and "Tim-3 antigen" are used interchangeably herein. Tim-3 is also known by synonyms, including HAVCR2, T cell immunoglobulin domain- and mucin domain-containing molecule 3, and T cell immunoglobulin and mucin domains-containing molecule 3, among others. Unless specified otherwise, the terms include any variants, isoforms and species homologs of human Tim-3 that are naturally expressed by cells, or that are expressed by cells transfected with a Tim-3 gene. Tim-3 proteins include, for example, human Tim-3 (GI: 20330552; SEQ ID NO: 1). In some embodiments, Tim-3 proteins include cynomolgus monkey Tim-3 (GI: 355750365; SEQ ID NO: 2). In some embodiments, Tim-3 proteins include murine Tim-3 (GI: 17148681; SEQ ID NO: 3).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "Tim-3 antibody," "anti-Tim-3 antibody," "Tim-3 Ab," "Tim-3-specific antibody" or "anti-Tim-3 Ab" is an antibody, as described herein, which binds specifically to the antigen Tim-3. In some embodiments, the antibody binds the extracellular domain of Tim-3.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated $\alpha$, $\delta$, $\epsilon$, $\gamma$, and $\mu$, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at http://www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |

TABLE 1-continued

Residues in CDRs according to Kabat and Chothia numbering schemes.

| CDR | Kabat | Chothia |
|---|---|---|
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (Cm) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 168. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$). Any suitable Fc domain known in the art or described herein may be used. In some cases, the Fc domain comprises an IgG1 Fc domain. In some embodiments, the IgG1 Fc domain comprises SEQ ID NO: 159, or a portion thereof, or SEQ ID NO: 165. SEQ ID NO: 159 provides the sequence of $C_{H1}$, $C_{H2}$, and $C_{H3}$ of the human IgG1 constant region. SEQ ID NO: 165 provides the sequence of the constant region used in the illustrative scFv-Fc antibodies provided herein.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" ($sec^{-1}$), as used herein, refers to the dissociation rate constant of a particular antibody-antigen interaction. This value is also referred to as the kw value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" ($M^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., Tim-3). In one exemplary assay, Tim-3 is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to Tim-3 variants with different point-mutations, or to chimeric Tim-3 variants as described further in the Examples provided herein.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. Polypeptide sequences having such substitutions are known as "conservatively modified variants." By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |

TABLE 3-continued

Additional selected groups of amino acids that are considered conservative substitutions for one another, in certain embodiments.

| | |
|---|---|
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a cancer that can be treated or diagnosed with an antibody provided herein. In some embodiments, the cancer is a cancer of epithelial origin.

2. Antibodies

Provided herein are antibodies that selectively bind human Tim-3. In some aspects, the antibody selectively binds to the extracellular domain of human Tim-3.

In some embodiments, the antibody binds to a homolog of human Tim-3. In some aspects, the antibody binds to a homolog of human Tim-3 from a species selected from monkeys, mice, dogs, cats, rats, cows, horses, goats and sheep. In some aspects, the homolog is a cynomolgus monkey homolog.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 9, 10, 11, 12, or 13 residues in length.

In some aspects, the Kabat/Chothia CDR-L1 of the antibody is 11, 12, 13, 14, 15, 16, 17, or 18 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fab' fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the scFv-Fc fragment comprises a constant region wherein the constant region comprises SEQ ID NO: 165. The constant region in SEQ ID NO: 165 differs from the human IgG1 constant region of SEQ ID NO: 159 in several respects. First, the sequence in SEQ ID NO: 165 comprises the linker AAGSDQEPKSS (SEQ ID NO: 168). SEQ ID NO: 165 also does not comprise the CH1 domain of the IgG1 constant region. SEQ ID NO: 165 further comprises a C220S (EU numbering system) mutation, which removes an unpaired cysteine reside that is not needed when the light chain constant region is not present (e.g., in an scFv-Fc format). SEQ ID NO: 165 further comprises two, optional, P to S mutations (P230S and P238S by the EU numbering system). Either or both of these serine residues can be reverted to the naturally occurring proline residues. Finally, SEQ ID NO: 165 comprises an aspartic acid (D) residue at EU position 356 and a leucine (L) residue at EU position 358. In contrast, SEQ ID NO: 159 comprises glutamic acid (E) in EU position 356 and methionine (M) in EU position 358. In some embodiments, the antibodies provided herein comprise constant regions comprising D356/L358, E356/M358, D356/M358, or E356/L358 (EU numbering). However, a skilled person will recognize that the antibodies provide herein may comprise any suitable constant region and that the constant region sequences provided herein are for illustrative purposes.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

In some embodiments, the antibody inhibits the binding of Tim-3 to one or more of its ligands. In some aspects, the antibody inhibits the binding of Tim-3 to a ligand selected from a second Tim-3 molecule, claudin-7, CD44v4-v7, E-cadherin, and CD9.

The antibodies provided herein may be useful for the treatment of a variety of diseases and conditions including cancers. In particular, the antibodies provided herein may be useful for the treatment of cancers of epithelial origin.

2.1. CDR-H3 Sequences

In some embodiments, the antibody comprises a CDR-H3 sequence comprising, consisting of, or consisting essentially of a CDR-H3 sequence of an illustrative antibody or $V_H$ sequence provided herein. In some aspects, the CDR-H3 sequence is a CDR-H3 sequence of an scFv-Fc sequence provided in SEQ ID NO: 169. In some aspects, the CDR-H3 sequence is a CDR-H3 sequence of a $V_H$ sequence provided in SEQ ID NOs.: 130-150.

In some embodiments, the antibody comprises a CDR-H3 sequence comprising, consisting of, or consisting essentially of a sequence selected from SEQ ID NOs: 88-108. In some aspects, the antibody comprises a CDR-H3 sequence comprising, consisting of, or consisting essentially of SEQ ID NO: 88. In some aspects, the antibody comprises a CDR-H3 sequence comprising, consisting of, or consisting essentially of SEQ ID NO: 89. In some aspects, the antibody comprises a CDR-H3 sequence comprising, consisting of, or consisting essentially of SEQ ID NO: 90. In some aspects, the antibody comprises a CDR-H3 sequence comprising, consisting of, or consisting essentially of SEQ ID NO: 91. In some aspects, the antibody comprises a CDR-H3 sequence comprising, consisting of, or consisting essentially of SEQ ID NO: 92. In some aspects, the antibody comprises a CDR-H3 sequence comprising, consisting of, or consisting essentially of SEQ ID NO: 93. In some aspects, the antibody comprises a CDR-H3 sequence comprising, consisting of, or consisting essentially of SEQ ID NO: 94. In some aspects, the antibody comprises a CDR-H3 sequence comprising, consisting of, or consisting essentially of SEQ ID NO: 95. In some aspects, the antibody comprises a CDR-H3 sequence comprising, consisting of, or consisting essentially of SEQ ID NO: 96. In some aspects, the antibody comprises a CDR-H3 sequence comprising, consisting of, or consisting essentially of SEQ ID NO: 97. In some aspects, the antibody comprises a CDR-H3 sequence comprising, consisting of, or consisting essentially of SEQ ID NO: 98. In some aspects, the antibody comprises a CDR-H3 sequence comprising, consisting of, or consisting essentially of SEQ ID NO: 99. In some aspects, the antibody comprises a CDR-H3 sequence comprising, consisting of, or consisting essentially of SEQ ID NO: 100. In some aspects, the antibody comprises a CDR-H3 sequence comprising, consisting of, or consisting essentially of SEQ ID NO: 101. In some aspects, the antibody comprises a CDR-H3 sequence comprising, consisting of, or consisting essentially of SEQ ID NO: 102. In some aspects, the antibody comprises a CDR-H3 sequence comprising, consisting of, or consisting essentially of SEQ ID NO: 103. In some aspects, the antibody comprises a CDR-H3 sequence comprising, consisting of, or consisting essentially of SEQ ID NO: 104. In some aspects, the antibody comprises a CDR-H3 sequence comprising, consisting of, or consisting essentially of SEQ ID NO: 105. In some aspects, the antibody comprises a CDR-H3 sequence comprising, consisting of, or consisting essentially of SEQ ID NO: 106. In some aspects, the antibody comprises a CDR-H3 sequence comprising, consisting of, or consisting essentially of SEQ ID NO: 107. In some aspects, the antibody comprises a CDR-H3 sequence comprising, consisting of, or consisting essentially of SEQ ID NO: 108.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof. In some embodiments, the CDR-H sequences comprise, consist of, or consist essentially of one or more CDR-H sequences provided in a $V_H$ sequence selected from SEQ ID NOs: 130-150.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a $V_H$ sequence comprising a CDR-H3 sequence, wherein the CDR-H3 sequence comprises, consists of, or consists essentially of a Kabat CDR-H3 sequence of an illustrative antibody or $V_H$ sequence provided herein. In some aspects, the Kabat CDR-H3 sequence is a Kabat CDR-H3 sequence of an scFv-Fc sequence provided in SED ID NO.: 169. In some aspects, the Kabat CDR-H3 sequence is a Kabat CDR-H3 sequence of a $V_H$ sequence provided in SEQ ID NOs.: 130-150.

In some embodiments, the antibody comprises a $V_H$ sequence comprising a Kabat CDR-H3 sequence comprising, consisting of, or consisting essentially of a sequence selected from SEQ ID NOs: 88-108. In some aspects, the antibody comprises a $V_H$ sequence comprising a Kabat CDR-H3 sequence comprising, consisting of, or consisting essentially of SEQ ID NO: 88. In some aspects, the antibody comprises a $V_H$ sequence comprising a Kabat CDR-H3 sequence comprising, consisting of, or consisting essentially of SEQ ID NO: 89. In some aspects, the antibody comprises a $V_H$ sequence comprising a Kabat CDR-H3 sequence comprising, consisting of, or consisting essentially of SEQ ID NO: 90. In some aspects, the antibody comprises a $V_H$ sequence comprising a Kabat CDR-H3 sequence comprising, consisting of, or consisting essentially of SEQ ID NO: 91. In some aspects, the antibody comprises a $V_H$ sequence comprising a Kabat CDR-H3 sequence comprising, consisting of, or consisting essentially of SEQ ID NO: 92. In some aspects, the antibody comprises a $V_H$ sequence comprising a Kabat CDR-H3 sequence comprising, consisting of, or consisting essentially of SEQ ID NO: 93. In some aspects, the antibody comprises a $V_H$ sequence comprising a Kabat CDR-H3 sequence comprising, consisting of, or consisting essentially of SEQ ID NO: 94. In some aspects, the antibody comprises a $V_H$ sequence comprising a Kabat CDR-H3 sequence comprising, consisting of, or consisting essentially of SEQ ID NO: 95. In some aspects, the antibody comprises a $V_H$ sequence comprising a Kabat CDR-H3 sequence comprising, consisting of, or consisting essentially of SEQ ID NO: 96. In some aspects, the antibody comprises a $V_H$ sequence comprising a Kabat CDR-H3 sequence comprising, consisting of, or consisting essentially of SEQ ID NO: 97. In some aspects, the antibody comprises a $V_H$ sequence comprising a Kabat CDR-H3 sequence comprising, consisting of, or consisting essentially of SEQ ID NO: 98. In some aspects, the antibody comprises a $V_H$ sequence comprising a Kabat CDR-H3 sequence comprising, consisting of, or consisting essentially of SEQ ID NO: 99. In some aspects, the antibody comprises a $V_H$ sequence comprising a Kabat CDR-H3 sequence comprising, consisting of, or consisting essentially of SEQ ID NO: 100. In some aspects, the antibody comprises a $V_H$ sequence comprising a Kabat CDR-H3 sequence comprising, consisting of, or consisting essentially of SEQ ID NO: 101. In some aspects, the antibody comprises a $V_H$ sequence comprising a Kabat CDR-H3 sequence comprising, consisting of, or consisting essentially of SEQ ID NO: 102. In some aspects, the antibody comprises a $V_H$ sequence comprising a Kabat CDR-H3 sequence comprising, consisting of, or consisting essentially of SEQ ID NO: 103. In some aspects, the antibody comprises a $V_H$ sequence comprising a Kabat CDR-H3 sequence comprising, consisting of, or consisting essentially of SEQ ID NO: 104. In some aspects, the antibody comprises a $V_H$ sequence comprising a Kabat CDR-H3 sequence comprising, consisting of, or consisting essentially of SEQ ID NO: 105. In some aspects, the antibody comprises a $V_H$ sequence comprising a Kabat CDR-H3 sequence comprising, consisting of, or consisting essentially of SEQ ID NO: 106. In some aspects, the antibody comprises a $V_H$ sequence comprising a Kabat CDR-H3 sequence comprising, consisting of, or consisting essentially of SEQ ID NO: 107. In some aspects, the antibody comprises a $V_H$ sequence comprising a Kabat CDR-H3 sequence comprising, consisting of, or consisting essentially of SEQ ID NO: 108.

2.2.1.2. Kabat CDR-H2

In some embodiments, the antibody comprises a $V_H$ sequence comprising a CDR-H2 sequence, wherein the CDR-H2 sequence comprises, consists of, or consists essentially of a Kabat CDR-H2 sequence of an illustrative antibody or $V_H$ sequence provided herein. In some aspects, the Kabat CDR-H2 sequence is a Kabat CDR-H2 sequence of an scFv-Fc sequence provided in SED ID NO.: 169. In some aspects, the Kabat CDR-H3 sequence is a Kabat CDR-H3 sequence of a $V_H$ sequence provided in SEQ ID NOs.: 130-150.

In some embodiments, the antibody comprises a $V_H$ sequence comprising a Kabat CDR-H2 sequence comprising, consisting of, or consisting essentially of a sequence selected from SEQ ID NOs: 67-87. In some aspects, the antibody comprises a $V_H$ sequence comprising a Kabat CDR-H2 sequence comprising, consisting of, or consisting essentially of SEQ ID NO: 67. In some aspects, the antibody comprises a $V_H$ sequence comprising a Kabat CDR-H2 sequence comprising, consisting of, or consisting essentially of SEQ ID NO: 68. In some aspects, the antibody comprises a $V_H$ sequence comprising a Kabat CDR-H2 sequence comprising, consisting of, or consisting essentially of SEQ ID NO: 69. In some aspects, the antibody comprises a $V_H$ sequence comprising a Kabat CDR-H2 sequence comprising, consisting of, or consisting essentially of SEQ ID NO: 70. In some aspects, the antibody comprises a $V_H$ sequence comprising a Kabat CDR-H2 sequence comprising, consisting of, or consisting essentially of SEQ ID NO: 71. In some aspects, the antibody comprises a $V_H$ sequence comprising a Kabat CDR-H2 sequence comprising, consisting of, or consisting essentially of SEQ ID NO: 72. In some aspects, the antibody comprises a $V_H$ sequence comprising a Kabat CDR-H2 sequence comprising, consisting of, or consisting essentially of SEQ ID NO: 73. In some aspects, the antibody comprises a $V_H$ sequence comprising a Kabat CDR-H2 sequence comprising, consisting of, or consisting essentially of SEQ ID NO: 74. In some aspects, the antibody comprises a $V_H$ sequence comprising a Kabat CDR-H2 sequence comprising, consisting of, or consisting essentially of SEQ ID NO: 75. In some aspects, the antibody comprises a $V_H$ sequence comprising a Kabat CDR-H2 sequence comprising, consisting of, or consisting essentially of SEQ ID NO: 76. In some aspects, the antibody comprises a $V_H$ sequence comprising a Kabat CDR-H2 sequence comprising, consisting of, or consisting essentially of SEQ ID NO: 77. In some aspects, the antibody comprises a $V_H$ sequence comprising a Kabat CDR-H2 sequence comprising, consisting of, or consisting essentially of SEQ ID NO: 78. In some aspects, the antibody comprises a $V_H$ sequence comprising a Kabat CDR-H2 sequence comprising, consisting of, or consisting essentially of SEQ ID NO: 79. In some aspects, the antibody comprises a $V_H$ sequence comprising a Kabat CDR-H2 sequence comprising, consisting of, or consisting essentially of SEQ ID NO: 80. In some aspects, the antibody comprises a $V_H$ sequence comprising a Kabat CDR-H2 sequence comprising, consisting of, or consisting essentially of SEQ ID NO: 81. In some aspects, the antibody comprises a $V_H$ sequence comprising a Kabat CDR-H2 sequence comprising, consisting of, or consisting essentially of SEQ ID NO: 82. In some aspects, the antibody comprises a $V_H$ sequence comprising a Kabat CDR-H2 sequence comprising, consisting of, or consisting essentially of SEQ ID NO: 83. In some aspects, the antibody comprises a $V_H$ sequence comprising a Kabat CDR-H2 sequence comprising, consisting of, or consisting essentially of SEQ ID NO: 84. In some aspects, the antibody comprises a $V_H$ sequence comprising a Kabat CDR-H2 sequence comprising, consisting of, or consisting essentially of SEQ ID NO: 85. In some aspects, the antibody comprises a $V_H$ sequence comprising a Kabat CDR-H2 sequence comprising, consisting of, or consisting essentially of SEQ ID NO: 86. In some aspects, the antibody comprises a $V_H$ sequence comprising a Kabat CDR-H2 sequence comprising, consisting of, or consisting essentially of SEQ ID NO: 87.

2.2.1.3. Kabat CDR-H1

In some embodiments, the antibody comprises a $V_H$ sequence comprising a CDR-H1 sequence, wherein the CDR-H1 sequence comprises, consists of, or consists essentially of a Kabat CDR-H1 sequence of an illustrative antibody or $V_H$ sequence provided herein. In some aspects, the Kabat CDR-H1 sequence is a Kabat CDR-H1 sequence of an scFv-Fc sequence provided in SEQ ID NO: 169. In some aspects, the Kabat CDR-H3 sequence is a Kabat CDR-H1 sequence of a $V_H$ sequence provided in SEQ ID NOs.: 130-150.

In some embodiments, the antibody comprises a $V_H$ sequence comprising a Kabat CDR-H1 sequence comprising, consisting of, or consisting essentially of a sequence selected from SEQ ID NOs: 25-45. In some aspects, the antibody comprises a $V_H$ sequence comprising a Kabat CDR-H1 sequence comprising, consisting of, or consisting essentially of SEQ ID NO: 25. In some aspects, the antibody comprises a $V_H$ sequence comprising a Kabat CDR-H1 sequence comprising, consisting of, or consisting essentially of SEQ ID NO: 26. In some aspects, the antibody comprises a $V_H$ sequence comprising a Kabat CDR-H1 sequence comprising, consisting of, or consisting essentially of SEQ ID NO: 27. In some aspects, the antibody comprises a $V_H$ sequence comprising a Kabat CDR-H1 sequence comprising, consisting of, or consisting essentially of SEQ ID NO: 28. In some aspects, the antibody comprises a $V_H$ sequence comprising a Kabat CDR-H1 sequence comprising, consisting of, or consisting essentially of SEQ ID NO: 29. In some aspects, the antibody comprises a $V_H$ sequence comprising a Kabat CDR-H1 sequence comprising, consisting of, or consisting essentially of SEQ ID NO: 30. In some aspects, the antibody comprises a $V_H$ sequence comprising a Kabat CDR-H1 sequence comprising, consisting of, or consisting essentially of SEQ ID NO: 31. In some aspects, the antibody comprises a $V_H$ sequence comprising a Kabat CDR-H1 sequence comprising, consisting of, or consisting essentially of SEQ ID NO: 32. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34. In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36. In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a $V_H$ sequence comprising a Kabat CDR-H1 sequence comprising, consisting of, or consisting essentially of SEQ ID NO: 45.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 88-108, and a Kabat CDR-H2 sequence comprising, consisting of, or consisting essentially of a sequence selected from SEQ ID NOs: 67-87. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 130-150.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 88-108, and a Kabat CDR-H1 sequence comprising, consisting of, or consisting essentially of a sequence selected from SEQ ID NOs: 25-45. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 130-150.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 25-45 and a Kabat CDR-H2 sequence comprising, consisting of, or consisting essentially of a sequence selected from SEQ ID NOs: 67-87. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 130-150.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 25-45, a Kabat CDR-H2 sequence comprising, consisting of, or consisting essentially of a sequence selected from SEQ ID NOs: 67-87, and a Kabat CDR-H3 sequence comprising, consisting of, or consisting essentially of a sequence selected from SEQ ID NOs: 88-108. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 130-150.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof

2.2.2.1. Chothia CDR-H3

In some embodiments, the antibody comprises a $V_H$ sequence comprising a CDR-H3 sequence, wherein the CDR-H3 sequence comprises, consists of, or consists essentially of a Chothia CDR-H3 sequence of an illustrative antibody or $V_H$ sequence provided herein. In some aspects, the Chothia CDR-H3 sequence is a Chothia CDR-H3 sequence of an scFv-Fc sequence provided in SEQ ID NO: 169. In some aspects, the Chothia CDR-H3 sequence is a Chothia CDR-H3 sequence of a $V_H$ sequence provided in SEQ ID NOs.: 130-150.

In some embodiments, the antibody comprises a $V_H$ sequence comprising a Chothia CDR-H3 sequence comprising, consisting of, or consisting essentially of a sequence selected from SEQ ID NOs: 88-108. In some aspects, the antibody comprises a $V_H$ sequence comprising a Chothia CDR-H3 sequence comprising, consisting of, or consisting essentially of SEQ ID NO: 88. In some aspects, the antibody comprises a $V_H$ sequence comprising a Chothia CDR-H3 sequence comprising, consisting of, or consisting essentially of SEQ ID NO: 89. In some aspects, the antibody comprises a $V_H$ sequence comprising a Chothia CDR-H3 sequence comprising, consisting of, or consisting essentially of SEQ ID NO: 90. In some aspects, the antibody comprises a $V_H$ sequence comprising a Chothia CDR-H3 sequence comprising, consisting of, or consisting essentially of SEQ ID NO: 91. In some aspects, the antibody comprises a $V_H$ sequence comprising a Chothia CDR-H3 sequence comprising, consisting of, or consisting essentially of SEQ ID NO: 92. In some aspects, the antibody comprises a $V_H$ sequence comprising a Chothia CDR-H3 sequence comprising, consisting of, or consisting essentially of SEQ ID NO: 93. In some aspects, the antibody comprises a $V_H$ sequence comprising a Chothia CDR-H3 sequence comprising, consisting of, or consisting essentially of SEQ ID NO: 94. In some aspects, the antibody comprises a $V_H$ sequence comprising a Chothia CDR-H3 sequence comprising, consisting of, or consisting essentially of SEQ ID NO: 95. In some aspects, the antibody comprises a $V_H$ sequence comprising a Chothia CDR-H3 sequence comprising, consisting of, or consisting essentially of SEQ ID NO: 96. In some aspects, the antibody comprises a $V_H$ sequence comprising a Chothia CDR-H3 sequence comprising, consisting of, or consisting essentially of SEQ ID NO: 97. In some aspects, the antibody comprises a $V_H$ sequence comprising a Chothia CDR-H3 sequence comprising, consisting of, or consisting essentially of SEQ ID NO: 98. In some aspects, the antibody comprises a $V_H$ sequence comprising a Chothia CDR-H3 sequence comprising, consisting of, or consisting essentially of SEQ ID NO: 99. In some aspects, the antibody comprises a $V_H$ sequence comprising a Chothia CDR-H3 sequence comprising, consisting of, or consisting essentially of SEQ ID NO: 100. In some aspects, the antibody comprises a $V_H$ sequence comprising a Chothia CDR-H3 sequence comprising, consisting of, or consisting essentially of SEQ ID NO: 101. In some aspects, the antibody comprises a $V_H$ sequence comprising a Chothia CDR-H3 sequence comprising, consisting of, or consisting essentially of SEQ ID NO: 102. In some aspects, the antibody comprises a $V_H$ sequence comprising a Chothia CDR-H3 sequence comprising, consisting of, or consisting essentially of SEQ ID NO: 103. In some aspects, the antibody comprises a $V_H$ sequence comprising a Chothia CDR-H3 sequence comprising, consisting of, or consisting essentially of SEQ ID NO: 104. In some aspects, the antibody comprises a $V_H$ sequence comprising a Chothia CDR-H3 sequence comprising, consisting of, or consisting essentially of SEQ ID NO: 105. In some aspects, the antibody comprises a $V_H$ sequence comprising a Chothia CDR-H3 sequence comprising, consisting of, or consisting essentially of SEQ ID NO: 106. In some aspects, the antibody comprises a $V_H$ sequence comprising a Chothia CDR-H3 sequence comprising, consisting of, or consisting essentially of SEQ ID NO: 107. In some aspects, the antibody comprises a $V_H$ sequence comprising a Chothia CDR-H3 sequence comprising, consisting of, or consisting essentially of SEQ ID NO: 108.

2.2.2.2. Chothia CDR-H2

In some embodiments, the antibody comprises a $V_H$ sequence comprising a CDR-H2 sequence, wherein the CDR-H2 sequence comprises, consists of, or consists essentially of a Chothia CDR-H2 sequence of an illustrative antibody or $V_H$ sequence provided herein. In some aspects, the Chothia CDR-H2 sequence is a Chothia CDR-H2 sequence of an scFv-Fc sequence provided in SEQ ID NO: 169. In some aspects, the Chothia CDR-H2 sequence is a Chothia CDR-H2 sequence of a $V_H$ sequence provided in SEQ ID NOs.: 130-150.

In some embodiments, the antibody comprises a $V_H$ sequence comprising a Chothia CDR-H2 sequence comprising, consisting of, or consisting essentially of a sequence selected from SEQ ID NOs: 46-66. In some aspects, the antibody comprises a $V_H$ sequence comprising a Chothia CDR-H2 sequence comprising, consisting of, or consisting essentially of SEQ ID NO: 46. In some aspects, the antibody comprises a $V_H$ sequence comprising a Chothia CDR-H2 sequence comprising, consisting of, or consisting essentially of SEQ ID NO: 47. In some aspects, the antibody comprises a $V_H$ sequence comprising a Chothia CDR-H2 sequence comprising, consisting of, or consisting essentially of SEQ ID NO: 48. In some aspects, the antibody comprises a $V_H$ sequence comprising a Chothia CDR-H2 sequence comprising, consisting of, or consisting essentially of SEQ ID NO: 49. In some aspects, the antibody comprises a $V_H$ sequence comprising a Chothia CDR-H2 sequence comprising, consisting of, or consisting essentially of SEQ ID NO: 50. In some aspects, the antibody comprises a $V_H$ sequence comprising a Chothia CDR-H2 sequence comprising, consisting of, or consisting essentially of SEQ ID NO: 51. In some aspects, the antibody comprises a $V_H$ sequence comprising a Chothia CDR-H2 sequence comprising, consisting of, or consisting essentially of SEQ ID NO: 52. In some aspects, the antibody comprises a $V_H$ sequence comprising a Chothia CDR-H2 sequence comprising, consisting of, or consisting essentially of SEQ ID NO: 53. In some aspects, the antibody comprises a $V_H$ sequence comprising a Chothia CDR-H2 sequence comprising, consisting of, or consisting essentially of SEQ ID NO: 54. In some aspects, the antibody comprises a $V_H$ sequence comprising a Chothia CDR-H2 sequence comprising, consisting of, or consisting essentially of SEQ ID NO: 55. In some aspects, the antibody comprises a $V_H$ sequence comprising a Chothia CDR-H2 sequence comprising, consisting of, or consisting essentially of SEQ ID NO: 56. In some aspects, the antibody comprises a $V_H$ sequence comprising a Chothia CDR-H2 sequence comprising, consisting of, or consisting essentially of SEQ ID NO: 57. In some aspects, the antibody comprises a $V_H$ sequence comprising a Chothia CDR-H2 sequence comprising, consisting of, or consisting essentially of SEQ ID NO: 58. In some aspects, the antibody comprises a $V_H$ sequence comprising a Chothia CDR-H2 sequence comprising, consisting of, or consisting essentially of SEQ ID NO: 59. In some aspects, the antibody comprises a $V_H$ sequence comprising a Chothia CDR-H2 sequence comprising, consisting of, or consisting essentially of SEQ ID NO: 60. In some aspects, the antibody comprises a $V_H$ sequence comprising a Chothia CDR-H2 sequence comprising, consisting of, or consisting essentially of SEQ ID NO: 61. In some aspects, the antibody comprises a $V_H$ sequence comprising a Chothia CDR-H2 sequence comprising, consisting of, or consisting essentially of SEQ ID NO: 62. In some aspects, the antibody comprises a $V_H$ sequence comprising a Chothia CDR-H2 sequence comprising, consisting of, or consisting essentially of SEQ ID NO: 63. In some aspects, the antibody comprises a $V_H$ sequence comprising a Chothia CDR-H2 sequence comprising, consisting of, or consisting essentially of SEQ ID NO: 64. In some aspects, the antibody comprises a $V_H$ sequence comprising a Chothia CDR-H2 sequence comprising, consisting of, or consisting essentially of SEQ ID NO: 65. In some aspects, the antibody comprises a $V_H$ sequence comprising a Chothia CDR-H2 sequence comprising, consisting of, or consisting essentially of SEQ ID NO: 66.

2.2.2.3. Chothia CDR-H1

In some embodiments, the antibody comprises a $V_H$ sequence comprising a CDR-H1 sequence, wherein the CDR-H1 sequence comprises, consists of, or consists essentially of a Chothia CDR-H1 sequence of an illustrative antibody or $V_H$ sequence provided herein. In some aspects, the Chothia CDR-H1 sequence is a Chothia CDR-H1 sequence of an scFv-Fc sequence provided in SEQ ID NO: 169. In some aspects, the Chothia CDR-H1 sequence is a Chothia CDR-H1 sequence of a $V_H$ sequence provided in SEQ ID NOs.: 130-150.

In some embodiments, the antibody comprises a $V_H$ sequence comprising a Chothia CDR-H1 sequence comprising, consisting of, or consisting essentially of a sequence selected from SEQ ID NOs: 4-24. In some aspects, the antibody comprises a $V_H$ sequence comprising a Chothia CDR-H1 sequence comprising, consisting of, or consisting essentially of SEQ ID NO: 4. In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a $V_H$ sequence comprising a Chothia CDR-H1 sequence comprising, consisting of, or consisting essentially of SEQ ID NO: 24.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 88-108, and a Chothia CDR-H2 sequence comprising, consisting of, or consisting essentially of a sequence selected from SEQ ID NOs: 46-66. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 130-150.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 88-108, and a Chothia CDR-H1 sequence comprising, consisting of, or consisting essentially of a sequence selected from SEQ ID NOs: 4-24. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 130-150.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 4-24 and a Chothia CDR-H2 sequence comprising, consisting of, or consisting essentially of a sequence selected from SEQ ID NOs: 46-66. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 130-150.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 4-24, a Chothia CDR-H2 sequence comprising, consisting of, or consisting essentially of a sequence selected from SEQ ID NOs: 46-66, and a Chothia CDR-H3 sequence comprising, consisting of, or consisting essentially of a sequence selected from SEQ ID NOs: 88-108. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 130-150.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.3. $V_H$ Sequences

In some embodiments, the antibody comprises, consists of, or consists essentially of a $V_H$ sequence of an scFv-Fc sequence provided in SEQ ID NO: 169. In some embodiments, the antibody comprises, consists of, or consists essentially of a $V_H$ sequence provided in SEQ ID NOs.: 130-150.

In some embodiments, the antibody comprises a $V_H$ sequence comprising, consisting of, or consisting essentially of a sequence selected from SEQ ID NOs: 130-150. In some aspects, the antibody comprises a $V_H$ sequence comprising, consisting of, or consisting essentially of SEQ ID NO: 130. In some aspects, the antibody comprises a $V_H$ sequence comprising, consisting of, or consisting essentially of SEQ ID NO: 131. In some aspects, the antibody comprises a $V_H$ sequence comprising, consisting of, or consisting essentially of SEQ ID NO: 132. In some aspects, the antibody comprises a $V_H$ sequence comprising, consisting of, or consisting essentially of SEQ ID NO: 133. In some aspects, the antibody comprises a $V_H$ sequence comprising, consisting of, or consisting essentially of SEQ ID NO: 134. In some aspects, the antibody comprises a $V_H$ sequence comprising, consisting of, or consisting essentially of SEQ ID NO: 135. In some aspects, the antibody comprises a $V_H$ sequence comprising, consisting of, or consisting essentially of SEQ ID NO: 136. In some aspects, the antibody comprises a $V_H$ sequence comprising, consisting of, or consisting essentially of SEQ ID NO: 137. In some aspects, the antibody comprises a $V_H$ sequence comprising, consisting of, or consisting essentially of SEQ ID NO: 138. In some aspects, the antibody comprises a $V_H$ sequence comprising, consisting of, or consisting essentially of SEQ ID NO: 139. In some aspects, the antibody comprises a $V_H$ sequence comprising, consisting of, or consisting essentially of SEQ ID NO: 140. In some aspects, the antibody comprises a $V_H$ sequence comprising, consisting of, or consisting essentially of SEQ ID NO: 141. In some aspects, the antibody comprises a $V_H$ sequence comprising, consisting of, or consisting essentially of SEQ ID NO: 142. In some aspects, the antibody comprises a $V_H$ sequence comprising, consisting of, or consisting essentially of SEQ ID NO: 143. In some aspects, the antibody comprises a $V_H$ sequence comprising, consisting of, or consisting essentially of SEQ ID NO: 144. In some aspects, the antibody comprises a $V_H$ sequence comprising, consisting of, or consisting essentially of SEQ ID NO: 145. In some aspects, the antibody comprises a $V_H$ sequence comprising, consisting of, or consisting essentially of SEQ ID NO: 146. In some aspects, the antibody comprises a $V_H$ sequence comprising, consisting of, or consisting essentially of SEQ ID NO: 147. In some aspects, the antibody comprises a $V_H$ sequence comprising, consisting of, or consisting essentially of SEQ ID NO: 148. In some aspects, the antibody comprises a $V_H$ sequence comprising, consisting of, or consisting essentially of SEQ ID NO: 149. In some aspects, the antibody comprises a $V_H$ sequence comprising, consisting of, or consisting essentially of SEQ ID NO: 150.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.4. CDR-L3 Sequences

In some embodiments, the antibody comprises a CDR-L3 sequence comprising, consisting of, or consisting essentially of a CDR-L3 sequence of an illustrative antibody or $V_L$ sequence provided herein. In some aspects, the CDR-L3 sequence is a CDR-L3 sequence of an scFv-Fc sequence provided in SEQ ID NO: 169. In some aspects, the CDR-L3 sequence is a CDR-L3 sequence of a $V_L$ sequence provided in SEQ ID NOs.: 151-158.

In some embodiments, the antibody comprises a CDR-L3 sequence comprising, consisting of, or consisting essentially of a sequence selected from SEQ ID NOs: 123-129. In some aspects, the antibody comprises a CDR-L3 sequence comprising, consisting of, or consisting essentially of SEQ ID NO: 123. In some aspects, the antibody comprises a CDR-L3 sequence comprising, consisting of, or consisting essentially of SEQ ID NO: 124. In some aspects, the antibody comprises a CDR-L3 sequence comprising, consisting of, or consisting essentially of SEQ ID NO: 125. In some aspects, the antibody comprises a CDR-L3 sequence comprising, consisting of, or consisting essentially of SEQ ID NO: 126. In some aspects, the antibody comprises a CDR-L3 sequence comprising, consisting of, or consisting essentially of SEQ ID NO: 127. In some aspects, the antibody comprises a CDR-L3 sequence comprising, consisting of, or consisting essentially of SEQ ID NO: 128. In some aspects, the antibody comprises a CDR-L3 sequence comprising, consisting of, or consisting essentially of SEQ ID NO: 129.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof 2.5.1. CDR-L3

In some embodiments, the antibody comprises a $V_L$ sequence comprising a CDR-L3 sequence, wherein the CDR-L3 sequence comprises, consists of, or consists essentially of a CDR-L3 sequence of an illustrative antibody or $V_L$ sequence provided herein. In some aspects, the CDR-L3 sequence is a CDR-L3 sequence of an scFv-Fc sequence provided in SEQ ID NO: 169. In some aspects, the CDR-L3 sequence is a CDR-L3 sequence of a $V_L$ sequence provided in SEQ ID NOs.: 151-158.

In some embodiments, the antibody comprises a $V_L$ sequence comprising a CDR-L3 sequence comprising, consisting of, or consisting essentially of a sequence selected from SEQ ID NOs: 123-129. In some aspects, the antibody comprises a $V_L$ sequence comprising a CDR-L3 sequence comprising, consisting of, or consisting essentially of SEQ ID NO: 123. In some aspects, the antibody comprises a $V_L$ sequence comprising a CDR-L3 sequence comprising, consisting of, or consisting essentially of SEQ ID NO: 124. In some aspects, the antibody comprises a $V_L$ sequence comprising a CDR-L3 sequence comprising, consisting of, or consisting essentially of SEQ ID NO: 125. In some aspects, the antibody comprises a $V_L$ sequence comprising a CDR-L3 sequence comprising, consisting of, or consisting essentially of SEQ ID NO: 126. In some aspects, the antibody comprises a $V_L$ sequence comprising a CDR-L3 sequence comprising, consisting of, or consisting essentially of SEQ ID NO: 127. In some aspects, the antibody comprises a $V_L$ sequence comprising a CDR-L3 sequence comprising, consisting of, or consisting essentially of SEQ ID NO: 128. In some aspects, the antibody comprises a $V_L$ sequence comprising a CDR-L3 sequence comprising, consisting of, or consisting essentially of SEQ ID NO: 129.

2.5.2. CDR-L2

In some embodiments, the antibody comprises a $V_L$ sequence comprising a CDR-L2 sequence, wherein the CDR-L2 sequence comprises, consists of, or consists essentially of a CDR-L2 sequence of an illustrative antibody or $V_L$ sequence provided herein. In some aspects, the CDR-L2 sequence is a CDR-L2 sequence of an scFv-Fc sequence provided in SEQ ID NO: 169. In some aspects, the CDR-L2 sequence is a CDR-L2 sequence of a $V_L$ sequence provided in SEQ ID NOs.: 151-158.

In some embodiments, the antibody comprises a $V_L$ sequence comprising a CDR-L2 sequence comprising, consisting of, or consisting essentially of a sequence selected from SEQ ID NOs: 116-122. In some aspects, the antibody comprises a $V_L$ sequence comprising a CDR-L2 sequence comprising, consisting of, or consisting essentially of SEQ ID NO: 116. In some aspects, the antibody comprises a $V_L$ sequence comprising a CDR-L2 sequence comprising, consisting of, or consisting essentially of SEQ ID NO: 117. In some aspects, the antibody comprises a $V_L$ sequence comprising a CDR-L2 sequence comprising, consisting of, or consisting essentially of SEQ ID NO: 118. In some aspects, the antibody comprises a $V_L$ sequence comprising a CDR-L2 sequence comprising, consisting of, or consisting essentially of SEQ ID NO: 119. In some aspects, the antibody comprises a $V_L$ sequence comprising a CDR-L2 sequence comprising, consisting of, or consisting essentially of SEQ ID NO: 120. In some aspects, the antibody comprises a $V_L$ sequence comprising a CDR-L2 sequence comprising, consisting of, or consisting essentially of SEQ ID NO: 121. In some aspects, the antibody comprises a $V_L$ sequence comprising a CDR-L2 sequence comprising, consisting of, or consisting essentially of SEQ ID NO: 122.

2.5.3. CDR-L1

In some embodiments, the antibody comprises a $V_L$ sequence comprising a CDR-L1 sequence, wherein the CDR-L1 sequence comprises, consists of, or consists essentially of a CDR-L1 sequence of an illustrative antibody or $V_L$ sequence provided herein. In some aspects, the CDR-L1 sequence is a CDR-L1 sequence of an scFv-Fc sequence provided in SEQ ID NO: 169. In some aspects, the CDR-L1 sequence is a CDR-L1 sequence of a $V_L$ sequence provided in SEQ ID NOs.: 151-158.

In some embodiments, the antibody comprises a $V_L$ sequence comprising a CDR-L1 sequence comprising, consisting of, or consisting essentially of a sequence selected from SEQ ID NOs: 109-115. In some aspects, the antibody comprises a $V_L$ sequence comprising a CDR-L1 sequence comprising, consisting of, or consisting essentially of SEQ ID NO: 109. In some aspects, the antibody comprises a $V_L$ sequence comprising a CDR-L1 sequence comprising, consisting of, or consisting essentially of SEQ ID NO: 110. In some aspects, the antibody comprises a $V_L$ sequence comprising a CDR-L1 sequence comprising, consisting of, or consisting essentially of SEQ ID NO: 111. In some aspects, the antibody comprises a $V_L$ sequence comprising a CDR-L1 sequence comprising, consisting of, or consisting essentially of SEQ ID NO: 112. In some aspects, the antibody comprises a $V_L$ sequence comprising a CDR-L1 sequence comprising, consisting of, or consisting essentially of SEQ ID NO: 113. In some aspects, the antibody comprises a $V_L$ sequence comprising a CDR-L1 sequence comprising, consisting of, or consisting essentially of SEQ ID NO: 114. In some aspects, the antibody comprises a $V_L$ sequence comprising a CDR-L1 sequence comprising, consisting of, or consisting essentially of SEQ ID NO: 115.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 123-129 and a CDR-L2 sequence comprising, consisting of, or consisting essentially of a sequence selected from SEQ ID NOs: 116-122. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 151-158.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 123-129 and a CDR-L1 sequence comprising, consisting of, or consisting essentially of a sequence selected from SEQ ID NOs: 109-115. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 151-158.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 109-115 and a CDR-L2 sequence comprising, consisting of, or consisting essentially of a sequence selected from SEQ ID NOs: 116-122. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 151-158.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 109-115, a CDR-L2 sequence comprising, consisting of, or consisting essentially of a sequence selected from SEQ ID NOs: 116-122, and a CDR-L3 sequence comprising, consisting of, or consisting essentially of a sequence selected from SEQ ID NOs: 123-129. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 151-158.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.6. $V_L$ Sequences

In some embodiments, the antibody comprises, consists of, or consists essentially of a $V_L$ sequence of an scFv-Fc sequence provided in SEQ ID NO: 169. In some embodiments, the antibody comprises, consists of, or consists essentially of a $V_L$ sequence provided in SEQ ID NOs.: 151-158.

In some embodiments, the antibody comprises a $V_L$ sequence comprising, consisting of, or consisting essentially of a sequence selected from SEQ ID NOs: 151-157. In some aspects, the antibody comprises a $V_L$ sequence comprising, consisting of, or consisting essentially of SEQ ID NO: 151. In some aspects, the antibody comprises a $V_L$ sequence comprising, consisting of, or consisting essentially of SEQ ID NO: 152. In some aspects, the antibody comprises a $V_L$ sequence comprising, consisting of, or consisting essentially of SEQ ID NO: 153. In some aspects, the antibody comprises a $V_L$ sequence comprising, consisting of, or consisting essentially of SEQ ID NO: 154. In some aspects, the antibody comprises a $V_L$ sequence comprising, consisting of, or consisting essentially of SEQ ID NO: 155. In some aspects, the antibody comprises a $V_L$ sequence comprising, consisting of, or consisting essentially of SEQ ID NO: 156. In some aspects, the antibody comprises a $V_L$ sequence comprising, consisting of, or consisting essentially of SEQ ID NO: 157. In some aspects, the antibody comprises a $V_L$ sequence comprising, consisting of, or consisting essentially of SEQ ID NO: 158.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 88-108, and the CDR-L3 sequence is a CDR-L3 sequence comprising, consisting of, or consisting essentially of SEQ ID NOs: 123-129.

In some aspects, the CDR-H3-CDR-L3 pairs are selected from SEQ ID NO: 123 and SEQ ID NO: 88; SEQ ID NO: 123 and SEQ ID NO: 89; SEQ ID NO: 123 and SEQ ID NO: 90; SEQ ID NO: 123 and SEQ ID NO: 91; SEQ ID NO: 123 and SEQ ID NO: 92; SEQ ID NO: 123 and SEQ ID NO: 93; SEQ ID NO: 123 and SEQ ID NO: 94; SEQ ID NO: 123 and SEQ ID NO: 95; SEQ ID NO: 123 and SEQ ID NO: 96; SEQ ID NO: 123 and SEQ ID NO: 97; SEQ ID NO: 123 and SEQ ID NO: 98; SEQ ID NO: 123 and SEQ ID NO: 99; SEQ ID NO: 123 and SEQ ID NO: 100; SEQ ID NO: 123 and SEQ ID NO: 101; SEQ ID NO: 123 and SEQ ID NO: 102; SEQ ID NO: 123 and SEQ ID NO: 103; SEQ ID NO: 123 and SEQ ID NO: 104; SEQ ID NO: 123 and SEQ ID NO: 105; SEQ ID NO: 123 and SEQ ID NO: 106; SEQ ID NO: 123 and SEQ ID NO: 107; and SEQ ID NO: 123 and SEQ ID NO: 108.

In some aspects, the CDR-H3-CDR-L3 pairs are selected from SEQ ID NO: 124 and SEQ ID NO: 88; SEQ ID NO: 124 and SEQ ID NO: 89; SEQ ID NO: 124 and SEQ ID NO: 90; SEQ ID NO: 124 and SEQ ID NO: 91; SEQ ID NO: 124 and SEQ ID NO: 92; SEQ ID NO: 124 and SEQ ID NO: 93; SEQ ID NO: 124 and SEQ ID NO: 94; SEQ ID NO: 124 and SEQ ID NO: 95; SEQ ID NO: 124 and SEQ ID NO: 96; SEQ ID NO: 124 and SEQ ID NO: 97; SEQ ID NO: 124 and SEQ ID NO: 98; SEQ ID NO: 124 and SEQ ID NO: 99; SEQ ID NO: 124 and SEQ ID NO: 100; SEQ ID NO: 124 and SEQ ID NO: 101; SEQ ID NO: 124 and SEQ ID NO: 102; SEQ ID NO: 124 and SEQ ID NO: 103; SEQ ID NO: 124 and SEQ ID NO: 104; SEQ ID NO: 124 and SEQ ID NO: 105; SEQ ID NO: 124 and SEQ ID NO: 106; SEQ ID NO: 124 and SEQ ID NO: 107; and SEQ ID NO: 124 and SEQ ID NO: 108.

In some aspects, the CDR-H3-CDR-L3 pairs are selected from SEQ ID NO: 125 and SEQ ID NO: 88; SEQ ID NO: 125 and SEQ ID NO: 89; SEQ ID NO: 125 and SEQ ID NO: 90; SEQ ID NO: 125 and SEQ ID NO: 91; SEQ ID NO: 125 and SEQ ID NO: 92; SEQ ID NO: 125 and SEQ ID NO: 93; SEQ ID NO: 125 and SEQ ID NO: 94; SEQ ID NO: 125 and SEQ ID NO: 95; SEQ ID NO: 125 and SEQ ID NO: 96; SEQ ID NO: 125 and SEQ ID NO: 97; SEQ ID NO: 125 and SEQ ID NO: 98; SEQ ID NO: 125 and SEQ ID NO: 99; SEQ ID NO: 125 and SEQ ID NO: 100; SEQ ID NO: 125 and SEQ ID NO: 101; SEQ ID NO: 125 and SEQ ID NO: 102; SEQ ID NO: 125 and SEQ ID NO: 103; SEQ ID NO: 125 and SEQ ID NO: 104; SEQ ID NO: 125 and SEQ ID NO: 105; SEQ ID NO: 125 and SEQ ID NO: 106; SEQ ID NO: 125 and SEQ ID NO: 107; and SEQ ID NO: 125 and SEQ ID NO: 108.

In some aspects, the CDR-H3-CDR-L3 pairs are selected from SEQ ID NO: 126 and SEQ ID NO: 88; SEQ ID NO: 126 and SEQ ID NO: 89; SEQ ID NO: 126 and SEQ ID NO:

90; SEQ ID NO: 126 and SEQ ID NO: 91; SEQ ID NO: 126 and SEQ ID NO: 92; SEQ ID NO: 126 and SEQ ID NO: 93; SEQ ID NO: 126 and SEQ ID NO: 94; SEQ ID NO: 126 and SEQ ID NO: 95; SEQ ID NO: 126 and SEQ ID NO: 96; SEQ ID NO: 126 and SEQ ID NO: 97; SEQ ID NO: 126 and SEQ ID NO: 98; SEQ ID NO: 126 and SEQ ID NO: 99; SEQ ID NO: 126 and SEQ ID NO: 100; SEQ ID NO: 126 and SEQ ID NO: 101; SEQ ID NO: 126 and SEQ ID NO: 102; SEQ ID NO: 126 and SEQ ID NO: 103; SEQ ID NO: 126 and SEQ ID NO: 104; SEQ ID NO: 126 and SEQ ID NO: 105; SEQ ID NO: 126 and SEQ ID NO: 106; SEQ ID NO: 126 and SEQ ID NO: 107; and SEQ ID NO: 126 and SEQ ID NO: 108.

In some aspects, the CDR-H3-CDR-L3 pairs are selected from SEQ ID NO: 127 and SEQ ID NO: 88; SEQ ID NO: 127 and SEQ ID NO: 89; SEQ ID NO: 127 and SEQ ID NO: 90; SEQ ID NO: 127 and SEQ ID NO: 91; SEQ ID NO: 127 and SEQ ID NO: 92; SEQ ID NO: 127 and SEQ ID NO: 93; SEQ ID NO: 127 and SEQ ID NO: 94; SEQ ID NO: 127 and SEQ ID NO: 95; SEQ ID NO: 127 and SEQ ID NO: 96; SEQ ID NO: 127 and SEQ ID NO: 97; SEQ ID NO: 127 and SEQ ID NO: 98; SEQ ID NO: 127 and SEQ ID NO: 99; SEQ ID NO: 127 and SEQ ID NO: 100; SEQ ID NO: 127 and SEQ ID NO: 101; SEQ ID NO: 127 and SEQ ID NO: 102; SEQ ID NO: 127 and SEQ ID NO: 103; SEQ ID NO: 127 and SEQ ID NO: 104; SEQ ID NO: 127 and SEQ ID NO: 105; SEQ ID NO: 127 and SEQ ID NO: 106; SEQ ID NO: 127 and SEQ ID NO: 107; and SEQ ID NO: 127 and SEQ ID NO: 108.

In some aspects, the CDR-H3-CDR-L3 pairs are selected from SEQ ID NO: 128 and SEQ ID NO: 88; SEQ ID NO: 128 and SEQ ID NO: 89; SEQ ID NO: 128 and SEQ ID NO: 90; SEQ ID NO: 128 and SEQ ID NO: 91; SEQ ID NO: 128 and SEQ ID NO: 92; SEQ ID NO: 128 and SEQ ID NO: 93; SEQ ID NO: 128 and SEQ ID NO: 94; SEQ ID NO: 128 and SEQ ID NO: 95; SEQ ID NO: 128 and SEQ ID NO: 96; SEQ ID NO: 128 and SEQ ID NO: 97; SEQ ID NO: 128 and SEQ ID NO: 98; SEQ ID NO: 128 and SEQ ID NO: 99; SEQ ID NO: 128 and SEQ ID NO: 100; SEQ ID NO: 128 and SEQ ID NO: 101; SEQ ID NO: 128 and SEQ ID NO: 102; SEQ ID NO: 128 and SEQ ID NO: 103; SEQ ID NO: 128 and SEQ ID NO: 104; SEQ ID NO: 128 and SEQ ID NO: 105; SEQ ID NO: 128 and SEQ ID NO: 106; SEQ ID NO: 128 and SEQ ID NO: 107; and SEQ ID NO: 128 and SEQ ID NO: 108.

In some aspects, the CDR-H3-CDR-L3 pairs are selected from SEQ ID NO: 129 and SEQ ID NO: 88; SEQ ID NO: 129 and SEQ ID NO: 89; SEQ ID NO: 129 and SEQ ID NO: 90; SEQ ID NO: 129 and SEQ ID NO: 91; SEQ ID NO: 129 and SEQ ID NO: 92; SEQ ID NO: 129 and SEQ ID NO: 93; SEQ ID NO: 129 and SEQ ID NO: 94; SEQ ID NO: 129 and SEQ ID NO: 95; SEQ ID NO: 129 and SEQ ID NO: 96; SEQ ID NO: 129 and SEQ ID NO: 97; SEQ ID NO: 129 and SEQ ID NO: 98; SEQ ID NO: 129 and SEQ ID NO: 99; SEQ ID NO: 129 and SEQ ID NO: 100; SEQ ID NO: 129 and SEQ ID NO: 101; SEQ ID NO: 129 and SEQ ID NO: 102; SEQ ID NO: 129 and SEQ ID NO: 103; SEQ ID NO: 129 and SEQ ID NO: 104; SEQ ID NO: 129 and SEQ ID NO: 105; SEQ ID NO: 129 and SEQ ID NO: 106; SEQ ID NO: 129 and SEQ ID NO: 107; and SEQ ID NO: 129 and SEQ ID NO: 108.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.2. CDR-H1-CDR-L1 Pairs

In some embodiments, the antibody comprises a CDR-H1 sequence and a CDR-L1 sequence. In some aspects, the CDR-H1 sequence is part of a $V_H$ and the CDR-L1 sequence is part of a $V_L$.

In some aspects, the CDR-H1 sequence is a Chothia CDR-H1 sequence comprising, consisting of, or consisting essentially of SEQ ID NOs: 4-24, and the CDR-L1 sequence is a CDR-L1 sequence comprising, consisting of, or consisting essentially of SEQ ID NOs: 109-115.

In some aspects, the CDR-H1 sequence is a Kabat CDR-H1 sequence comprising, consisting of, or consisting essentially of SEQ ID NOs: 25-45, and the CDR-L1 sequence is a CDR-L1 sequence comprising, consisting of, or consisting essentially of SEQ ID NOs: 109-115.

2.7.2.1. Variants of CDR-H1-CDR-L1 Pairs

In some embodiments, the CDR-H1CDR-L1 pairs provided herein comprise a variant of an illustrative CDR-H1 and/or CDR-L1 sequence provided in this disclosure.

In some aspects, the CDR-H1 sequence comprises, consists of, or consists essentially of a variant of an illustrative CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative CDR-H1 sequences provided in this disclosure. In some aspects, the CDR-H1 sequence comprises, consists of, or consists essentially of any of the illustrative CDR-H1 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.7.3. CDR-H2-CDR-L2 Pairs

In some embodiments, the antibody comprises a CDR-H2 sequence and a CDR-L2 sequence. In some aspects, the CDR-H2 sequence is part of a $V_H$ and the CDR-L2 sequence is part of a $V_L$.

In some aspects, the CDR-H2 sequence is a Chothia CDR-H2 sequence comprising, consisting of, or consisting essentially of SEQ ID NOs: 46-66, and the CDR-L2 sequence is a CDR-L2 sequence comprising, consisting of, or consisting essentially of SEQ ID NOs: 116-122.

In some aspects, the CDR-H1 sequence is a Kabat CDR-H2 sequence comprising, consisting of, or consisting essentially of SEQ ID NOs: 67-87, and the CDR-L2 sequence is a CDR-L2 sequence comprising, consisting of, or consisting essentially of SEQ ID NOs: 116-122.

2.7.3.1. Variants of CDR-H2-CDR-L2 Pairs

In some embodiments, the CDR-H2-CDR-L2 pairs provided herein comprise a variant of an illustrative CDR-H2 and/or CDR-L2 sequence provided in this disclosure.

In some aspects, the CDR-H2 sequence comprises, consists of, or consists essentially of a variant of an illustrative CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative CDR-H2 sequences provided in this disclosure. In some aspects, the CDR-H2 sequence comprises, consists of, or consists essentially of any of the illustrative CDR-H2 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

2.7.4. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 130-150, and the $V_L$ sequence is a $V_L$ sequence comprising, consisting of, or consisting essentially of SEQ ID NOs: 151-158.

In some aspects, the $V_H$-$V_L$ pairs are selected from SEQ ID NO: 151 and SEQ ID NO: 130; SEQ ID NO: 151 and SEQ ID NO: 131; SEQ ID NO: 151 and SEQ ID NO: 132; SEQ ID NO: 151 and SEQ ID NO: 133; SEQ ID NO: 151 and SEQ ID NO: 134; SEQ ID NO: 151 and SEQ ID NO: 135; SEQ ID NO: 151 and SEQ ID NO: 136; SEQ ID NO: 151 and SEQ ID NO: 137; SEQ ID NO: 151 and SEQ ID NO: 138; SEQ ID NO: 151 and SEQ ID NO: 139; SEQ ID NO: 151 and SEQ ID NO: 140; SEQ ID NO: 151 and SEQ ID NO: 141; SEQ ID NO: 151 and SEQ ID NO: 142; SEQ ID NO: 151 and SEQ ID NO: 143; SEQ ID NO: 151 and SEQ ID NO: 144; SEQ ID NO: 151 and SEQ ID NO: 145; SEQ ID NO: 151 and SEQ ID NO: 146; SEQ ID NO: 151 and SEQ ID NO: 147; SEQ ID NO: 151 and SEQ ID NO: 148; SEQ ID NO: 151 and SEQ ID NO: 149; and SEQ ID NO: 151 and SEQ ID NO: 150.

In some aspects, the $V_H$-$V_L$ pairs are selected from SEQ ID NO: 152 and SEQ ID NO: 130; SEQ ID NO: 152 and SEQ ID NO: 131; SEQ ID NO: 152 and SEQ ID NO: 132; SEQ ID NO: 152 and SEQ ID NO: 133; SEQ ID NO: 152 and SEQ ID NO: 134; SEQ ID NO: 152 and SEQ ID NO: 135; SEQ ID NO: 152 and SEQ ID NO: 136; SEQ ID NO: 152 and SEQ ID NO: 137; SEQ ID NO: 152 and SEQ ID NO: 138; SEQ ID NO: 152 and SEQ ID NO: 139; SEQ ID NO: 152 and SEQ ID NO: 140; SEQ ID NO: 152 and SEQ ID NO: 141; SEQ ID NO: 152 and SEQ ID NO: 142; SEQ ID NO: 152 and SEQ ID NO: 143; SEQ ID NO: 152 and SEQ ID NO: 144; SEQ ID NO: 152 and SEQ ID NO: 145; SEQ ID NO: 152 and SEQ ID NO: 146; SEQ ID NO: 152 and SEQ ID NO: 147; SEQ ID NO: 152 and SEQ ID NO: 148; SEQ ID NO: 152 and SEQ ID NO: 149; and SEQ ID NO: 152 and SEQ ID NO: 150.

In some aspects, the $V_H$-$V_L$ pairs are selected from SEQ ID NO: 153 and SEQ ID NO: 130; SEQ ID NO: 153 and SEQ ID NO: 131; SEQ ID NO: 153 and SEQ ID NO: 132; SEQ ID NO: 153 and SEQ ID NO: 133; SEQ ID NO: 153 and SEQ ID NO: 134; SEQ ID NO: 153 and SEQ ID NO: 135; SEQ ID NO: 153 and SEQ ID NO: 136; SEQ ID NO: 153 and SEQ ID NO: 137; SEQ ID NO: 153 and SEQ ID NO: 138; SEQ ID NO: 153 and SEQ ID NO: 139; SEQ ID NO: 153 and SEQ ID NO: 140; SEQ ID NO: 153 and SEQ ID NO: 141; SEQ ID NO: 153 and SEQ ID NO: 142; SEQ ID NO: 153 and SEQ ID NO: 143; SEQ ID NO: 153 and SEQ ID NO: 144; SEQ ID NO: 153 and SEQ ID NO: 145; SEQ ID NO: 153 and SEQ ID NO: 146; SEQ ID NO: 153 and SEQ ID NO: 147; SEQ ID NO: 153 and SEQ ID NO: 148; SEQ ID NO: 153 and SEQ ID NO: 149; and SEQ ID NO: 153 and SEQ ID NO: 150.

In some aspects, the $V_H$-$V_L$ pairs are selected from SEQ ID NO: 154 and SEQ ID NO: 130; SEQ ID NO: 154 and SEQ ID NO: 131; SEQ ID NO: 154 and SEQ ID NO: 132; SEQ ID NO: 154 and SEQ ID NO: 133; SEQ ID NO: 154 and SEQ ID NO: 134; SEQ ID NO: 154 and SEQ ID NO: 135; SEQ ID NO: 154 and SEQ ID NO: 136; SEQ ID NO: 154 and SEQ ID NO: 137; SEQ ID NO: 154 and SEQ ID NO: 138; SEQ ID NO: 154 and SEQ ID NO: 139; SEQ ID NO: 154 and SEQ ID NO: 140; SEQ ID NO: 154 and SEQ ID NO: 141; SEQ ID NO: 154 and SEQ ID NO: 142; SEQ ID NO: 154 and SEQ ID NO: 143; SEQ ID NO: 154 and SEQ ID NO: 144; SEQ ID NO: 154 and SEQ ID NO: 145; SEQ ID NO: 154 and SEQ ID NO: 146; SEQ ID NO: 154 and SEQ ID NO: 147; SEQ ID NO: 154 and SEQ ID NO: 148; SEQ ID NO: 154 and SEQ ID NO: 149; and SEQ ID NO: 154 and SEQ ID NO: 150.

In some aspects, the $V_H$-$V_L$ pairs are selected from SEQ ID NO: 155 and SEQ ID NO: 130; SEQ ID NO: 155 and SEQ ID NO: 131; SEQ ID NO: 155 and SEQ ID NO: 132; SEQ ID NO: 155 and SEQ ID NO: 133; SEQ ID NO: 155 and SEQ ID NO: 134; SEQ ID NO: 155 and SEQ ID NO: 135; SEQ ID NO: 155 and SEQ ID NO: 136; SEQ ID NO: 155 and SEQ ID NO: 137; SEQ ID NO: 155 and SEQ ID NO: 138; SEQ ID NO: 155 and SEQ ID NO: 139; SEQ ID NO: 155 and SEQ ID NO: 140; SEQ ID NO: 155 and SEQ ID NO: 141; SEQ ID NO: 155 and SEQ ID NO: 142; SEQ ID NO: 155 and SEQ ID NO: 143; SEQ ID NO: 155 and SEQ ID NO: 144; SEQ ID NO: 155 and SEQ ID NO: 145; SEQ ID NO: 155 and SEQ ID NO: 146; SEQ ID NO: 155 and SEQ ID NO: 147; SEQ ID NO: 155 and SEQ ID NO: 148; SEQ ID NO: 155 and SEQ ID NO: 149; and SEQ ID NO: 155 and SEQ ID NO: 150.

In some aspects, the $V_H$-$V_L$ pairs are selected from SEQ ID NO: 156 and SEQ ID NO: 130; SEQ ID NO: 156 and SEQ ID NO: 131; SEQ ID NO: 156 and SEQ ID NO: 132;

SEQ ID NO: 156 and SEQ ID NO: 133; SEQ ID NO: 156 and SEQ ID NO: 134; SEQ ID NO: 156 and SEQ ID NO: 135; SEQ ID NO: 156 and SEQ ID NO: 136; SEQ ID NO: 156 and SEQ ID NO: 137; SEQ ID NO: 156 and SEQ ID NO: 138; SEQ ID NO: 156 and SEQ ID NO: 139; SEQ ID NO: 156 and SEQ ID NO: 140; SEQ ID NO: 156 and SEQ ID NO: 141; SEQ ID NO: 156 and SEQ ID NO: 142; SEQ ID NO: 156 and SEQ ID NO: 143; SEQ ID NO: 156 and SEQ ID NO: 144; SEQ ID NO: 156 and SEQ ID NO: 145; SEQ ID NO: 156 and SEQ ID NO: 146; SEQ ID NO: 156 and SEQ ID NO: 147; SEQ ID NO: 156 and SEQ ID NO: 148; SEQ ID NO: 156 and SEQ ID NO: 149; and SEQ ID NO: 156 and SEQ ID NO: 150.

In some aspects, the $V_H$-$V_L$ pairs are selected from SEQ ID NO: 157 and SEQ ID NO: 130; SEQ ID NO: 157 and SEQ ID NO: 131; SEQ ID NO: 157 and SEQ ID NO: 132; SEQ ID NO: 157 and SEQ ID NO: 133; SEQ ID NO: 157 and SEQ ID NO: 134; SEQ ID NO: 157 and SEQ ID NO: 135; SEQ ID NO: 157 and SEQ ID NO: 136; SEQ ID NO: 157 and SEQ ID NO: 137; SEQ ID NO: 157 and SEQ ID NO: 138; SEQ ID NO: 157 and SEQ ID NO: 139; SEQ ID NO: 157 and SEQ ID NO: 140; SEQ ID NO: 157 and SEQ ID NO: 141; SEQ ID NO: 157 and SEQ ID NO: 142; SEQ ID NO: 157 and SEQ ID NO: 143; SEQ ID NO: 157 and SEQ ID NO: 144; SEQ ID NO: 157 and SEQ ID NO: 145; SEQ ID NO: 157 and SEQ ID NO: 146; SEQ ID NO: 157 and SEQ ID NO: 147; SEQ ID NO: 157 and SEQ ID NO: 148; SEQ ID NO: 157 and SEQ ID NO: 149; and SEQ ID NO: 157 and SEQ ID NO: 150.

In some aspects, the $V_H$-$V_L$ pairs are selected from SEQ ID NO: 158 and SEQ ID NO: 130; SEQ ID NO: 158 and SEQ ID NO: 131; SEQ ID NO: 158 and SEQ ID NO: 132; SEQ ID NO: 158 and SEQ ID NO: 133; SEQ ID NO: 158 and SEQ ID NO: 134; SEQ ID NO: 158 and SEQ ID NO: 135; SEQ ID NO: 158 and SEQ ID NO: 136; SEQ ID NO: 158 and SEQ ID NO: 137; SEQ ID NO: 158 and SEQ ID NO: 138; SEQ ID NO: 158 and SEQ ID NO: 139; SEQ ID NO: 158 and SEQ ID NO: 140; SEQ ID NO: 158 and SEQ ID NO: 141; SEQ ID NO: 158 and SEQ ID NO: 142; SEQ ID NO: 158 and SEQ ID NO: 143; SEQ ID NO: 158 and SEQ ID NO: 144; SEQ ID NO: 158 and SEQ ID NO: 145; SEQ ID NO: 158 and SEQ ID NO: 146; SEQ ID NO: 158 and SEQ ID NO: 147; SEQ ID NO: 158 and SEQ ID NO: 148; SEQ ID NO: 158 and SEQ ID NO: 149; and SEQ ID NO: 158 and SEQ ID NO: 150.

2.7.4.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.8. Antibodies Comprising all Six CDRs

In some embodiments, the antibody comprises a CDR-H1 sequence, a CDR-H2 sequence, a CDR-H3 sequence, a CDR-L1 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 4-24; the CDR-H2 sequence is a Chothia CDR-H2 sequence comprising, consisting of, or consisting essentially of SEQ ID NOs: 46-66; the CDR-H3 sequence is a CDR-H3 sequence comprising, consisting of, or consisting essentially of SEQ ID NOs: 88-108; the CDR-L1 sequence is a CDR-L1 sequence comprising, consisting of, or consisting essentially of SEQ ID NOs: 109-115; the CDR-L2 sequence is a CDR-L2 sequence comprising, consisting of, or consisting essentially of SEQ ID NOs: 116-122; and the CDR-L3 sequence is a CDR-L3 sequence comprising, consisting of, or consisting essentially of SEQ ID NOs: 123-129.

In some aspects, the CDR-H1 sequence is a Kabat CDR-H1 sequence comprising, consisting of, or consisting essentially of SEQ ID NOs: 25-45; the CDR-H2 sequence is a Kabat CDR-H2 sequence comprising, consisting of, or consisting essentially of SEQ ID NOs: 67-87; the CDR-H3 sequence is a CDR-H3 sequence comprising, consisting of, or consisting essentially of SEQ ID NOs: 88-108; the CDR-L1 sequence is a CDR-L1 sequence comprising, consisting of, or consisting essentially of SEQ ID NOs: 109-115; the CDR-L2 sequence is a CDR-L2 sequence comprising, consisting of, or consisting essentially of SEQ ID NOs: 116-122; and the CDR-L3 sequence is a CDR-L3 sequence comprising, consisting of, or consisting essentially of SEQ ID NOs: 123-129.

2.8.1. Variants of Antibodies Comprising all Six CDRs

In some embodiments, the CDR-H1, CDR-H2, CDR-H3, CDR-L1, CDR-L2, and CDR-L3 provided herein comprise a variant of an illustrative CDR-H1, CDR-H2, CDR-H3, CDR-L1, CDR-L2, and/or CDR-L3 sequence provided in this disclosure.

In some aspects, the CDR-H1 sequence comprises, consists of, or consists essentially of a variant of an illustrative Chothia or Kabat CDR-H1 sequence provided in this disclosure. In some aspects, the CDR-H1 sequence comprises, consists of, or consists essentially of a sequence having at least 70%, 75%, 80%, 85%, 90%, or 95% identity with any of the illustrative Chothia or Kabat CDR-H1 sequences provided in this disclosure. In some aspects, the CDR-H1 sequence comprises, consists of, or consists essentially of any of the illustrative Chothia or Kabat CDR-H1 sequences provided in this disclosure, with 1, 2, or 3 amino acid substitutions. In some aspects, the amino acid substitutions are conservative amino acid substitutions.

In some aspects, the CDR-H2 sequence comprises, consists of, or consists essentially of a variant of an illustrative Chothia or Kabat CDR-H2 sequence provided in this disclosure. In some aspects, the CDR-H2 sequence comprises, consists of, or consists essentially of a sequence having at least 70%, 75%, 80%, 85%, 90%, or 95% identity with any of the illustrative Chothia or Kabat CDR-H2 sequences provided in this disclosure. In some aspects, the CDR-H2 sequence comprises, consists of, or consists essentially of any of the illustrative Chothia or Kabat CDR-H2 sequences provided in this disclosure, with 1, 2, or 3 amino acid substitutions. In some aspects, the amino acid substitutions are conservative amino acid substitutions.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.9. Consensus Sequences

In some embodiments, provided herein are anti-Tim-3 antibodies comprising one or more sequences defined by consensus sequences. Each consensus sequence is based, at least in part, on one or more alignments of two or more useful anti-Tim-3 CDR sequences provided in this disclosure. Based on such alignments, a person of skill in the art would recognize that different amino acid residues may useful in certain positions of the CDRs. Accordingly, each consensus sequence encompasses two or more useful anti-Tim-3 CDR sequences.

In some embodiments, the antibodies comprise one to six of the consensus CDR sequences provided herein. In some embodiments, the antibodies comprise two to six of the consensus CDR sequences provided herein. In some embodiments, the antibodies comprise three to six of the consensus CDR sequences provided herein. In some embodiments, the antibodies comprise four to six of the consensus CDR sequences provided herein. In some embodiments, the antibodies comprise five to six of the consensus CDR sequences provided herein. In some embodiments, the antibodies comprise six of the consensus CDR sequences provided herein. In some embodiments, the antibodies comprise a $V_L$ comprising the CDR-L consensus sequence(s). In some embodiments, the antibodies comprise a $V_H$ comprising the CDR-H consensus sequence(s). In some embodiments, the antibodies comprise a $V_H$ comprising the CDR-H consensus sequence(s) and a $V_L$ comprising the CDR-L consensus sequence(s).

2.9.1. CDR-H3 Consensus Sequences

In some embodiments, the antibody comprises a CDR-H3 sequence defined by the consensus sequence $\alpha_1$-$\alpha_2$-$\alpha_3$-Y-R-$\alpha_6$-$\alpha_7$-$\alpha_8$-$\alpha_9$-$\alpha_{10}$-$\alpha_{11}$-$\alpha_{12}$-$\alpha_{13}$, where $\alpha_1$ is Q, S or G; $\alpha_2$ is G, F, Y, or H; $\alpha_3$ is G, F, V, or I; $\alpha_6$ is absent or S; $\alpha_7$ is Y, S, M, or L; $\alpha_8$ is D, N, or W; $\alpha_9$ is D; $\alpha_{10}$ is A, W, or S; $\alpha_7$ is M, Y, F, or L; $\alpha_{11}$ is D or V; and $\alpha_{13}$ is Y or H.

In some embodiments, the antibody comprises a CDR-H3 sequence defined by the consensus sequence G-$\beta_2$-$\beta_3$-Y-R-$\beta_7$-W-D-S-$\beta_{11}$-D-$\beta_{13}$ (SEQ ID NO: 170), where $\beta_2$ is Y or H; $\beta_3$ is V or I; $\beta_7$ is M, or L; $\beta_{11}$ is Y, F, or L; and $\beta_{13}$ is Y or H.

2.9.2. Chothia CDR-H1 Consensus Sequences

In some embodiments, the antibody comprises a Chothia CDR-H1 sequence defined by the consensus sequence G-$\gamma_2$-$\gamma_3$-$\gamma_4$-$\gamma_5$-$\gamma_6$-$\gamma_7$, where $\gamma_2$ is F or Y; $\gamma_3$ is S, P or N; $\gamma_4$ is L, F, or I; $\gamma_5$ is T, I, S, G, or R; $\gamma_6$ is S, G, R, N, or K; and $\gamma_7$ is N, Y or H.

In some embodiments, the antibody comprises a Chothia CDR-H1 sequence defined by the consensus sequence G-F-N-I-$\delta_5$-$\delta_6$-$\delta_7$ (SEQ ID NO: 171), where $\delta_5$ is T, I, S, G, or R; $\delta_6$ is S, R, N, K, or G; and $\delta_7$ is N, Y or H.

2.9.3. Chothia CDR-H2 Consensus Sequences

In some embodiments, the antibody comprises a Chothia CDR-H2 sequence defined by the consensus sequence $\epsilon_1$-$\epsilon_2$-$\epsilon_3$-$\epsilon_4$-G-$\epsilon_6$, where $\epsilon_1$ is W, N, T, V, I, S, A, or M; $\epsilon_2$ is S or P; $\epsilon_3$ is absent, Y, V, G, D, N, T, or A; $\epsilon_4$ is D, G, N, R, Q, A, or V; and $\epsilon_6$ is Y, I, D, S, or F.

In some embodiments, the antibody comprises a Chothia CDR-H2 sequence defined by the consensus sequence $\epsilon_1$-P-$\epsilon_3$-$\epsilon_4$-G-$\epsilon_6$, where $\epsilon_1$ is T, V, I, S, A, or M; $\epsilon_3$ is V, G, D, N, T, or A; and $\epsilon_4$ is G, R, Q, A, or V; and $\epsilon_6$ is Y, I, D, S, or F.

2.9.4. Kabat CDR-H1 Consensus Sequences

In some embodiments, the antibody comprises a Kabat CDR-H1 sequence defined by the consensus sequence $\zeta_1$-$\zeta_2$-$\zeta_3$-$\zeta_4$-$\zeta_5$, where $\zeta_1$ is S, G, R, N, or K; $\zeta_2$ is Y, H, or N; $\zeta_3$ is G, T, Y, A, or V; $\zeta_4$ is V, M, or I; and $\zeta_5$ is N or H.

In some embodiments, the antibody comprises a Kabat CDR-H1 sequence defined by the consensus sequence $\eta_1$-$\eta_2$-$\eta_3$-I-H, where $\eta_1$ is G, R, N, or S; $\eta_2$ is Y, H, or N; and $\eta_3$ is Y, A, or V.

2.9.5. Kabat CDR-H2 Consensus Sequences

In some embodiments, the antibody comprises a Kabat CDR-H2 sequence defined by the consensus sequence $\theta_1$-I-$\theta_3$-$\theta_4$-$\theta_5$-$\theta_6$-$\theta_7$-$\theta_8$-T-$\theta_{10}$-$\theta_{11}$-$\theta_{12}$-$\theta_{13}$-$\theta_{14}$-$\theta_{15}$-$\theta_{16}$-$\theta_{17}$, where $\theta_1$ is V, L, G, D, or A; $\theta_3$ is W, N, T, V, I, S, A, or M; $\theta_4$ is S or P; $\theta_5$ is absent, Y, V, G, D, N, T, or A; $\theta_6$ is D, N, R, Q, G, A, or V; $\theta_7$ is G; $\theta_8$ is I, Y, D, S, or F; $\theta_{10}$ is T, E, D, or G; $\theta_{11}$ is Y; $\theta_{12}$ is N, or A; $\theta_{13}$ is P, Q, S, or D; $\theta_{14}$ is A, K, or S; $\theta_{15}$ is L, F, or V; $\theta_{16}$ is Q or K; and $\theta_{17}$ is S, G or D.

In some embodiments, the antibody comprises a Kabat CDR-H2 sequence defined by the consensus sequence V-I-W-S-D-G-S-T-T-Y-N-$\theta_{13}$-$\theta_{14}$-$\theta_{15}$-$\theta_{16}$-$\theta_{17}$ (SEQ ID NO: 172), where $\theta_{13}$ is P, Q, S, or D; $\theta_{14}$ is S, K, or A; $\theta_{15}$ is F, L, or V; $\theta_{16}$ is Q or K; $\theta_{17}$ is G or S.

In some embodiments, the antibody comprises a Kabat CDR-H2 sequence defined by the consensus sequence $\theta_1$-I-$\theta_3$-P-$\theta_5$-$\theta_6$-G-$\theta_8$-T-$\theta_{10}$-Y-A-D-S-V-K-$\theta_{17}$ (SEQ ID NO: 173), where $\theta_1$ is D, A, or G; $\theta_3$ is T, V, I, S, A, or M; $\theta_5$ is V, G, D, N, T, or A; $\theta_6$ is R, Q, G, A, or V; $\theta_8$ is Y, I, D, S, or F; $\theta_{10}$ is E, D, or G; and $\theta_{17}$ is G or D.

2.9.6. CDR-L3 Consensus Sequences

In some embodiments, the antibody comprises a CDR-L3 sequence defined by the consensus sequence $\iota_1$-Q-$\iota_3$-$\iota_4$-$\iota_5$-to-P-$\iota_8$-T, where ii is Q or F; $\iota_3$ S or G; $\iota_4$ is N or S $\iota_5$ is E or H; $\iota_6$ is D or V; and $\iota_8$ is Y or W.

2.9.7. CDR-L2 Consensus Sequences

In some embodiments, the antibody comprises a CDR-L2 sequence defined by the consensus sequence $\lambda_1$-$\lambda_2$-S-N-$\lambda_5$-$\lambda_6$-S, where $\lambda_1$ is A or K; $\lambda_2$ is A or V; $\lambda_5$ is L or R; $\lambda_6$ is E or F.

2.9.8. CDR-L1 Consensus Sequences

In some embodiments, the antibody comprises a CDR-L1 sequence defined by the consensus sequence $\mu_1$-$\mu_2$-S-Q-$\mu_6$-$\mu_7$-$\mu_8$-$\mu_9$-$\mu_{10}$-$\mu_{11}$-$\mu_{12}$-$\mu_{13}$-$\mu_{14}$-$\mu_{15}$-$\mu_{16}$, where $\mu_1$ is K or R; $\mu_2$ is A or S; $\mu_6$ is V or I; $\mu_7$ is D or V; $\mu_8$ is Y or H; $\mu_9$ is D or T; $\mu_{10}$ is absent or N; $\mu_{11}$ is G; $\mu_{12}$ is N; $\mu_{13}$ is S or T; $\mu_{14}$ is Y; $\mu_{15}$ is V or L; and $\mu_{16}$ is N, A, or E.

In some embodiments, the antibody comprises a CDR-L1 sequence defined by the consensus sequence K-A-S-S-Q-V-D-Y-D-G-N-S-Y-V-$\mu_{16}$ (SEQ ID NO: 174), where $\mu_{16}$ is N or A.

3. Germline

In some embodiments, the antibody that specifically binds Tim-3 is an antibody comprising a variable region that is encoded by a particular germline gene, or a variant thereof. The illustrative antibodies provided herein comprise variable regions that are encoded by the heavy chain variable region germline genes VH3-23 and VH5-51, or variants thereof and the light chain variable region germline genes Vκ-20 and Vκ4-1, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H3$ or $V_H5$ families, or a variant thereof. In some embodiments, a CDR-L sequence provided herein may be combined with a variable region encoded by a variable region germline gene selected from the Vκ$_3$ or Vκ4 families, or a variant thereof.

4. Affinity

In some embodiments, the affinity of the antibody for Tim-3 as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the affinity of the antibody for human Tim-3, as determined by surface plasmon resonance at 25° C., and as indicated by $K_D$, is between about $9.1 \times 10^{-9}$ M and about $4.3 \times 10^{-9}$ M. In some embodiments, the affinity of the antibody for human Tim-3 is about $9.1 \times 10^{-9}$ M, about $8.1 \times 10^{-9}$ M, about $7.9 \times 10^{-9}$ M, about $7.6 \times 10^{-9}$ M, about $7.46 \times 10^{-9}$ M, about $7.2 \times 10^{-9}$ M, about $6.8 \times 10^{-9}$ M, about $6.7 \times 10^{-9}$ M, about $6.69 \times 10^{-9}$ M, about $6.2 \times 10^{-9}$ M, about $6.0 \times 10^{-9}$ M, about $5.9 \times 10^{-9}$ M, about $5.7 \times 10^{-9}$ M, about $5.6 \times 10^{-9}$ M, about $5.5 \times 10^{-9}$ M, about $5.4 \times 10^{-9}$ M, about $5.3 \times 10^{-9}$ M, about $5.0 \times 10^{-9}$ M, about $4.97 \times 10^{-9}$ M, about $4.9 \times 10^{-9}$ M, about $4.8 \times 10^{-9}$ M, or about $4.3 \times 10^{-9}$ M.

In some embodiments the antibody has a $k_a$ of at least about $10^4$ M$^{-1}$×sec$^{-1}$. In some embodiments the antibody has a $k_a$ of at least about $10^5$ M$^{-1}$×sec$^{-1}$. In some embodiments the antibody has a $k_a$ of at least about $10^6$ M$^{-1}$×sec$^{-1}$. In some embodiments the antibody has a $k_a$ of between about $10^4$ M$^{-1}$×sec$^{-1}$ and about $10^5$ M$^{-1}$×sec$^{-1}$. In some embodiments the antibody has a $k_a$ of between about $10^5$ M$^{-1}$×sec$^{-1}$ and about $10^6$ M$^{-1}$×sec$^{-1}$.

In some embodiments the antibody has a $k_a$ when associating with human Tim-3, as determined by surface plasmon resonance at 25° C., of between about $6.71 \times 10^4$ M$^{-1}$×sec$^{-1}$ and about $2.81 \times 10^5$ M$^{-1}$×sec$^{-1}$. In some embodiments the antibody has a $k_a$ when associating with human Tim-3 of about $6.71 \times 10^4$ M$^{-1}$×sec$^{-1}$, $1.21 \times 10^5$ M$^{-1}$×sec$^{-1}$, about $1.33 \times 10^5$ M$^{-1}$×sec$^{-1}$, about $1.35 \times 10^5$ M$^{-1}$×sec$^{-1}$, about $1.50 \times 10^5$ M$^{-1}$×sec$^{-1}$, about $1.57 \times 10^5$ M$^{-1}$×sec$^{-1}$, about $1.85 \times 10^5$ M$^{-1}$×sec$^{-1}$, about $1.89 \times 10^5$ M$^{-1}$×sec$^{-1}$, about $1.91 \times 10^5$ M$^{-1}$×sec$^{-1}$, about $1.97 \times 10^5$ M$^{-1}$×sec$^{-1}$, about $2.02 \times 10^5$ M$^{-1}$×sec$^{-1}$, about $2.27 \times 10^5$ M$^{-1}$×sec$^{-1}$, about $2.75 \times 10^5$ M$^{-1}$×sec$^{-1}$, or about $2.81 \times 10^5$ M$^{-1}$×sec$^{-1}$.

In some embodiments the antibody has a $k_d$ of about $10^{-5}$ sec$^{-1}$ or less. In some embodiments the antibody has a $k_d$ of about $10^{-4}$ sec$^{-1}$ or less. In some embodiments the antibody has a $k_d$ of about $10^{-3}$ sec$^{-1}$ or less. In some embodiments the antibody has a $k_d$ of between about $10^{-2}$ sec$^{-1}$ and about $10^{-5}$ sec$^{-1}$. In some embodiments the antibody has a $k_d$ of between about $10^{-2}$ sec$^{-1}$ and about $10^{-4}$ sec$^{-1}$. In some embodiments the antibody has a $k_d$ of between about $10^{-3}$ sec$^{-1}$ and about $10^{-5}$ sec$^{-1}$.

In some embodiments the antibody has a $k_d$ when dissociating from human Tim-3, as determined by surface plasmon resonance at 25° C., of between about $2.05 \times 10^{-2}$ sec$^{-1}$ and about $4.25 \times 10^4$ sec$^{-1}$. In some embodiments the antibody has a $k_a$ when dissociating from human Tim-3 of about $2.05 \times 10^{-2}$ sec$^{-1}$, about $1.40 \times 10^{-2}$ sec$^{-1}$, about $1.26 \times 10^{-2}$ sec$^{-1}$, about $3.93 \times 10^{-3}$ sec$^{-1}$, about $3.74 \times 10^{-3}$ sec$^{-1}$, about $2.49 \times 10^{-3}$ sec$^{-1}$, about $2.43 \times 10^{-3}$ sec$^{-1}$, about $1.82 \times 10^{-3}$ sec$^{-1}$, about $1.66 \times 10^{-3}$ sec$^{-1}$, about $1.59 \times 10^{-3}$ sec$^{-1}$, about $1.17 \times 10^{-3}$ sec$^{-1}$, about $5.44 \times 10^{-4}$ sec$^{-1}$, about $4.58 \times 10^{-4}$ sec$^{-1}$, or about $4.25 \times 10^{4}$ sec$^{-1}$.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

In some embodiments, the affinity of the antibody for cynomolgus Tim-3, as determined by surface plasmon resonance at 25° C., and as indicated by $K_D$, is between about 13.2 nM and about 0.5 nM. In some embodiments, the affinity of the antibody for human Tim-3 is about 13.2 nM, about 12.4 nM, about 9.4 nM, about 9.3 nM, about 7.4 nM, about 6.9 nM, about 5.6 nM, about 5.5 nM, about 5.4 nM, about 5.3 nM, about 4.7 nM, about 4.6 nM, about 4.5 nM, about 4.3 nM, about 4.1 nM, about 3.0 nM, about 2.8 nM, about 2.7 nM, about 2.5 nM, about 2.3 nM, about 2.2 nM, about 2.1 nM, about 1.9 nM, about 1.7 nM, about 1.0 nM, about 0.8 nM, or about 0.5 nM.

5. Epitope Bins

In some embodiments, the antibody binds the same epitope as the scFv antibody provided in SEQ ID NO: 169. In some embodiments, the antibody binds to a different epitope from the scFv antibody provided in SEQ ID NO: 169. In some embodiments, the antibody binds the same epitope as antibody encompassing any of SEQ ID NOs:130-157. In some embodiments, the antibody binds the same epitope as an antibody comprising any of the $V_H$-$V_L$ pairs, above. In some embodiments, the antibody binds to part of the epitope bound by the scFv antibody provided in SEQ ID NO: 169. In some embodiments, the antibody competes for epitope binding with the scFv antibody provided in SEQ ID NO: 169. In some embodiments, the antibody does not compete for epitope binding with scFv antibody provided in SEQ ID NO: 130. In some embodiments, the antibody competes for epitope binding with an antibody encompassing any of SEQ ID NOs:130-157. In some embodiments, the antibody competes for epitope binding with an antibody comprising any of the $V_H$-$V_L$ pairs, above.

6. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. USA.*, 1986, 83:7059-7063; Hellstrom et al., *Proc. Natl. Acad. Sci. USA.*, 1985, 82:1499-1502; and Bruggemann et al., *J. Exp. Med.*, 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. USA.*, 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., *J. Immunol. Methods*, 1996, 202:163-171; Cragg et al., *Blood*, 2003, 101: 1045-1052; and Cragg and Glennie, *Blood*, 2004, 103:2738-2743; each of which is incorporated by reference in its entirety.

FcRn binding and in vivo clearance (half-life determination) can also be measured, for example, using the methods described in Petkova et al., *Intl. Immunol.*, 2006, 18:1759-1769, incorporated by reference in its entirety.

8. Preparation of Antibodies 8.1. Antigen Preparation

The Tim-3 antigen to be used for isolation of the antibodies may be intact Tim-3 or a fragment of Tim-3. The intact Tim-3, or fragment of Tim-3, may be in the form of an isolated protein or protein expressed by a cell. Other forms of Tim-3 useful for generating antibodies will be apparent to those skilled in the art.

8.2. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133: 3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

8.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. USA.*, 1998, 95:8910-8915; Steinberger et al., *J. Biol. Chem.*, 2000, 275:36073-36078; Queen et al., *Proc. Natl. Acad. Sci. USA.*, 1989, 86:10029-10033; and U.S. Pat. Nos. 5,585,089, 5,693,761, 5,693,762, and 6,180,370; each of which is incorporated by reference in its entirety.

8.4. Human Antibodies

Human antibodies can be generated by a variety of techniques known in the art, for example by using transgenic animals (e.g., humanized mice). See, e.g., Jakobovits et al., *Proc. Natl. Acad. Sci. USA.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573, 905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9. Vectors, Host Cells, and Recombinant Methods

The invention also provides isolated nucleic acids encoding anti-Tim-3 antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter*, *Erwinia*, *Klebsiella*, *Proteus*, *Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-Tim-3 antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe*, *Kluyveromyces* (*K. lactis*, *K fragilis*, *K. bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-Tim-3 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et $\alpha_1$. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human $\gamma_1$, $\gamma_2$, or $\gamma_4$ heavy chains (Lindmark et al., *J. Immunol. Meth.*, 1983, 62:1-13, incorporated by reference in its entirety). Protein G is useful for all mouse isotypes and for human $\gamma_3$ (Guss et al., *EMBO* 1, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

10. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

10.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

10.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is about 0.1 mg/kg, about 1 mg/kg, about 2 mg/kg, about 3 mg/kg, about 4 mg/kg, about 5 mg/kg, about 6 mg/kg, about 10 mg/kg, or about 15 mg/kg or more of a subject's body weight. In another embodiment, the dosage of the composition or a composition provided herein administered to prevent, treat, manage, or ameliorate a disorder, or one or more symptoms thereof in a subject is about 0.1 mg to about 200 mg, about 0.1 mg to about 100 mg, about 0.1 mg to about 50 mg, about 0.1 mg to about 25 mg, about 0.1 mg to about 20 mg, about 0.1 mg to about 15 mg, about 0.1 mg to about 10 mg, about 0.1 mg to about 7.5 mg, about 0.1 mg to about 5 mg, about 0.1 to about 2.5 mg, about 0.25 mg to about 20 mg, about 0.25 to about 15 mg, about 0.25 to about 12 mg, about 0.25 to about 10 mg, about 0.25 mg to about 7.5 mg, about 0.25 mg to about 5 mg, about 0.25 mg to about 2.5 mg, about 0.5 mg to about 20 mg, about 0.5 to about 15 mg, about 0.5 to about 12 mg, about 0.5 to about 10 mg, about 0.5 mg to about 7.5 mg, about 0.5 mg to about 5 mg, about 0.5 mg to about 2.5 mg, about 1 mg to about 20 mg, about 1 mg to about 15 mg, about 1 mg to about 12 mg, about 1 mg to about 10 mg, about 1 mg to about 7.5 mg, about 1 mg to about 5 mg, or about 1 mg to about 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least about 1 day, about 2 days, about 3 days, about 5 days, about 10 days, about 15 days, about 30 days, about 45 days, about 2 months, about 75 days, about 3 months, or about 6 months. In other embodiments, administration of the same prophylactic or therapeutic agent may be repeated and the administration may be separated by at least about 1 day, about 2 days, about 3 days, about 5 days, about 10 days, about 15 days, about 30 days, about 45 days, about 2 months, about 75 days, about 3 months, or about 6 months.

11. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving Tim-3. In some embodiments, the disease or condition is a disease or condition that can be diagnosed by overexpression of Tim-3. In some embodiments, the disease or condition is a disease or condition that can benefit from treatment with an anti-Tim-3 antibody. In some embodiments, the disease or condition is a cancer.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In particular embodiments, the cancer is a cancer of epithelial origin. In some aspects, the cancer is a carcinoma. In some aspects, the cancer is selected from an adenocarcinoma, a squamous cell carcinoma, an adenosquamos carcinoma, an anaplastic carcinoma, a large cell carcinoma, small cell carcinoma, and carcinoma of unknown primary origin.

12. Diagnostic Applications

In some embodiments, the antibodies provided herein are used in diagnostic applications. For example, an ant-Tim-3 antibody may be useful in assays for Tim-3 protein. In some aspects the antibody can be used to detect the expression of Tim-3 in various cells and tissues. These assays may be useful, for example, in making a diagnosis and/or prognosis for a disease, such as a cancer.

In some diagnostic and prognostic applications, the antibody may be labeled with a detectable moiety. Suitable detectable moieties include, but are not limited to radioisotopes, fluorescent labels, and enzyme-substrate labels. In another embodiment, the anti-Tim-3 antibody need not be labeled, and the presence of the antibody can be detected using a labeled antibody which specifically binds to the anti-Tim-3 antibody.

13. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the Tim-3 protein (or fragment thereof) to be purified, and thereafter the support is washed with a suitable solvent that will remove substantially all the material in the sample except the Tim-3 protein, which is bound to the immobilized antibody. Finally, the support is washed with another suitable solvent, such as glycine buffer, pH 5.0 that will release the Tim-3 protein from the antibody.

14. Kits

In some embodiments, an anti-Tim-3 antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-Tim-3 antibody. In some embodiments, the anti-Tim-3 antibody is provided in the form of a pharmaceutical composition.

EXAMPLES

Example 1: Hybridoma Generation

Balb/C mice were immunized with the extracellular domain of human Tim-3 fused with human Fc (R&D Systems) using standard immunization methods. The spleens and/or lymph nodes of the mice were harvested and fused with P3X cells to generate the hybridomas (Aragen Biosciences, Morgan Hill, Calif.), similar to published reports. See Chronopoulou et al., 2014, *Methods Mol Biol.* 1131: 47-70 (2014); Kim et al., 2014, *Methods Mol Biol.* 1131: 33-45; each incorporated by reference in its entirety. Total RNA was extracted from hybridoma cells using QIAGEN RNeasy Mini Kit (Cat No. 74104) and converted to cDNA using a Clontech SMARTer RACE cDNA Amplification Kit (Cat. No. 634923; Lake Pharma, Belmont, Calif.). Positive clones were identified by gel electrophoresis, cloned using an Invitrogen TOPO kit, and sequenced using standard Sanger methods. Mouse single-chain antibodies were constructed by using total gene synthesis using optimized *E. Coli* codons and cloned into a standard cell-free expression vector. See Yin et al., supra.

Mouse hybridoma clone 22E11 showed binding of human Tim-3 expressed on CHO cells and binding of cynomolgus Tim-3 expressed on CHO cells. The $k_a$ for the m22E11 Ab was $2.23 \times 10^5$ $M^{-1} \times sec^{-1}$; the $k_d$ was $3.34 \times 10^4$ $sec^{-1}$, and the $K_D$ was $1.50 \times 10^{-9}$ M.

Mouse hybridoma clone 2D5 showed binding of human Tim-3 expressed on CHO cells, but no binding of cynomolgus Tim-3 expressed on CHO cells. The $k_a$ for the 2D5 Ab was $3.86 \times 10^5$ $M^{-1} \times sec^{-1}$; the $k_a$ was $1.66 \times 10^4$ $sec^{-1}$, and the $K_D$ was $4.31 \times 10^{-10}$ M.

The CDRs for clone m22E11 were grafted onto human antibody frameworks VH1-69, VH3-23, VH4-30-4, VH5-51, VH3-33 (h22E11-5 HC), Vk1-39, Vk2-28, Vk3-11, Vk4-1 and Vk3-20 (h22E11-5) LC by standard methodology to yield humanized antibodies of every HC and LC combination. See Kuramochi et al., 2014, *Methods in Molecular Biology* 1060: 123-137. In the results below, "h22E11" indicates a humanized variant of m22E11. The heavy chains are indicated by framework designation (e.g., "VH1-69") and the light chains are indicated by framework designation (e.g., "Vk1-39").

TABLE 5

Antibodies From 2D5 and 22E11

| Antibody | VH | VL |
|---|---|---|
| 250.180.2.22E11 | 22E11-VH | 22E11-VL |
| 421.51.2.2D5.5E9 | 2D5-VH | 2D5-VL |
| h22E11-VK1-39 × h22E11-VH1-69 | h22E11-VH1-69-VH | h22E11-Vk1-39-VL |
| h22E11-VK1-39 × h22E11-VH3-23 | h22E11-VH3-23-VH | h22E11-Vk1-39-VL |
| h22E11-VK1-39 × h22E11-VH4-30-4 | h22E11-VH4-30-4-VH | h22E11-Vk1-39-VL |
| h22E11-VK1-39 × h22E11-VH5-51 | h22E11-VH5-51-VH | h22E11-Vk1-39-VL |
| h22E11-VK1-39 × h22E11-5-IgG-HC | h22E11-5-VH | h22E11-Vk1-39-VL |
| h22E11-VK2-28 × h22E11-VH1-69 | h22E11-VH1-69-VH | h22E11-Vk2-28-VL |

TABLE 5-continued

Antibodies From 2D5 and 22E11

| Antibody | VH | VL |
| --- | --- | --- |
| h22E11-VK2-28 × h22E11-VH3-23 | h22E11-VH3-23-VH | h22E11-Vk2-28-VL |
| h22E11-VK2-28 × h22E11-VH4-30-4 | h22E11-VH4-30-4-VH | h22E11-Vk2-28-VL |
| h22E11-VK2-28 × h22E11-VH5-51 | h22E11-VH5-51-VH | h22E11-Vk2-28-VL |
| h22E11-VK2-28 × h22E11-5-IgG-HC | h22E11-5-VH | h22E11-Vk2-28-VL |
| h22E11-VK3-11 × h22E11-VH1-69 | h22E11-VH1-69-VH | h22E11-Vk3-11-VL |
| h22E11-VK3-11 × h22E11-VH3-23 | h22E11-VH3-23-VH | h22E11-Vk3-11-VL |
| h22E11-VK3-11 × h22E11-VH4-30-4 | h22E11-VH4-30-4-VH | h22E11-Vk3-11-VL |
| h22E11-VK3-11 × h22E11-VH5-51 | h22E11-VH5-51-VH | h22E11-Vk3-11-VL |
| h22E11-VK3-11 × h22E11-5-IgG-HC | h22E11-5-VH | h22E11-Vk3-11-VL |
| h22E11-VK4-1 × h22E11-VH1-69 | h22E11-VH1-69-VH | h22E11-Vk4-1-VL |
| h22E11-VK4-1 × h22E11-VH3-23 | h22E11-VH3-23-VH | h22E11-Vk4-1-VL |
| h22E11-VK4-1 × h22E11-VH4-30-4 | h22E11-VH4-30-4-VH | h22E11-Vk4-1-VL |
| h22E11-VK4-1 × h22E11-VH5-51 | h22E11-VH5-51-VH | h22E11-Vk4-1-VL |
| h22E11-VK4-1 × h22E11-5-IgG-HC | h22E11-5-VH | h22E11-Vk4-1-VL |
| h22E11-5-IgG-LC × h22E11-VH1-69 | h22E11-VH1-69-VH | h22E11-5-VL |
| h22E11-5-IgG-LC × h22E11-VH3-23 | h22E11-VH3-23-VH | h22E11-5-VL |
| h22E11-5-IgG-LC × h22E11-VH4-30-4 | h22E11-VH4-30-4-VH | h22E11-5-VL |
| h22E11-5-IgG-LC × h22E11-VH5-51 | h22E11-VH5-51-VH | h22E11-5-VL |
| h22E11-5-IgG-LC × h22E11-5-IgG-HC | h22E11-5-VH | h22E11-5-VL |
| h22E11-5 IgG | h22E11-5-VH | h22E11-5-VL |

Example 2: Generation and Primary Screening of Anti-Tim-3 Antibodies

Antibody Fab libraries were constructed using a standard overlap extension PCR protocol with mutagenic primers targeting complementary determining regions (CDRs). See Heckman and Pease, Nat. Protoc., 2007, 2:924-932; Stafford et al., 2014, Protein Eng. Des. Sel. 27:97-109, both incorporated by reference in their entireties.

Initial antibody leads from ribosome display (e.g. SRP1497 antibodies) were derived from a naïve human library which was constructed by overlapping PCR using trastuzumab HC as the base template. CDRs H1 and H2 were randomized with the same design as described by Lee et al., 2004, J. Mol. Biol. 2004, 340:1073-1093 using oligonucleotides purchased from Integrated DNA Technologies. In this design, CDRs H1 and H2 closely match the observed amino acid distributions of natural human antibodies. CDR H3 was diversified using oligonucleotides incorporating trimer phosphoramidite mixtures (TRIMs) for amino acid randomization. The TRIM oligos were synthesized as described by Yagodkin A et al., Nucleosides Nucleotides Nucleic Acids 2007, 26:473-97. Specifically, six separate oligonucleotides containing TRIMs were used to make 6 separate H3 loop-lengths (13-18; as defined by Zemlin et al.) to match the most common loop lengths observed in the human repertoire. Together these loop lengths comprise approximately 54.5% of the naturally-occurring loop length variation in human IgGs as reported by Zemlin et al., J. Mol. Biol. 2003, 334:733-749. The frequency distribution of each amino acid was designed to closely match the observed distribution of amino acids in CDR H3 of human IgGs as reported by Zemlin et al. Altogether, the library closely matches natural human antibody variation which is known in the field to improve antibody stability and folding of antibodies as described by Zhai et al., J. Mol Biol. 2011, 412:55-71. The HC library was paired with a constant, unmodified trastuzumab LC throughout the selection process as described by Stafford et al., Protein Eng Des Sel 2014, 27:97-109.

Affinity maturated antibody leads (e.g. SRP1649 antibodies) were derived from a focused library, biased towards the lead (1497-A05) which was constructed by overlapping PCR using "soft-randomized" oligonucleotides purchased from Eurofins MWG Operon. Soft-randomization is a process in which a biased distribution of nucleotides is used for each soft-randomized codon such that the parent amino acid sequence is coded more frequently than other amino acids ~30% of the time. Other amino acids are coded at each position but at a lower percentage. At each soft-randomized position, 70% of the parent nucleotide is mixed with 10% of the other three nucleotides. For the library, CDRs H1, H2, and H3 were soft-randomized simultaneously and selected by standard ribosome display protocols. As with the selection of initial leads, the affinity matured antibodies were paired with a constant, unmodified trastuzumab LC throughout the selection process as described by Stafford et al., Protein Eng Des Sel 2014, 27:97-109.

Selections for novel antibodies were performed using standard ribosome display protocols. See Dreier and Plückthun, Methods Mol. Biol., 2003, 687:283-306, Clifton, N.J., incorporated by reference in its entirety. Fab ribosome display selections were performed according to published protocols. See Stafford et al., 2014, Protein Eng. Des. Sel. 27:97-109, incorporated by reference in its entirety. After multiple rounds of selection, the DNA from RT-PCR output was cloned into an optimized vector for cell-free expression using standard molecular biology techniques. See Yin et al., mAbs, 2012, 4:217-225, incorporated by reference in its entirety. All constructs were HIS- and FLAG-tagged to streamline purification and testing during screening.

Libraries of antibody variants generated by selection workflow were transformed into E. coli and grown on agar plates with antibiotic (kanamycin). Individual colonies were grown in liquid broth (TB+kanamycin), and used as a template for DNA amplification via rolling circle amplification (RCA). The Fab-HC variants, together with about 2.5 µg/mL of a trastuzumab LC, were then expressed in cell-free protein synthesis reactions as described in Zawada et al., Biotechnol. Bioeng., 2011, 108:1570-1578, incorporated by reference in its entirety.

Briefly, cell-free extracts were treated with 50 µM iodoacetamide for 30 min at room temperature (20° C.) and added to a premix containing cell-free components (see Groff et al., mAbs, 2014, 6:671-678, incorporated by reference in its entirety) and 10% (v/v) RCA DNA template (approximately 10 μg/mL DNA) for HC variants, in addition to 2.5 ug/mL Trastuzumab LC which is present for antibody assembly but does not contribute to the binding to the target antigen. Sixty microliters of cell-free reactions were incubated at 30° C. for 12 hr on a shaker at 650 rpm in 96-well plates. Four hundred to one-thousand-five-hundred colonies were screened, depending on the predicted diversity of different selection campaigns.

Following synthesis, each reaction was diluted 1:50 into PBST (PBS at pH 7.4 with 0.2% Tween-20+0.2% BSA) and expressed variants were tested for functional activity via ELISA-based binding to recombinant human Tim-3 extracellular domain (ECD) (Acro Biosystems, TM3-H5229, Accession #Q8TDQ0; R&D Systems, 2365-TM, Accession #Q8TDQ0). Standard ELISA-based methods were employed. Specifically, 384-well plates were coated with 2 μg/mL recombinant Tim-3 diluted in bicarbonate buffer, and then blocked with bovine serum albumin (BSA). Antibody variants of interest were allowed to bind to the Tim-3-coated plates, and detected with secondary antibodies (e.g., HRP-conjugated anti-human Fc or anti-FLAG) and then detected with chemiluminescent substrate (Pierce ELISA SuperSignal™ Substrate). Chemiluminescence was quantified on a Molecular Devices SpectraMax® M5 plate reader. Top hits were selected based on ELISA signal or signal/noise ratio and their nucleotides were sequenced. Based on functional activity and sequence analysis, a subset of variants was selected for further scale-up and characterization. The resulting antibodies are reported in Table 6, below, beginning with the designation SRP1497.

The top leads from ELISA-based screening were cultured and plasmid minipreps were performed using a QIAprep® 96 Turbo miniprep kit (Qiagen) according to the manufacturer's instructions. 10 ng/mL miniprepped DNA was added to 4 mL cell-free reactions and incubated overnight for 12 hr at 30° C., at 650 rpm. In the case of IgG variants with a common Trastuzumab LC, 7.5 ug/mL of the HC variant DNA and 2.5 ug/mL of the common Trastuzumab LC were added to the reaction.

Expressed variants from clarified cell-free reactions were purified via immobilized metal ion affinity chromatography (IMAC) purification using a semi-automated high throughput batch purification method. Briefly, purifications were performed in a 96-well plate format where 50 μL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 μL IMAC elution buffer (50 mM Tris pH 8.0, 300 mM NaCl, 500 mM imidazole) and buffer exchanged into PBS using a 96-well Zeba plate (7 kD MWCO, Thermo Fisher). Purified antibodies were quantified via high throughput capillary electrophoresis using the LabChip GXII (Perkin Elmer) against a Herceptin standard curve, according to the manufacturer's instructions.

TABLE 6

Naïve (1497) and Affinity Matured (1649) Antibodies

| Antibody | VH | VL |
| --- | --- | --- |
| SRP1497-A01 | SRP1497-A01 | trastuzumab VL |
| SRP1497-A02 | SRP1497-A02 | trastuzumab VL |
| SRP1497-A05 | SRP1497-A05 | trastuzumab VL |
| SRP1649-A01 | SRP1649-A01 | trastuzumab VL |
| SRP1649-B06 | SRP1649-B06 | trastuzumab VL |

TABLE 6-continued

Naïve (1497) and Affinity Matured (1649) Antibodies

| Antibody | VH | VL |
| --- | --- | --- |
| SRP1649-B09 | SRP1649-B09 | trastuzumab VL |
| SRP1649-C05 | SRP1649-C05 | trastuzumab VL |
| SRP1649-D06 | SRP1649-D06 | trastuzumab VL |
| SRP1649-D11 | SRP1649-D11 | trastuzumab VL |
| SRP1649-E08 | SRP1649-E08 | trastuzumab VL |
| SRP1649-E10 | SRP1649-E10 | trastuzumab VL |
| SRP1649-F06 | SRP1649-F06 | trastuzumab VL |
| SRP1649-G08 | SRP1649-G08 | trastuzumab VL |
| SRP1649-H02 | SRP1649-H02 | trastuzumab VL |

Example 3: Affinity and Kinetic Binding Analyses

Monoclonal Anti-FLAG M2 IgG (Sigma-Aldrich #F9291) was immobilized onto a CMS chip (GE Life Sciences) using amine coupling chemistry (from Amine Coupling Kit, GE Life Sciences). The immobilization steps were carried out at a flow rate of 25 μL/min in 1×HBS-EP+ buffer (GE Life Sciences; 10× Stock diluted before use). The sensor surfaces were activated for 7 min with a mixture of NHS (0.05 M) and EDC (0.2 M). The Anti-Flag M2 IgG was injected over all 4 flow cells at a concentration of 25 μg/mL in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1×HBS-EP+ buffer. Test and control antibodies were injected over the Anti-FLAG surface at concentrations of 5-10 μg/mL for 12 seconds at a flow rate of 10 μL/min on flow cells 2, 3 and 4, followed by a buffer wash for 30 seconds at the same flow rate. Kinetic characterization of antibody samples was carried out with a single concentration of antigen (for off-rate ranking) or a dilution series of antigen (for kinetic characterization) and 1 injection of 0 nM antigen. After capturing ligand (antibody) on the anti-FLAG surface, the analyte (human Tim-3-Fc) was bound at 50, 25, 12.5, 6.25 and 0 nM for 180 seconds, followed by a 600 second dissociation phase at a flow rate of 50 μl/min. Between each ligand capture and analyte binding cycle, regeneration was carried out using 2 injections of 10 mM glycine pH 2.0 for 30 seconds at 30 μL/min, followed by a 30 second buffer wash step.

The data were fit with the Biacore T200 Evaluation software, using a 1:1 *Langmuir* binding model. $K_D$ (affinity, nM) was determined as a ratio of the kinetic rate constants calculated from the fits of the association and dissociation phases.

Example 4: Tim-3/Galectin9 Competition ELISA

Anti-TIM3 variants were tested for their ability to block a TIM3/Galectin9 interaction. Galectin-9 (R&D Systems) was adsorbed on Nunc 384-well white Maxisorp plates at 2 μg/mL in sodium bicarbonate buffer (pH 8.9) and incubated at 30° C. for 1 hour or overnight at 4° C. The plate was washed 3 times with PBS pH 7.4 with 0.05% Tween20 and blocked with 2% bovine serum albumin (BSA) in PBS pH 7.4+0.1% Tween20 for 1 hour at 30° C. The blocking solution was aspirated, and a dilution series of antibody was mixed with 10 nM biotinylated TIM3-Fc (R&D Systems) in 0.2% BSA in PBS pH 7.4+0.1% Tween20 (diluent buffer) and incubated at 30° C. for 1 hour. The plate was washed, and streptavidin-HRP (Pierce) in diluent buffer was added to all wells. After 1 hour incubation at 30° C., the plate was washed, followed by detection with SuperSignal Pico Chemiluminescent Substrate (Thermo Pierce). Luminescence was detected on a SpectraMax® M5 plate reader (Molecular Devices).

Example 5: Tim-3 ELISA

Anti-TIM3 variants were tested for their ability to bind human or cynomolgous TIM-3. Recombinant Tim-3 protein (R&D Systems, huTIM3-Fc, 2365-TM, Accession #Q8TDQ0; cyTIM3-Fc, 7914-TM, Accession #EHH54703) was adsorbed on Nunc 384-well white Maxisorp plates at 2 µg/mL in sodium bicarbonate buffer (pH 8.9) and incubated at 30° C. for 1 hour or overnight at 4° C. The plate was washed 3 times with PBS pH 7.4 with 0.05% Tween20 and blocked with 2% bovine serum albumin (BSA) in PBS pH 7.4+0.1% Tween20 for 1 hour at 30° C. The blocking solution was aspirated, and a dilution series of anti-TIM-3 antibody in 0.2% BSA in PBS pH 7.4+0.1% Tween20 (diluent buffer) was pipetted to the ELISA plate and incubated at 30° C. for 1 hour. The plate was washed, and anti-Flag-HRP (Sigma-Aldrich, A8592) in diluent buffer was added to all wells. After 1 hour incubation at 30° C., the plate was washed, followed by detection with SuperSignal Pico Chemiluminescent Substrate (Thermo Pierce). Luminescence was detected on a SpectraMax® M5 plate reader (Molecular Devices).

Example 6: Flow Cytometry-Based Cell Binding Assay

CHO-k cells were transfected to stably express Tim-3 on the cell surface. CHO parental and stably transfected CHO-Tim-3 cells (human or cynomolgus Tim-3) were cultured in RPMI w/10% fetal calf serum (FCS), Penicillin/Streptomycin (or Pen/Strep) and glutamine (or Gln). On day of assay, cells were washed with DPBS, detached with Accutase™ (BD Biosciences; San Jose, Calif.), and resuspended in RPMI media.

A mixture of fluoresecent-labeled parental CHO cells and unlabeled CHO-Tim-3 cells were prepared as follows. Parental CHO cells in RPMI media were incubated with 1 uM CellTrace™ Oregon Green488® (Life Technologies) at 37° C. for 15 to 30 minutes. Cells were then washed 3× with RPMI media. Labeled parental CHO and unlabeled CHO-Tim-3 cells were combined at 1:1 ratio, washed 1× in ice-cold FACS buffer (DPBS buffer supplemented with 0.5% bovine serum albumin) and seeded at 100 µl per well containing a total of 200,000 cells in 96 well polypropylene plates. Cells were spun down at 1.5K rpm and resuspended with test antibodies diluted in FACS buffer and incubated on ice for 60 mins. Cells were washed twice with FACS buffer and incubated on ice for 30 mins with R-phycoerythrin AffiniPure F(ab')2 fragment, goat anti-Human IgG, Fcγ fragment specific secondary detection antibody (Jackson ImmunoResearch Laboratories, West Grove, Pa.) diluted at 1:200 with FACS buffer. Cells were washed twice with FACS buffer, fixed in 4% paraformaldehyde in PBS (Santa Cruz Biotechnology; Dallas, Tex.) for 20 mins on ice in the dark, washed twice with FACS buffer and analyzed using the BD LSR II Flow Cytometer (BD Biosciences; San Jose, Calif.). Data were analyzed using FlowJo (FlowJo, LLC; Ashland, Oreg.) to determine mean fluorescence intensities. Binding constants were calculated using the statistical software, GraphPad Prism (GraphPad Software; La Jolla, Calif.) using the nonlinear regression equation, one site—specific binding with Hill slope. Secondary antibody alone was used as a control, in addition to measuring non-specific antibody binding to CHO parental cells.

Example 7: CMV Recall Assay

CD14+ monocytes and CD3+ T cells were obtained from peripheral blood mononuclear (PBMC) isolated from CMV+ human donors (AllCells, Alameda, Calif.) using MACS Cell Separation kits (Miltenyi Biotec). CD14+ monocytes were differentiated into immature dendritic cells (DC) by culturing cells at $10^6$ cells/ml for 7 days in presence of GM-CSF and IL-4 (Peprotech) in X-Vivo 15 media (Lonza) containing 2% human AB serum (Sigma-Aldrich), penicillin-streptomycin (Corning Mediatech) and GlutaMAX (Life Technologies). Following differentiation, DCs were matured by culturing in X-Vivo 15+2% human AB serum media at $10^6$ cells/ml for 2 days in the presence of GM-CSF, IL-4, TNF-α, IL-1b, IL-6 (Peprotech) and prostaglandin $\varepsilon_2$ (Sigma-Aldrich). To set-up the CMV recall assay, mature DCs were collected, washed and 10,000 DCs and 100,000 pan CD3+ T cells were plated per well in a 96-well U-bottom plate in a total volume of 100 µl media containing peptide pools for the CMV IE-1 and CMV pp65 protein (Miltenyi Biotec). IgG antibodies (50 ul) were added starting at a final concentration of 133 nM with 5-fold serial dilutions. Cells were co-cultured with peptides and antibodies for 5-6 days. Conditioned media was collected and tested for human IFN-g levels by ELISA (BD Biosciences).

Example 8: DC/CD4+ T Cell Mixed Lymphocyte Reaction (MLR))

CD14+ monocytes and CD4+ T cells were obtained from PBMC isolated from human donors using MACS Cell Separation kits. CD14+ monocytes were differentiated into immature DC by culturing cells at $10^6$ cells/ml cell density for 7 days in presence of GM-CSF and IL-4 in RPMI media containing 10% fetal bovine serum, penicillin-streptomycin and GlutaMAX. Following differentiation, DCs were matured by culturing in RPMI+10% FBS media at $10^6$ cells/ml cell density for 2 days in the presence of GM-CSF, IL-4, TNF-α, IL-1b, IL-6 and prostaglandin $\varepsilon_2$. To set-up the DC/CD4+ T cell MLR, mature DCs were collected, washed and 10,000 DCs and 100,000 CD4+ T cells were plated per well in a 96-well U-bottom plate in a total volume of 100 µl media. IgG antibodies (50 ul, final volume of 150 µl per well) were added starting at a final concentration of 133 nM with 5-fold serial dilutions. Cells were co-cultured with peptides and antibodies for 5-6 days. Conditioned media was collected and tested for human IFN-g levels by ELISA.

Example 9: Cell Binding on Activated Primary Human T Cells

CD4+ T cells were obtained from PBMC isolated from human donors using MACS Cell Separation kit. CD4+ T cells (2e6 cells/ml) were activated with CD3/CD28 Human T-Activator Dynabeads (Life Technologies) in RPMI+10% FBS media containing 100 U/ml human IL-2 (Peprotech) for 2-3 days. Activated CD4+ T cells expressing Tim-3 were used test anti-TIM3 antibodies for FACS cell binding.

Example 10: Characteristics of Illustrative Anti-Tim-3 Antibodies

Tables 7-8 show results obtained using the illustrative antibodies described herein.

Table 7 shows results from humanized variants of mouse hybridoma clone m22E11 with various human frameworks.

TABLE 7

| | Humanized h22E11 Antibody Characterization | | | | | | |
|---|---|---|---|---|---|---|---|
| | Human Tim-3 (Biacore) | | Human Tim-3 (CHO) | Human Tim-3 (T-Cell)) | Cyno Tim-3 (CHO) | Gal9 ELISA | |
| Humanized Antibody | $k_d$ (1/s) | $K_D$ (nM) estimated | $K_D$ (nM) | $K_D$ (nM) | $K_D$ (nM) | comp $IC_{50}$ (nM) | MLR activity IFNg release |
| h22E11-VK1-39 × h22E11-VH1-69 | 9.40E−04 | 6 | 0.6 | 2.6 | 1.7 | Not tested | Not tested |
| h22E11-VK1-39 × h22E11-VH3-23 | 9.40E−04 | 5.6 | 0.5 | 1.1 | 4.5 | Not tested | Not tested |
| h22E11-VK1-39 × h22E11-VH4-30-4 | 1.26E−03 | 9.1 | 0.7 | poor | 5.5 | Not tested | Not tested |
| h22E11-VK1-39 × h22E11-VH5-51 | 9.47E−04 | 5.3 | 0.4 | 0.9 | 2.1 | Not tested | Not tested |
| h22E11-VK1-39 × h22E11-5-IgG-HC | 1.02E−03 | 6.2 | 0.6 | 2.4 | 4.7 | Not tested | Not tested |
| h22E11-VK2-28 × h22E11-VH1-69 | 8.63E−04 | 5.4 | 0.7 | 2.3 | 1.7 | Not tested | Not tested |
| h22E11-VK2-28 × h22E11-VH3-23 | 9.11E−04 | 5.9 | 0.8 | 1.7 | 5.4 | Not tested | Not tested |
| h22E11-VK2-28 × h22E11-VH4-30-4 | 1.09E−03 | 7.9 | 0.8 | 9.2 | 4.3 | Not tested | Not tested |
| h22E11-VK2-28 × h22E11-VH5-51 | 9.03E−04 | 4.8 | 0.6 | 0.7 | 2.3 | Not tested | Not tested |
| h22E11-VK2-28 × h22E11-5-IgG-HC | 1.01E−03 | 6.7 | 0.8 | 3.3 | 4.1 | Not tested | Not tested |
| h22E11-VK3-11 × h22E11-VH1-69 | 8.67E−04 | 4.9 | 1 | 4 | 2.8 | Not tested | Not tested |
| h22E11-VK3-11 × h22E11-VH3-23 | 9.34E−04 | 5.3 | 0.7 | 0.9 | 6.9 | Not tested | positive |
| h22E11-VK3-11 × h22E11-VH4-30-4 | 1.07E−03 | 7.2 | 1 | 7.1 | 4.5 | Not tested | Not tested |
| h22E11-VK3-11 × h22E11-VH5-51 | 8.75E−04 | 4.3 | 0.8 | 0.6 | 2.7 | Not tested | positive |
| h22E11-VK3-11 × h22E11-5-IgG-HC | 1.04E−03 | 5.9 | 0.8 | 1.1 | 5.3 | 0.64 | Not tested |
| h22E11-VK4-1 × h22E11-VH1-69 | 8.63E−04 | 5.5 | 1 | 6.3 | 2.5 | Not tested | Not tested |
| h22E11-VK4-1 × h22E11-VH3-23 | 8.75E−04 | 5 | 0.9 | 0.9 | 4.6 | 0.67 | Not tested |
| h22E11-VK4-1 × h22E11-VH4-30-4 | 1.19E−03 | 8.1 | 1.1 | 5.7 | 5 | Not tested | Not tested |
| h22E11-VK4-1 × h22E11-VH5-51 | 8.81E−04 | 4.8 | 0.8 | 0.6 | 1.9 | Not tested | Not tested |
| h22E11-VK4-1 × h22E11-5-IgG-HC | 9.73E−04 | 5.7 | 0.8 | 1.4 | 5.3 | Not tested | Not tested |
| h22E11-5-IgG-LC × h22E11-VH1-69 | 9.91E−04 | 4.9 | 0.9 | 1.6 | 3 | Not tested | Not tested |
| h22E11-5-IgG-LC × h22E11-VH3-23 | 8.95E−04 | 5.3 | 0.8 | 1.2 | 13.2 | Not tested | Not tested |
| h22E11-5-IgG-LC × h22E11-VH4-30-4 | 1.17E−03 | 7.6 | 3.7 | poor | poor | Not tested | Not tested |
| h22E11-5-IgG-LC × h22E11-VH5-51 | 1.10E−03 | 5 | poor | poor | poor | Not tested | Not tested |
| h22E11-5-IgG-LC × h22E11-5-IgG-HC | 1.10E−03 | 6.8 | poor | poor | poor | Not tested | Not tested |
| h22E11-5 IgG (lot 2) | Not tested | Not tested | 1.0 | Not tested | poor | 0.77 | Not tested |

Table 8 shows results obtained from antibodies isolated from a naïve Fab TRIM ribosome display library, constructed on a Trastuzumab HC framework.

The "$EC_{50}$" value is the concentration of the antibody at which half-maximum signal is achieved in an ELISA assay where Tim-3 protein is adsorbed onto a plate and then bound by the respective antibody provided herein. The anti-Tim-3 antibody is detected with horseradish peroxidase (HRP)-conjugated anti-human Fc antibody.

TABLE 8

Results obtained from antibodies isolated from a first affinity matured library, based on the SRP1464-B04 antibody provided in Table 5.

| scFv-Fc Antibody | Human Tim-3 (Biacore) | | | Cell Binding | Human Tim-3-Fc ELISA | Cyno Tim-3-Fc ELISA | Gal9-blockade |
|---|---|---|---|---|---|---|---|
| | $k_a$ (1/Ms) | $k_d$ (1/s) | $K_D$ (M) | $K_D$ (nM) | $EC_{50}$ (nM) | $EC_{50}$ (nM) | $IC_{50}$ (nM) |
| SRP1497-A01 | 1.97E+05 | 4.25E−04 | 2.15E−09 | 1.17 | 0.30 | 22.56 | 0.8 |
| SRP1497-A02 | 1.85E+05 | 5.44E−04 | 2.95E−09 | 1.54 | 0.34 | 13.74 | 1.0 |
| SRP1497-A05 | 2.02E+05 | 4.58E−04 | 2.27E−09 | 5.6 | 0.24 | 6.193 | 1.1 |

Table 9 shows results obtained from antibodies isolated from a second affinity matured library constructed by performing soft randomization on the SRP1497-A05 antibody.

TABLE 9

Results obtained from antibodies isolated from a second affinity matured library.

| scFv-Fc Antibody | Human Tim-3 (Biacore) | | | Human Tim-3 (CHO) | Cyno Tim-3 (CHO) | Gal9-blockade |
|---|---|---|---|---|---|---|
| | $k_a$ (1/Ms) | $k_d$ (1/s) | $K_D$ (M) | $K_D$ (nM) | $K_D$ (nM) | $IC_{50}$ (nM) |
| SRP1649-A01 | 6.71E+04 | 1.17E−03 | 1.74E−08 | 0.4 | 0.5 | 0.26 |
| SRP1649-B06 | 1.89E+05 | 1.26E−02 | 6.69E−08 | 0.2 | 1.9 | Not tested |
| SRP1649-B09 | 1.33E+05 | 2.49E−03 | 1.88E−08 | 0.2 | 9.4 | Not tested |
| SRP1649-C05 | 1.21E+05 | 1.66E−03 | 1.37E−08 | 0.2 | 0.8 | Not tested |
| SRP1649-D06 | 2.75E+05 | 2.05E−02 | 7.46E−08 | 0.1 | 1.0 | Not tested |
| SRP1649-D11 | 1.50E+05 | 1.59E−03 | 1.06E−08 | 0.1 | 2.2 | Not tested |
| SRP1649-E08 | 1.35E+05 | 1.82E−03 | 1.35E−08 | 0.2 | 12.4 | Not tested |
| SRP1649-E10 | 2.81E+05 | 1.40E−02 | 4.97E−08 | 0.2 | 7.4 | Not tested |
| SRP1649-F06 | 2.27E+05 | 3.93E−03 | 1.73E−08 | 0.2 | 5.6 | 0.63 |
| SRP1649-G08 | 1.91E+05 | 2.43E−03 | 1.28E−08 | 0.2 | 9.3 | Not tested |
| SRP1649-H02 | 1.57E+05 | 3.74E−03 | 2.39E−08 | 0.2 | 2.2 | Not tested |

Example 11: Preparation of scFvs

A single-chain antibody is made in either the $V_H V_L$ or $V_L V_H$ orientation with a linker sequence between the $V_H$ and $V_L$ domains. Typically scFv linkers are composed of (GGGGS)n (SEQ ID NO: 175) repeats where n=3, 4, 5, or 6 for linkers of 15, 20, 25, or 30 residues respectively. For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 168). C-terminal affinity tags can optionally be added to facilitate purification and assay development. An exemplary affinity tag is a C-terminal FlagHis tag GSGDYKDDDDKGSGHHHHHH (SEQ ID NO:166). A stop codon is typically inserted at the end of the sequence. An exemplary scFv of the present disclosure is SEQ ID NO:169, with an N-terminal Met residue, a $V_H$ domain, a GGGGSGGGGSGGGGS (SEQ ID NO: 167) linker, a $V_L$ domain, an AAGSDQEPKSS (SEQ ID NO: 168) linker, an Fc domain, a FlagHis tag, and a stop codon.

Example 9: Sequences

Table 10 provides sequences referred to herein.

TABLE 10

| SEQ ID NO: | Molecule | Region | Scheme | Sequence |
|---|---|---|---|---|
| 1 | Human Tim-3 | | | MFSHLPFDCVLLLLLLLLTRSSEVEYRA EVGQNAYLPCFYTPAAPGNLVPVCWGKG ACPVFECGNVVLRTDERDVNYWTSRYWL NGDFRKGDVSLTIENVILADSGIYCCRI QIPGIMNDEKFNLKLVIKPAKVTPAPTL QRDFTAAFPRMLTTRGHGPAETQTLGSL PDINLTQISTLANELRDSRLANDLRDSG ATIRIGIYIGAGICAGLALALIFGALIF KWYSHSKEKIQNLSLISLANLPPSGLAN |

TABLE 10-continued

Sequences

| SEQ ID NO: | Molecule | Region | Scheme | Sequence |
|---|---|---|---|---|
| | | | | AVAEGIRSEENIYTIEENVYEVEEPNEYYCYVSSRQQPSQPLGCRFAMP |
| 2 | Cynomolgus Tim-3 | | | MFSHLPFDCVLLLLLLLLTRSSEVEYIAEVGQNAYLPCSYTPAPPGNLVPVCWGKGACPVFDCSNVVLRTDNRDVNDRTSGRYWLKGDFHKGDVSLTIENVTLADSGVYCCRIQIPGIMNDEKHNVKLVVIKPAKVTPAPTLQRDLTSAFPRMLTTGEHGPAETQTPGSLPDVNLTVSNFFCELQIFTLTNELRDSGATIRTAIYIAAGISAGLALALIFGALIFKWYSHSKEKTQNLSISLANIPPSGLANAVAEGIRSEENIYTIEEDVYEVEEPNEYYCYVSSGQQPSQPLGCRVAMP |
| 3 | Mouse Tim-3 | | | MFSGLTLNCVLLLLQLLLARSLENAYVFEVGKNAYLPCSYTLSTPGALVPMCWGKGFCPWSQCTNELLRTDERNVTYQKSSRYQLKGDLNKGDVSLIIKNVTLDDHGTYCCRIQFPGLMNDKKLELKLDIKAAKVTPAQTAHGDSTTASPRTLTTERNGSETQTLVTLHNNNGTKISTWADEIKDSGETIRTAIHIGVGVSAGLTLALIIGVLILKWYSCKKKKLSSLSLITLANLPPGGLANAGAVRIRSEENIYTIEENVYEVENSNEYYCYVNSQQPS |
| 4 | h22E11-VH5-51-VH | CDR-H1 | Chothia | GFSLTSY |
| 5 | h22E11-VH1-69-VH | CDR-H1 | Chothia | GFSLTSY |
| 6 | 22E11-VH | CDR-H1 | Chothia | GFSLTSY |
| 7 | h22E11-VH4-30-4-VH | CDR-H1 | Chothia | GFSLTSY |
| 8 | h22E11-VH3-23-VH | CDR-H1 | Chothia | GFSLTSY |
| 9 | h22E11-5-VH | CDR-H1 | Chothia | GFSLTSY |
| 10 | 2D5-VH | CDR-H1 | Chothia | GYPFIGY |
| 11 | SRP1649-A01 | CDR-H1 | Chothia | GFNISRY |
| 12 | SRP1649-F06 | CDR-H1 | Chothia | GFNIGNY |
| 13 | SRP1649-G08 | CDR-H1 | Chothia | GFNISNY |
| 14 | SRP1649-C05 | CDR-H1 | Chothia | GFNIGKH |
| 15 | SRP1649-D11 | CDR-H1 | Chothia | GFNISGY |
| 16 | SRP1497-A02 | CDR-H1 | Chothia | GFNISNY |
| 17 | SRP1497-A01 | CDR-H1 | Chothia | GFNISNY |
| 18 | SRP1497-A05 | CDR-H1 | Chothia | GFNISNY |
| 19 | SRP1649-B06 | CDR-H1 | Chothia | GFNISNH |
| 20 | SRP1649-D06 | CDR-H1 | Chothia | GFNIRNH |
| 21 | SRP1649-H02 | CDR-H1 | Chothia | GFNIRSY |
| 22 | SRP1649-B09 | CDR-H1 | Chothia | GFNIRNN |
| 23 | SRP1649-E10 | CDR-H1 | Chothia | GFNISNN |
| 24 | SRP1649-E08 | CDR-H1 | Chothia | GFSISNY |
| 25 | h22E11-VH5-51-VH | CDR-H1 | Kabat | SYGVH |
| 26 | h22E11-VH1-69-VH | CDR-H1 | Kabat | SYGVH |
| 27 | 22E11-VH | CDR-H1 | Kabat | SYGVH |

TABLE 10-continued

Sequences

| SEQ ID NO: | Molecule | Region | Scheme | Sequence |
|---|---|---|---|---|
| 28 | h22E11-VH4-30-4-VH | CDR-H1 | Kabat | SYGVH |
| 29 | h22E11-VH3-23-VH | CDR-H1 | Kabat | SYGVH |
| 30 | h22E11-5-VH | CDR-H1 | Kabat | SYGVH |
| 31 | 2D5-VH | CDR-H1 | Kabat | GYTMN |
| 32 | SRP1649-A01 | CDR-H1 | Kabat | RYYIH |
| 33 | SRP1649-F06 | CDR-H1 | Kabat | NYAIH |
| 34 | SRP1649-G08 | CDR-H1 | Kabat | NYVIH |
| 35 | SRP1649-C05 | CDR-H1 | Kabat | KHVIH |
| 36 | SRP1649-D11 | CDR-H1 | Kabat | GYVIH |
| 37 | SRP1497-A02 | CDR-H1 | Kabat | NYAIH |
| 38 | SRP1497-A01 | CDR-H1 | Kabat | NYAIH |
| 39 | SRP1497-A05 | CDR-H1 | Kabat | NYAIH |
| 40 | SRP1649-B06 | CDR-H1 | Kabat | NHAIH |
| 41 | SRP1649-D06 | CDR-H1 | Kabat | NHAIH |
| 42 | SRP1649-H02 | CDR-H1 | Kabat | SYAIH |
| 43 | SRP1649-B09 | CDR-H1 | Kabat | NNAIH |
| 44 | SRP1649-E10 | CDR-H1 | Kabat | NNVIH |
| 45 | SRP1649-E08 | CDR-H1 | Kabat | NYVIH |
| 46 | h22E11-VH5-51-VH | CDR-H2 | Chothia | WS-DGS |
| 47 | h22E11-VH1-69-VH | CDR-H2 | Chothia | WS-DGS |
| 48 | 22E11-VH | CDR-H2 | Chothia | WS-DGS |
| 49 | h22E11-VH4-30-4-VH | CDR-H2 | Chothia | WS-DGS |
| 50 | h22E11-VH3-23-VH | CDR-H2 | Chothia | WS-DGS |
| 51 | h22E11-5-VH | CDR-H2 | Chothia | WS-DGS |
| 52 | 2D5-VH | CDR-H2 | Chothia | NPYNGI |
| 53 | SRP1649-A01 | CDR-H2 | Chothia | TPVRGY |
| 54 | SRP1649-F06 | CDR-H2 | Chothia | TPGQGY |
| 55 | SRP1649-G08 | CDR-H2 | Chothia | TPDGGI |
| 56 | SRP1649-C05 | CDR-H2 | Chothia | VPNGGY |
| 57 | SRP1649-D11 | CDR-H2 | Chothia | IPTAGY |
| 58 | SRP1497-A02 | CDR-H2 | Chothia | TPDGGY |
| 59 | SRP1497-A01 | CDR-H2 | Chothia | TPDGGY |
| 60 | SRP1497-A05 | CDR-H2 | Chothia | TPDGGY |
| 61 | SRP1649-B06 | CDR-H2 | Chothia | SPAVGY |
| 62 | SRP1649-D06 | CDR-H2 | Chothia | APAGGY |
| 63 | SRP1649-H02 | CDR-H2 | Chothia | TPAGGD |
| 64 | SRP1649-B09 | CDR-H2 | Chothia | TPAGGY |
| 65 | SRP1649-E10 | CDR-H2 | Chothia | MPGGGS |

TABLE 10-continued

Sequences

| SEQ ID NO: | Molecule | Region | Scheme | Sequence |
|---|---|---|---|---|
| 66 | SRP1649-E08 | CDR-H2 | Chothia | SPDGGF |
| 67 | h22E11-VH5-51-VH | CDR-H2 | Kabat | VIWS-DGSTTYNPSFQG |
| 68 | h22E11-VH1-69-VH | CDR-H2 | Kabat | VIWS-DGSTTYNQKFQG |
| 69 | 22E11-VH | CDR-H2 | Kabat | VIWS-DGSTTYNSALKS |
| 70 | h22E11-VH4-30-4-VH | CDR-H2 | Kabat | VIWS-DGSTTYNPSLKS |
| 71 | h22E11-VH3-23-VH | CDR-H2 | Kabat | VIWS-DGSTTYNDSVKG |
| 72 | h22E11-5-VH | CDR-H2 | Kabat | VIWS-DGSTTYNSALKS |
| 73 | 2D5-VH | CDR-H2 | Kabat | LINPYNGITTYNQKFKG |
| 74 | SRP1649-A01 | CDR-H2 | Kabat | GITPVRGYTEYADSVKD |
| 75 | SRP1649-F06 | CDR-H2 | Kabat | DITPGQGYTEYADSVKD |
| 76 | SRP1649-G08 | CDR-H2 | Kabat | AITPDGGITEYADSVKG |
| 77 | SRP1649-C05 | CDR-H2 | Kabat | DIVPNGGYTEYADSVKD |
| 78 | SRP1649-D11 | CDR-H2 | Kabat | DIIPTAGYTEYADSVKG |
| 79 | SRP1497-A02 | CDR-H2 | Kabat | DITPDGGYTDYADSVKG |
| 80 | SRP1497-A01 | CDR-H2 | Kabat | DITPDGGYTDYADSVKG |
| 81 | SRP1497-A05 | CDR-H2 | Kabat | DITPDGGYTDYADSVKD |
| 82 | SRP1649-B06 | CDR-H2 | Kabat | DISPAVGYTDYADSVKD |
| 83 | SRP1649-D06 | CDR-H2 | Kabat | DIAPAGGYTDYADSVKD |
| 84 | SRP1649-H02 | CDR-H2 | Kabat | DITPAGGDTEYADSVKG |
| 85 | SRP1649-B09 | CDR-H2 | Kabat | DITPAGGYTGYADSVKD |
| 86 | SRP1649-E10 | CDR-H2 | Kabat | DIMPGGGSTDYADSVKD |
| 87 | SRP1649-E08 | CDR-H2 | Kabat | DISPDGGFTDYADSVKD |
| 88 | h22E11-VH5-51-VH | CDR-H3 | | QGGYR-YDDAMDY |
| 89 | h22E11-VH1-69-VH | CDR-H3 | | QGGYR-YDDAMDY |
| 90 | 22E11-VH | CDR-H3 | | QGGYR-YDDAMDY |
| 91 | h22E11-VH4-30-4-VH | CDR-H3 | | QGGYR-YDDAMDY |
| 92 | h22E11-VH3-23-VH | CDR-H3 | | QGGYR-YDDAMDY |
| 93 | h22E11-5-VH | CDR-H3 | | QGGYR-YDDAMDY |
| 94 | 2D5-VH | CDR-H3 | | SFFYGSSNDWLVY |
| 95 | SRP1649-A01 | CDR-H3 | | GYVYR-MWDSYDY |
| 96 | SRP1649-F06 | CDR-H3 | | GYVYR-MWDSYDY |
| 97 | SRP1649-G08 | CDR-H3 | | GYVYR-MWDSYDY |
| 98 | SRP1649-C05 | CDR-H3 | | GYVYR-MWDSFDY |
| 99 | SRP1649-D11 | CDR-H3 | | GYVYR-MWDSFDY |
| 100 | SRP1497-A02 | CDR-H3 | | GYVYR-MWDSFDY |
| 101 | SRP1497-A01 | CDR-H3 | | GYVYR-MWDSFDY |
| 102 | SRP1497-A05 | CDR-H3 | | GYVYR-MWDSFDY |

TABLE 10-continued

Sequences

| SEQ ID NO: | Molecule | Region | Scheme | Sequence |
|---|---|---|---|---|
| 103 | SRP1649-B06 | CDR-H3 | | GYVYR-MWDSFDH |
| 104 | SRP1649-D06 | CDR-H3 | | GYVYR-MWDSYDY |
| 105 | SRP1649-H02 | CDR-H3 | | GYIYR-MWDSYDY |
| 106 | SRP1649-B09 | CDR-H3 | | GYIYR-MWDSLDY |
| 107 | SRP1649-E10 | CDR-H3 | | GYVYR-MWDSYDY |
| 108 | SRP1649-E08 | CDR-H3 | | GHVYR-LWDSFDY |
| 109 | h22E11-Vk3-11-VL | CDR-L1 | | KASQSVDYD-GNSYVN |
| 110 | h22E11-5-VL | CDR-L1 | | KASQSVDYD-GNSYVA |
| 111 | h22E11-Vk1-39-VL | CDR-L1 | | KASQSVDYD-GNSYVN |
| 112 | h22E11-Vk4-1-VL | CDR-L1 | | KASQSVDYD-GNSYVN |
| 113 | 22E11-VL | CDR-L1 | | KASQSVDYD-GNSYVN |
| 114 | h22E11-Vk2-28-VL | CDR-L1 | | KASQSVDYD-GNSYVN |
| 115 | 2D5-VL | CDR-L1 | | RSSQSIVHTNGNTYLE |
| 116 | h22E11-Vk3-11-VL | CDR-L2 | | AASNLES |
| 117 | h22E11-5-VL | CDR-L2 | | AASNLES |
| 118 | h22E11-Vk1-39-VL | CDR-L2 | | AASNLES |
| 119 | h22E11-Vk4-1-VL | CDR-L2 | | AASNLES |
| 120 | 22E11-VL | CDR-L2 | | AASNLES |
| 121 | h22E11-Vk2-28-VL | CDR-L2 | | AASNLES |
| 122 | 2D5-VL | CDR-L2 | | KVSNRFS |
| 123 | h22E11-Vk3-11-VL | CDR-L3 | | QQSNEDPYT |
| 124 | h22E11-5-VL | CDR-L3 | | QQSNEDPYT |
| 125 | h22E11-Vk1-39-VL | CDR-L3 | | QQSNEDPYT |
| 126 | h22E11-Vk4-1-VL | CDR-L3 | | QQSNEDPYT |
| 127 | 22E11-VL | CDR-L3 | | QQSNEDPYT |
| 128 | h22E11-Vk2-28-VL | CDR-L3 | | QQSNEDPYT |
| 129 | 2D5-VL | CDR-L3 | | FQGSHVPWT |
| 130 | 2D5-VH | VH | | EVQLQQSGPELVKPGTSMKISCRASGYPFIGYTMNWVKQSHGGNLEWIGLINPYNGITTYNQKFKGRATLSVDTSSTIAYMELLSLTSDDSAEYYCARSFFYGSSNDWLVYWGQGTLVTVSA |
| 131 | 22E11-VH | VH | | QVQLKESGPDLVAPSQSLSITCTVSGFSLTSYGVHWVRQPPGKGLEWLVVIWSDGSTTYNSALKSRLTISKDNSKSQVFLKMNSLQTDDTAMYYCARQGGYRYDDAMDYWGQGTSVAVSS |
| 132 | h22E11-VH5-51-VH | VH | | EVQLVQSGAEVKKPGESLKISCKVSGFSLTSYGVHWVRQMPGKGLEWLVVIWSDGSTTYNPSFQGQVTISKDKSISTVYLQWSSLKASDTAMYYCARQGGYRYDDAMDYWGQGTLVTVSS |

TABLE 10-continued

Sequences

| SEQ ID NO: | Molecule | Region | Scheme | Sequence |
|---|---|---|---|---|
| 133 | h22E11-VH4-30-4-H | VH | | QVQLQESGPGLVKPSQTLSLTCTVSGFSLTSYGVHWIRQPPGKGLEWLVVIWSDGSTTYNPSLKSRVTISKDTSKNQVSLKLSSVTAADTAVYYCARQGGYRYDDAMDYWGQGTLVTVSS |
| 134 | h22E11-VH3-23-VH | VH | | EVQLLESGGGLVQPGGSLRLSCAVSGFSLTSYGVHWVRQAPGKGLEWLVVIWSDGSTTYNDSVKGRFTISKDNSKNTVYLQMNSLRAEDTAVYYCARQGGYRYDDAMDYWGQGTLVTVSS |
| 135 | h22E11-VH1-69-VH | VH | | QVQLVQSGAEVKKPGSSVKVSCKVSGFSLTSYGVHWVRQAPGQGLEWLVVIWSDGSTTYNQKFQGRVTITKDESTSTVYMELSSLRSEDTAVYYCARQGGYRYDDAMDYWGQGTLVTVSS |
| 136 | h22E11-5-VH | VH | | EVQLVESGGGLVQPGGSLRLSCAVSGFSLTSYGVHWVRQAPGKGLEWLVVIWSDGSTTYNSALKSRFTISKDNAKNSVYLQMNSLRAEDTAVYYCARQGGYRYDDAMDYWGQGTLVTVSS |
| 137 | SRP1649-A01 | VH | | EVQLVESGGGLVQPGGSLRLSCAASGFNISRYYIHWVRQAPGKGLEWVAGITPVRGYTEYADSVKDRFTISADTSKNTAYLQMNSLRAEDTAVYYCARGYVYRMWDSYDYWGQGTLVTVSS |
| 138 | SRP1649-B06 | VH | | EVQLVESGGGLVQPGGSLRLSCAASGFNISNHAIHWVRQAPGKGLEWVADISPAVGYTDYADSVKDRFTISADTSKNTAYLQMNSLRAEDTAVYYCARGYVYRMWDSFDHWGQGTLVTVSS |
| 139 | SRP1649-C05 | VH | | EVQLVESGGGLVQPGGSLRLSCAASGFNIGKHVIHWVRQAPGKGLEWVADIVPNGGYTEYADSVKDRFTISADTSKNTAYLQMNSLRAEDTAVYYCARGYVYRMWDSFDYWGQGTLVTVSS |
| 140 | SRP1649-D06 | VH | | EVQLVESGGGLVQPGGSLRLSCAASGFNIRNHAIHWVRQAPGKGLEWVADIAPAGGYTDYADSVKDRFTISADTSKNTAYLQMNSLRAEDTAVYYCARGYVYRMWDSYDYWGQGTLVTVSS |
| 141 | SRP1649-D11 | VH | | EVQLVESGGGLVQPGGSLRLSCAASGFNISGYVIHWVRQAPGKGLEWVADIIPTAGYTEYADSVKGRFTISADTSKNTAYLQMNSLRAEDTAVYYCARGYVYRMWDSFDYWGQGTLVTVSS |
| 142 | SRP1649-E08 | VH | | EVQLVESGGSLVQPGGSLRLSCAASGFSISNYVIHWVRQAPGKGLEWVADISPDGGFTDYADSVKDRFTISADTSKNTAYLQMNSLRAEDTAVYYCARGHVYRLWDSFDYWGRGTLVTVSS |
| 143 | SRP1649-E10 | VH | | EVQLVESGGGLVQPGGSLRLSCAASGFNISNNVIHWVRQAPGKGLEWVGDIMPGGGSTDYADSVKDRFTISADTSKNTAYLQMNSLRAEDTAVYYCARGYVYRMWDSYDYWGQGTLVTVSS |
| 144 | SRP1649-F06 | VH | | EVQLVESGGGLVQPGGSLRLSCAASGFNIGNYAIHWVRQAPGKGLEWVADITPGQGYTEYADSVKDRFTISADTSKNTAYLQMNSLRAEDTAVYYCARGYVYRMWDSYDYWGQGTLVTVSS |

TABLE 10-continued

Sequences

| SEQ ID NO: | Molecule | Region | Scheme | Sequence |
|---|---|---|---|---|
| 145 | SRP1649-G08 | VH | | EVQLVESGGGLVQPGGSLRLSCAASGFN ISNYVIHWVRQAPGKGLEWVAAITPDGG ITEYADSVKGRFAISADTSKNTAYLQMN SLRAEDTAVYYCARGYVYRMWDSYDYWG QGTLVTVSS |
| 146 | SRP1649-H02 | VH | | EVQLVESGGGLVQPGGSLRLSCAASGFN IRSYAIHWVRQAPGKGLEWVADITPAGG DTEYADSVKGRFTISADTSKNTAYLQMN SLRAEDTAVYYCARGYIYRMWDSYDYWG QGTLVTVSS |
| 147 | SRP1649-B09 | VH | | EVQLVESGGGLVQPGGSLRLSCAASGFN IRNNAIHWVRQAPGKGLEWVADITPAGG YTGYADSVKDRFTISADTSKNTAYLQMN SLRAEDTAVYYCARGYIYRMWDSLDYWG QGTLVTVSS |
| 148 | SRP1497-A05 | VH | | EVQLVESGGGLVQPGGSLRLSCAASGFN ISNYAIHWVRQAPGKGLEWVADITPDGG YTDYADSVKDRFTISADTSKNTAYLQMN SLRAEDTAVYYCARGYVYRMWDSFDYWG QGTLVTVSS |
| 149 | SRP1497-A02 | VH | | EVQLVESGGGLVRPGGSLRLSCAASGFN ISNYAIHWVRQAPGKGLEWVADITPDGG YTDYADSVKGRFTISADTSKNTAYLQMN SLRAEDTAVYYCARGYVYRMWDSFDYWG QGTLVTVSS |
| 150 | SRP1497-A01 | VH | | EVQLVESGGGLVQPGGSLRLSCAASGFN ISNYAIHWVRQAPGKGLEWVADITPDGG YTDYADSVKGRFTISADTSKNTAYLQMN SLRAEDTAVYYCARGYVYRMWDSFDYWG QGTLVTVSS |
| 151 | 2D5-VL | VL | | DVLMTQTPLSLPVSLGDQASISCRSSQS IVHTNGNTYLEWYLQKPGQSPKLLIYKV SNRFSGVPDRFSGSGSGTDFTLKISRVE AEDLGVYYCFQGSHVPWTFGGGTELEIK |
| 152 | 22E11-VL | VL | | DIVLTQSPASLAVSLGQRATISCKASQS VDYDGNSYVNWYQQKPGQPPKLLIYAAS NLESGIPARESGSGSGTDFTLNIHPVEE EDAATYYCQQSNEDPYTFGGGTKLEIK |
| 153 | h22E11-Vk4-1-VL | VL | | DIVLTQSPDSLAVSLGERATINCKASQS VDYDGNSYVNWYQQKPGQPPKLLIYAAS NLESGVPDRFSGSGSGTDFTLTISSLQA EDVAVYYCQQSNEDPYTFGQGTKVEIK |
| 154 | h22E11-Vk3-11-VL | VL | | EIVLTQSPATLSLSPGERATLSCKASQS VDYDGNSYVNWYQQKPGQAPRLLIYAAS NLESGIPARFSGSGSGTDFTLTISSLEP EDFAVYYCQQSNEDPYTFGQGTKVEIK |
| 155 | h22E11-Vk2-28-VL | VL | | DIVLTQSPLSLPVTPGEPASISCKASQS VDYDGNSYVNWYLQKPGQSPQLLIYAAS NLESGVPDRFSGSGSGTDFTLKISRVEA EDVGVYYCQQSNEDPYTFGQGTKVEIK |
| 156 | h22E11-Vk1-39-VL | VL | | DIQLTQSPSSLSASVGDRVTITCKASQS VDYDGNSYVNWYQQKPGKAPKLLIYAAS NLESGVPSRFSGSGSGTDFTLTISSLQP EDFATYYCQQSNEDPYTFGQGTKVEIK |
| 157 | h22E11-5-VL | VL | | EIVLTQSPGTLSLSPGERATLSCKASQS VDYDGNSYVAWYQQKPGQAPRLLIYAAS NLESGIPDRFSGSGSGTDFTLTISRLEP EDFAVYYCQQSNEDPYTFGQGTKVEIK |
| 158 | trastuzumab VL | VL | | DIQMTQSPSSLSASVGDRVTITCRASQD VNTAVAWYQQKPGKAPKLLIYSASFLYS GVPSRFSGSRSGTDFTLTISSLQPEDFA TYYCQQHYTTPPTFGQGTKVEIK |

TABLE 10-continued

Sequences

| SEQ ID NO: | Molecule | Region | Scheme | Sequence |
|---|---|---|---|---|
| 159 | Human IgG1 HC Constant | | | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLEPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSREEMTKNQVSLTCLV KGFYPSDIAVEWESNGQPENNYKTTPPV LDSDGSFFLYSKLTVDKSRWQQGNVFSC SVMHEALHNHYTQKSLSLSPGK |
| 160 | Human IgG LC Constant Ckappa | | | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 161 | Mouse IgG1 HC Constant | | | AKTTPPSVYPLAPGSAAQTNSMVTLGCL VKGYFPEPVTVTWNSGSLSSGVHTFPAV LQSDLYTLSSSVTVPSSTWPSETVTCNV AHPASSTKVDKKIVPRDCGCKPCICTVP EVSSVFIFPPKPKDVLTITLTPKVTCVV VDISKDDPEVQFSWFVDDVEVHTAQTQP REEQFNSTERSVSELPIMHQDWLNGKEF KCRVNSAAFPAPIEKTISKTKGRPKAPQ VYTIPPPKEQMAKDKVSLTCMITDFFPE DITVEWQWNGQPAENYKNTQPIMDTDGS YFVYSKLNVQKSNWEAGNTFTCSVLHEG LHNHHTEKSLSHSPG |
| 162 | Mouse IgG LC Constant Ckappa | | | RADAAPTVSIFPPSSEQLTSGGASVVCF LNNFYPKDINVKWKIDGSERQNGVLNSW TDQDSKDSTYSMSSTLTLTKDEYERHNS YTCEATHKTSTSPIVKSFNRNEC |
| 163 | Kappa LC | | | HMTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 164 | Lambda LD | | | GQPKAAPSVTLFPPSSEELQANKATLVC LISDFYPGAVTVAWKADSSPVKAGVETT TPSKQSNNKYAASSYLSLTPEQWKSHRS YSCQVTHEGSTVEKTVAPTECS |
| 165 | IgG1 Fc from scFv-Fc | | | AAGSDQEPKSSDKTHTCPPCSAPELLGG SSVFLEPPKPKDTLMISRTPEVTCVVVD VSHEDPEVKFNWYVDGVEVHNAKTKPRE EQYNSTYRVVSVLTVLHQDWLNGKEYKC KVSNKALPAPIEKTISKAKGQPREPQVY TLPPSRDELTKNQVSLTCLVKGFYPSDI AVEWESNGQPENNYKTTPPVLDSDGSFF LYSKLTVDKSRWQQGNVFSCSVMHEALH NHYTQKSLSLSPGKGSGDYKDDDDKGSG |
| 166 | FlagHis Tag | | | GSGDYKDDDDKGSGHHHHHH |
| 167 | Linker | | | GGGGSGGGGSGGGGS |
| 168 | Linker | | | AAGSDQEPKSS |
| 169 | scFv-Fc | | | MEVQLVQSGAEVKKPGESLKISCKVSGF SLTSYGVHWVRQMPGKGLEWLVVIWSDG STTYNPSFQGQVTISKDKSISTVYLQWS SLKASDTAMYYCARQGGYRYDDAMDYWG QGTLVTVSSGGGGSGGGGSGGGGSDIQL TQSPSSLSASVGDRVTITCKASQSVDYD GNSYVNWYQQKPGKAPKLLIYAASNLES GVPSRFSGSGSGTDFTLTISSLQPEDFA TYYCQQSNEDPYTFGQGTKVEIKAAGSD QEPKSSDKTHTCPPCPAPELLGGPSVFL FPPKPKDTLMISRTPEVTCVVVDVSHED PEVKFNWYVDGVEVHNAKTKPREEQYNS |

TABLE 10-continued

Sequences

| SEQ ID NO: | Molecule | Region Scheme | Sequence |
|---|---|---|---|
| | | | TYRVVSVLTVLHQDWLNGKEYKCKVSNK ALPAPIEKTISKAKGQPREPQVYTLPPS REEMTKNQVSLTCLVKGFYPSDIAVEWE SNGQPENNYKTTPPVLDSDGSFFLYSKL TVDKSRWQQGNVFSCSVMHEALHNHYTQ KSLSLSPGKGSGDYKDDDDKGSGHHHHH H |
| 170 | CDR H3 consensus sequence | | G$\beta_2\beta_3$YR$\beta_7$WDS$\beta_{11}$D$\beta_{13}$ |
| 171 | CDR H1 Chothia consensus sequence | | GFNI$\delta_5\delta_6\delta_7$ |
| 172 | CDRH2 Kabat consensus sequence (1) | | VIWSDGSTTN$\theta_{13}\theta_{14}\theta_{15}\theta_{16}\theta_{17}$ |
| 173 | CDRH2 Kabat consensus sequence (2) | | $\theta_1$I$\theta_3$P$\theta_5\theta_6$G$\theta_8$T$\theta_{10}$YADSVK$\theta_{17}$ |
| 174 | CDR L1 consensus sequence | | KASSQVDYDGNSYV$\mu_{16}$ |
| 175 | scFV linker sequence | | GGGGSGGGGSGGGGSGGGGSGGGGSGGG S |
| 176 | Trastuzumab CDR L1 | | RASQDVNTAVA |
| 177 | Trastuzumab CDR L2 | | SASFLYS |
| 178 | Trastuzumab CDR L3 | | QQHYTTPPT |

Equivalents

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An isolated antibody that specifically binds to human Tim-3, wherein the antibody comprises:
   a. a $V_H$ comprising: a CDR-H1 comprising SEQ ID NOs: 4 or 25; a CDR-H2 comprising SEQ ID NOs: 46 or 67; and a CDR-H3 comprising SEQ ID NO: 88; a $V_L$ comprising: a CDR-L1 comprising SEQ ID NO: 112; a CDR-L2 comprising SEQ ID NO: 119; and a CDR-L3 comprising SEQ ID NO: 126;
   b. a $V_H$ comprising: a CDR-H1 comprising SEQ ID NOs: 5 or 26; a CDR-H2 comprising SEQ ID NOs: 47 or 68; and a CDR-H3 comprising SEQ ID NO: 89; a $V_L$ comprising: a CDR-L1 comprising SEQ ID NO: 111; a CDR-L2 comprising SEQ ID NO: 118; and a CDR-L3 comprising SEQ ID NO: 125;
   c. a $V_H$ comprising: a CDR-H1 comprising SEQ ID NOs: 6 or 27; a CDR-H2 comprising SEQ ID NOs: 48 or 69; and a CDR-H3 comprising SEQ ID NO: 90; a $V_L$ comprising: a CDR-L1 comprising SEQ ID NO: 113; a CDR-L2 comprising SEQ ID NO: 120; and a CDR-L3 comprising SEQ ID NO: 127;
   d. a $V_H$ comprising: a CDR-H1 comprising SEQ ID NOs: 7 or 28; a CDR-H2 comprising SEQ ID NOs: 49 or 70; and a CDR-H3 comprising SEQ ID NO: 91; a $V_L$ comprising: a CDR-L1 comprising SEQ ID NO: 109; a CDR-L2 comprising SEQ ID NO: 116; and a CDR-L3 comprising SEQ ID NO: 123;
   e. a $V_H$ comprising: a CDR-H1 comprising SEQ ID NOs: 8 or 29; a CDR-H2 comprising SEQ ID NOs: 50 or 71; and a CDR-H3 comprising SEQ ID NO: 92; a $V_L$ comprising: a CDR-L1 comprising SEQ ID NO: 114; a CDR-L2 comprising SEQ ID NO: 121; and a CDR-L3 comprising SEQ ID NO: 128; or 28;
   f. a $V_H$ comprising: a CDR-H1 comprising SEQ ID NOs: 9 or 30; a CDR-H2 comprising SEQ ID NOs: 51 or 72; and a CDR-H3 comprising SEQ ID NO: 93; a $V_L$ comprising: a CDR-L1 comprising SEQ ID NO: 110; a CDR-L2 comprising SEQ ID NO: 117; and a CDR-L3 comprising SEQ ID NO: 124;
   g. a $V_H$ comprising: a CDR-H1 comprising SEQ ID NOs: 10 or 31; a CDR-H2 comprising SEQ ID NOs: 52 or 73; and a CDR-H3 comprising SEQ ID NO: 94; a $V_L$ comprising: a CDR-L1 comprising SEQ ID NO: 115; a CDR-L2 comprising SEQ ID NO: 122; and a CDR-L3 comprising SEQ ID NO: 129;
   h. a $V_H$ comprising: a CDR-H1 comprising SEQ ID NOs: 11 or 32; a CDR-H2 comprising SEQ ID NOs: 53 or 74; and a CDR-H3 comprising SEQ ID NO: 95; and the $V_L$ region comprises a CDR L1 comprising SEQ ID NO: 176; a CDR L2 sequence comprising SEQ ID NO: 177, and a CDR L3 sequence comprising SEQ ID NO: 178;
   i. a $V_H$ comprising: a CDR-H1 comprising SEQ ID NOs: 12 or 33; a CDR-H2 comprising SEQ ID NOs: 54 or 75; and a CDR-H3 comprising SEQ ID NO: 96; and the $V_L$ region comprises a CDR L1 comprising SEQ ID NO: 176; a CDR L2 sequence comprising SEQ ID NO: 177, and a CDR L3 sequence comprising SEQ ID NO: 178;
   j. a $V_H$ comprising: a CDR-H1 comprising SEQ ID NOs: 13 or 34; a CDR-H2 comprising SEQ ID NOs: 55 or 76; and a CDR-H3 comprising SEQ ID NO: 97; and the $V_L$ region comprises a CDR L1 comprising SEQ ID NO: 176; a CDR L2 sequence comprising SEQ ID NO: 177, and a CDR L3 sequence comprising SEQ ID NO: 178;
   k. a $V_H$ comprising: a CDR-H1 comprising SEQ ID NOs: 14 or 35; a CDR-H2 comprising SEQ ID NOs: 56 or 77; and a CDR-H3 comprising SEQ ID NO: 98; and the $V_L$ region comprises a CDR L1 comprising SEQ ID NO: 176; a CDR L2 sequence comprising SEQ ID NO: 177, and a CDR L3 sequence comprising SEQ ID NO: 178;
   l. a $V_H$ comprising: a CDR-H1 comprising SEQ ID NOs: 15 or 36; a CDR-H2 comprising SEQ ID NOs: 57 or 78; and a CDR-H3 comprising SEQ ID NO: 99; and the $V_L$ region comprises a CDR L1 comprising SEQ ID NO: 176; a CDR L2 sequence comprising SEQ ID NO: 177, and a CDR L3 sequence comprising SEQ ID NO: 178;

m. a V_H comprising: a CDR-H1 comprising SEQ ID NOs: 16 or 37; a CDR-H2 comprising SEQ ID NOs: 58 or 79; and a CDR-H3 comprising SEQ ID NO: 100; and the V_L region comprises a CDR L1 comprising SEQ ID NO: 176; a CDR L2 sequence comprising SEQ ID NO: 177, and a CDR L3 sequence comprising SEQ ID NO: 178;

n. a V_H comprising: a CDR-H1 comprising SEQ ID NOs: 17 or 38; a CDR-H2 comprising SEQ ID NOs: 59 or 80; and a CDR-H3 comprising SEQ ID NO: 101; and the V_L region comprises a CDR L1 comprising SEQ ID NO: 176; a CDR L2 sequence comprising SEQ ID NO: 177, and a CDR L3 sequence comprising SEQ ID NO: 178;

o. a V_H comprising: a CDR-H1 comprising SEQ ID NOs: 18 or 39; a CDR-H2 comprising SEQ ID NOs: 60 or 81; and a CDR-H3 comprising SEQ ID NO: 102; and the V_L region comprises a CDR L1 comprising SEQ ID NO: 176; a CDR L2 sequence comprising SEQ ID NO: 177, and a CDR L3 sequence comprising SEQ ID NO: 178;

p. a V_H comprising: a CDR-H1 comprising SEQ ID NOs: 19 or 40; a CDR-H2 comprising SEQ ID NOs: 61 or 82; and a CDR-H3 comprising SEQ ID NO: 103; and the V_L region comprises a CDR L1 comprising SEQ ID NO: 176; a CDR L2 sequence comprising SEQ ID NO: 177, and a CDR L3 sequence comprising SEQ ID NO: 178;

q. a V_H comprising: a CDR-H1 comprising SEQ ID NOs: 20 or 41; a CDR-H2 comprising SEQ ID NOs: 62 or 83; and a CDR-H3 comprising SEQ ID NO: 104; and the V_L region comprises a CDR L1 comprising SEQ ID NO: 176; a CDR L2 sequence comprising SEQ ID NO: 177, and a CDR L3 sequence comprising SEQ ID NO: 178;

r. a V_H comprising: a CDR-H1 comprising SEQ ID NOs: 21 or 42; a CDR-H2 comprising SEQ ID NOs: 63 or 84; and a CDR-H3 comprising SEQ ID NO: 105; and the V_L region comprises a CDR L1 comprising SEQ ID NO: 176; a CDR L2 sequence comprising SEQ ID NO: 177, and a CDR L3 sequence comprising SEQ ID NO: 178;

s. a V_H comprising: a CDR-H1 comprising SEQ ID NOs: 22 or 43; a CDR-H2 comprising SEQ ID NOs: 64 or 85; and a CDR-H3 comprising SEQ ID NO: 106; and the V_L region comprises a CDR L1 comprising SEQ ID NO: 176; a CDR L2 sequence comprising SEQ ID NO: 177, and a CDR L3 sequence comprising SEQ ID NO: 178;

t. a V_H comprising: a CDR-H1 comprising SEQ ID NOs: 23 or 44; a CDR-H2 comprising SEQ ID NOs: 65 or 86; and a CDR-H3 comprising SEQ ID NO: 107; and the V_L region comprises a CDR L1 comprising SEQ ID NO: 176; a CDR L2 sequence comprising SEQ ID NO: 177, and a CDR L3 sequence comprising SEQ ID NO: 178; or u. a V_H comprising: a CDR-H1 comprising SEQ ID NOs: 24 or 45; a CDR-H2 comprising SEQ ID NOs: 66 or 87; and a CDR-H3 comprising SEQ ID NO: 108 and the V_L region comprises a CDR L1 comprising SEQ ID NO: 176; a CDR L2 sequence comprising SEQ ID NO: 177, and a CDR L3 sequence comprising SEQ ID NO: 178.

2. The antibody of claim 1, wherein:

a. the V_H region is SEQ ID NO: 130, and the V_L region is SEQ ID NO: 151;

b. the V_H region is SEQ ID NO: 131, and the V_L region is SEQ ID NO: 152;

c. the V_H region is SEQ ID NO: 132, and the V_L region is SEQ ID NO: 153;

d. the V_H region is SEQ ID NO: 133, and the V_L region is SEQ ID NO: 154;

e. the V_H region is SEQ ID NO: 134, and the V_L region is SEQ ID NO: 155;

f. the V_H region is SEQ ID NO: 135, and the V_L region is SEQ ID NO: 156;

g. the V_H region is SEQ ID NO: 136, and the V_L region is SEQ ID NO: 157;

h. the V_H region is SEQ ID NO: 137, and the V_L region is SEQ ID NO: 158;

i. the V_H region is SEQ ID NO: 138, and the V_L region is SEQ ID NO: 158;

j. the V_H region is SEQ ID NO: 139, and the V_L region is SEQ ID NO: 158;

l. the V_H region is SEQ ID NO: 140, and the V_L region is SEQ ID NO: 158;

m. the V_H region is SEQ ID NO: 141, and the V_L region is SEQ ID NO: 158;

n. the V_H region is SEQ ID NO: 142, and the V_L region is SEQ ID NO: 158;

o. the V_H region is SEQ ID NO: 143, and the V_L region is SEQ ID NO: 158;

P. the V_H region is SEQ ID NO: 144, and the V_L region is SEQ ID NO: 158;

q. the V_H region is SEQ ID NO: 145, and the V_L region is SEQ ID NO: 158;

r. the V_H region is SEQ ID NO: 146, and the V_L region is SEQ ID NO: 158;

s. the V_H region is SEQ ID NO: 147, and the V_L region is SEQ ID NO: 158;

t. the V_H region is SEQ ID NO: 148, and the V_L region is SEQ ID NO: 158;

u. the V_H region is SEQ ID NO: 149, and the V_L region is SEQ ID NO: 158; or v. the V_H region is SEQ ID NO: 150, and the V_L region is SEQ ID NO: 158.

3. The antibody of claim 1, wherein the antibody comprises at least one constant region domain.

4. The antibody of claim 3, wherein the constant region comprises a sequence selected from SEQ ID NOs: 159, 160, and 161.

5. The antibody of claim 1, wherein the antibody is a monoclonal antibody.

6. The antibody of claim 1, wherein the antibody is an IgA, an IgD, an IgE, an IgG, or an IgM.

7. The antibody of claim 1, wherein the antibody is humanized or human.

8. The antibody of claim 1, wherein the antibody is a glycosylated.

9. The antibody of claim 1, wherein the antibody is an antibody fragment.

10. The antibody of claim 9, wherein the antibody fragment is selected from an Fv fragment, a Fab fragment, a F(ab')_2 fragment, a Fab' fragment, an scFv (sFv) fragment, and an scFv-Fc fragment.

11. The antibody of claim 10, wherein the antibody is an scFv fragment.

12. The antibody of claim 11, wherein the scFv fragment comprises an scFv sequence selected from SEQ ID NO: 169, with or without the N-terminal M residue.

13. The antibody of claim 10, wherein the antibody is an scFv-Fc fragment.

14. The antibody of claim 13, wherein the scFv-Fc fragment comprises a sequence selected from SEQ ID NO: 169, with or without the N-terminal M residue.

15. The antibody of claim 1, wherein the antibody has a $k_a$ of about $6.71 \times 10^4$ $M^{-1} \times sec^{-1}$ to about $2.81 \times 10^5$ $M^{-1} \times sec^{-1}$ when associating with human Tim-3 at a temperature of 25° C.

16. The antibody of claim 1, wherein the antibody has a $k_d$ of about $2.05 \times 10^{-2}$ $sec^{-1}$ to about $4.25 \times 10^{-4}$ $sec^{-1}$ when dissociating from human Tim-3 at a temperature of 25° C.

17. The antibody of claim 1, wherein the antibody has a $K_D$ of about $9.1 \times 10^{-9}$ M to about $4.3 \times 10^{-10}$ M when bound to human Tim-3 at a temperature of 25° C.

18. The antibody of claim 1, wherein the antibody specifically binds cynomolgus Tim-3.

19. The antibody of claim 18, wherein the antibody has a $K_D$ of about 13.2 nM to about 0.5 nM when bound to cynomolgus Tim-3 at a temperature of 25° C.

20. The antibody of claim 19, wherein the ratio of $K_D$ for human Tim-3 to $K_D$ for cynomolgus Tim-3 is about 0.33 to about 18.2.

21. A kit comprising the antibody of claim 1, and instructions for use of the antibody.

22. A polynucleotide encoding the antibody of claim 1.

23. A vector comprising the polynucleotide of claim 22.

24. A recombinant host cell comprising the vector of claim 23.

25. A cell free composition comprising the vector of claim 23.

26. A pharmaceutical composition comprising the antibody of claim 1 and a pharmaceutically acceptable carrier.

27. An isolated antibody that specifically binds to human Tim-3, wherein the antibody comprises:
  a. three heavy chain CDRs and three light chain CDRs of the $V_H$ region SEQ ID NO: 130, and the $V_L$ region SEQ ID NO: 151;
  b. three heavy chain CDRs and three light chain CDRs of the $V_H$ region SEQ ID NO: 131, and the $V_L$ region SEQ ID NO: 152;
  c. three heavy chain CDRs and three light chain CDRs of the $V_H$ region SEQ ID NO: 132, and the $V_L$ region SEQ ID NO: 153;
  d. three heavy chain CDRs and three light chain CDRs of the $V_H$ region SEQ ID NO: 133, and the $V_L$ region SEQ ID NO: 154;
  e. three heavy chain CDRs and three light chain CDRs of the $V_H$ region SEQ ID NO: 134, and the $V_L$ region SEQ ID NO: 155;
  f. three heavy chain CDRs and three light chain CDRs of the $V_H$ region SEQ ID NO: 135, and the $V_L$ region SEQ ID NO: 156;
  g. three heavy chain CDRs and three light chain CDRs of the $V_H$ region SEQ ID NO: 136, and the $V_L$ region SEQ ID NO: 157;
  h. three heavy chain CDRs and three light chain CDRs of the $V_H$ region SEQ ID NO: 137, and the $V_L$ region SEQ ID NO: 158;
  i. three heavy chain CDRs and three light chain CDRs of the $V_H$ region SEQ ID NO: 138, and the $V_L$ region SEQ ID NO: 158;
  j. three heavy chain CDRs and three light chain CDRs of the $V_H$ region SEQ ID NO: 139, and the $V_L$ region SEQ ID NO: 158;
  k. three heavy chain CDRs and three light chain CDRs of the $V_H$ region SEQ ID NO: 140, and the $V_L$ region SEQ ID NO: 158;
  l. three heavy chain CDRs and three light chain CDRs of the $V_H$ region SEQ ID NO: 141, and the $V_L$ region SEQ ID NO: 158;
  m. three heavy chain CDRs and three light chain CDRs of the $V_H$ region SEQ ID NO: 142, and the $V_L$ region SEQ ID NO: 158;
  n. three heavy chain CDRs and three light chain CDRs of the $V_H$ region SEQ ID NO: 143, and the $V_L$ region SEQ ID NO: 158;
  o. three heavy chain CDRs and three light chain CDRs of the $V_H$ region SEQ ID NO: 144, and the $V_L$ region SEQ ID NO: 158;
  three heavy chain CDRs and three light chain CDRs of the $V_H$ region SEQ ID NO: 145, and the $V_L$ region SEQ ID NO: 158;
  q. three heavy chain CDRs and three light chain CDRs of the $V_H$ region SEQ ID NO: 146, and the $V_L$ region SEQ ID NO: 158;
  r. three heavy chain CDRs and three light chain CDRs of the $V_H$ region SEQ ID NO: 147, and the $V_L$ region SEQ ID NO: 158;
  s. three heavy chain CDRs and three light chain CDRs of the $V_H$ region SEQ ID NO: 148, and the $V_L$ region SEQ ID NO: 158;
  t. three heavy chain CDRs and three light chain CDRs of the $V_H$ region SEQ ID NO: 149, and the $V_L$ region SEQ ID NO: 158; or
  u. three heavy chain CDRs and three light chain CDRs of the $V_H$ region SEQ ID NO: 150, and the $V_L$ region SEQ ID NO: 158.

* * * * *

SEQUENCE LISTING

```
<160> NUMBER OF SEQ ID NOS: 178

<210> SEQ ID NO 1
<211> LENGTH: 301
<212> TYPE: PRT
<213> ORGANISM: Homo sapiens
<220> FEATURE:
<221> NAME/KEY: misc_feature
<222> LOCATION: (1)..(301)
<223> OTHER INFORMATION: Human Tim-3

<400> SEQUENCE: 1

Met Phe Ser His Leu Pro Phe Asp Cys Val Leu Leu Leu Leu Leu
 1               5                  10                  15

Leu Leu Thr Arg Ser Ser Glu Val Glu Tyr Arg Ala Glu Val Gly Gln
                20                  25                  30

Asn Ala Tyr Leu Pro Cys Phe Tyr Thr Pro Ala Ala Pro Gly Asn Leu
            35                  40                  45
```

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Ile Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Leu Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 2
<211> LENGTH: 301
<212> TYPE: PRT
<213> ORGANISM: Macaca fascicularis
<220> FEATURE:
<221> NAME/KEY: misc_feature
<222> LOCATION: (1)..(301)
<223> OTHER INFORMATION: Cynologus Tim-3

<400> SEQUENCE: 2

Met Phe Ser His Leu Pro Phe Asp Cys Val Leu Leu Leu Leu Leu Leu
1               5                   10                  15

Leu Leu Thr Arg Ser Ser Glu Val Glu Tyr Ile Ala Glu Val Gly Gln
            20                  25                  30

Asn Ala Tyr Leu Pro Cys Ser Tyr Thr Pro Ala Pro Pro Gly Asn Leu
        35                  40                  45

Val Pro Val Cys Trp Gly Lys Gly Ala Cys Pro Val Phe Asp Cys Ser
    50                  55                  60

Asn Val Val Leu Arg Thr Asp Asn Arg Asp Val Asn Asp Arg Thr Ser
65                  70                  75                  80

Gly Arg Tyr Trp Leu Lys Gly Asp Phe His Lys Gly Asp Val Ser Leu
                85                  90                  95

Thr Ile Glu Asn Val Thr Leu Ala Asp Ser Gly Val Tyr Cys Cys Arg

```
                        100                 105                 110
Ile Gln Ile Pro Gly Ile Met Asn Asp Glu Lys His Asn Val Lys Leu
            115                 120                 125

Val Val Ile Lys Pro Ala Lys Val Thr Pro Ala Pro Thr Leu Gln Arg
130                 135                 140

Asp Leu Thr Ser Ala Phe Pro Arg Met Leu Thr Thr Gly Glu His Gly
145                 150                 155                 160

Pro Ala Glu Thr Gln Thr Pro Gly Ser Leu Pro Asp Val Asn Leu Thr
                165                 170                 175

Val Ser Asn Phe Phe Cys Glu Leu Gln Ile Phe Thr Leu Thr Asn Glu
            180                 185                 190

Leu Arg Asp Ser Gly Ala Thr Ile Arg Thr Ala Ile Tyr Ile Ala Ala
        195                 200                 205

Gly Ile Ser Ala Gly Leu Ala Leu Ala Leu Ile Phe Gly Ala Leu Ile
    210                 215                 220

Phe Lys Trp Tyr Ser His Ser Lys Glu Lys Thr Gln Asn Leu Ser Ile
225                 230                 235                 240

Ser Leu Ala Asn Ile Pro Pro Ser Gly Leu Ala Asn Ala Val Ala Glu
                245                 250                 255

Gly Ile Arg Ser Glu Glu Asn Ile Tyr Thr Ile Glu Glu Asp Val Tyr
            260                 265                 270

Glu Val Glu Glu Pro Asn Glu Tyr Tyr Cys Tyr Val Ser Ser Gly Gln
        275                 280                 285

Gln Pro Ser Gln Pro Leu Gly Cys Arg Val Ala Met Pro
    290                 295                 300

<210> SEQ ID NO 3
<211> LENGTH: 281
<212> TYPE: PRT
<213> ORGANISM: Mus musculus
<220> FEATURE:
<221> NAME/KEY: misc_feature
<222> LOCATION: (1)..(281)
<223> OTHER INFORMATION: Mouse Tim-3

<400> SEQUENCE: 3

Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160
```

-continued

```
Glu Thr Gln Thr Leu Val Thr Leu His Asn Asn Gly Thr Lys Ile
            165                 170                 175

Ser Thr Trp Ala Asp Glu Ile Lys Asp Ser Gly Glu Thr Ile Arg Thr
        180                 185                 190

Ala Ile His Ile Gly Val Gly Val Ser Ala Gly Leu Thr Leu Ala Leu
            195                 200                 205

Ile Ile Gly Val Leu Ile Leu Lys Trp Tyr Ser Cys Lys Lys Lys
    210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 4

Gly Phe Ser Leu Thr Ser Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide: h22E11-VH1-69-VH

<400> SEQUENCE: 5

Gly Phe Ser Leu Thr Ser Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide: 22E11-VH

<400> SEQUENCE: 6

Gly Phe Ser Leu Thr Ser Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide: h22E11-VH4-30-4-VH

<400> SEQUENCE: 7

Gly Phe Ser Leu Thr Ser Tyr
1               5

<210> SEQ ID NO 8
```

```
<211> LENGTH: 7
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 8

Gly Phe Ser Leu Thr Ser Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide: h22E11-5-VH

<400> SEQUENCE: 9

Gly Phe Ser Leu Thr Ser Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide: 2D5-VH

<400> SEQUENCE: 10

Gly Tyr Pro Phe Ile Gly Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide: SRP1649-A01

<400> SEQUENCE: 11

Gly Phe Asn Ile Ser Arg Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide: SRP1649-F06

<400> SEQUENCE: 12

Gly Phe Asn Ile Gly Asn Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide: SRP1649-G08

<400> SEQUENCE: 13

Gly Phe Asn Ile Ser Asn Tyr
1               5

<210> SEQ ID NO 14
<211> LENGTH: 7
```

```
<212> TYPE: PRT
<213> ORGANISM: Artificial Sequence
<220> FEATURE:
<223> OTHER INFORMATION: Synthetic peptide: SRP1649-C05

<400> SEQUENCE: 14

Gly Phe Asn Ile Gly Lys His
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide: SRP1649-D11

<400> SEQUENCE: 15

Gly Phe Asn Ile Ser Gly Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide: SRP1497-A02

<400> SEQUENCE: 16

Gly Phe Asn Ile Ser Asn Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide: SRP1497-A01

<400> SEQUENCE: 17

Gly Phe Asn Ile Ser Asn Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide: SRP1497-A05

<400> SEQUENCE: 18

Gly Phe Asn Ile Ser Asn Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide: SRP1649-B06

<400> SEQUENCE: 19

Gly Phe Asn Ile Ser Asn His
1               5

<210> SEQ ID NO 20
<211> LENGTH: 7
<212> TYPE: PRT
```

-continued

```
<213> ORGANISM: Artificial Sequence
<220> FEATURE:
<223> OTHER INFORMATION: Synthetic peptide: SRP1649-D06

<400> SEQUENCE: 20

Gly Phe Asn Ile Arg Asn His
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide: SRP1649-H02

<400> SEQUENCE: 21

Gly Phe Asn Ile Arg Ser Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide: SRP1649-B09

<400> SEQUENCE: 22

Gly Phe Asn Ile Arg Asn Asn
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide: SRP1649-E10

<400> SEQUENCE: 23

Gly Phe Asn Ile Ser Asn Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide: SRP1649-E08

<400> SEQUENCE: 24

Gly Phe Ser Ile Ser Asn Tyr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 25

Ser Tyr Gly Val His
1               5

<210> SEQ ID NO 26
<211> LENGTH: 5
<212> TYPE: PRT
<213> ORGANISM: Artificial Sequence
```

```
<220> FEATURE:
<223> OTHER INFORMATION: Synthetic peptide: h22E11-VH1-69-VH

<400> SEQUENCE: 26

Ser Tyr Gly Val His
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide: 22E11-VH

<400> SEQUENCE: 27

Ser Tyr Gly Val His
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide: h22E11-VH4-30-4-VH

<400> SEQUENCE: 28

Ser Tyr Gly Val His
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 29

Ser Tyr Gly Val His
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide: h22E11-5-VH

<400> SEQUENCE: 30

Ser Tyr Gly Val His
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide: 2D5-VH

<400> SEQUENCE: 31

Gly Tyr Thr Met Asn
1               5

<210> SEQ ID NO 32
<211> LENGTH: 5
<212> TYPE: PRT
<213> ORGANISM: Artificial Sequence
<220> FEATURE:
```

<223> OTHER INFORMATION: Synthetic peptide: SRP1649-A01

<400> SEQUENCE: 32

Arg Tyr Tyr Ile His
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide: SRP1649-F06

<400> SEQUENCE: 33

Asn Tyr Ala Ile His
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide: SRP1649-G08

<400> SEQUENCE: 34

Asn Tyr Val Ile His
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide: SRP1649-C05

<400> SEQUENCE: 35

Lys His Val Ile His
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide: SRP1649-D11

<400> SEQUENCE: 36

Gly Tyr Val Ile His
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide: SRP1497-A02

<400> SEQUENCE: 37

Asn Tyr Ala Ile His
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide: SRP1497-A01

```
<400> SEQUENCE: 38

Asn Tyr Ala Ile His
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide: SRP1497-A05

<400> SEQUENCE: 39

Asn Tyr Ala Ile His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide: SRP1649-B06

<400> SEQUENCE: 40

Asn His Ala Ile His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide: SRP1649-D06

<400> SEQUENCE: 41

Asn His Ala Ile His
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide: SRP1649-H02

<400> SEQUENCE: 42

Ser Tyr Ala Ile His
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide: SRP1649-B09

<400> SEQUENCE: 43

Asn Asn Ala Ile His
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide: SRP1649-E10
```

```
<400> SEQUENCE: 44

Asn Asn Val Ile His
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide: SRP1649-E08

<400> SEQUENCE: 45

Asn Tyr Val Ile His
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 46

Trp Ser Asp Gly Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide: h22E11-VH1-69-VH

<400> SEQUENCE: 47

Trp Ser Asp Gly Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide: 22E11-VH

<400> SEQUENCE: 48

Trp Ser Asp Gly Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide: h22E11-VH4-30-4-VH

<400> SEQUENCE: 49

Trp Ser Asp Gly Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 50
```

```
Trp Ser Asp Gly Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide: h22E11-5-VH

<400> SEQUENCE: 51

Trp Ser Asp Gly Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide: 2D5-VH

<400> SEQUENCE: 52

Asn Pro Tyr Asn Gly Ile
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide: SRP1649-A01

<400> SEQUENCE: 53

Thr Pro Val Arg Gly Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide: SRP1649-F06

<400> SEQUENCE: 54

Thr Pro Gly Gln Gly Tyr
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic peptide: SRP1649-G08

<400> SEQUENCE: 55

Thr Pro Asp Gly Gly Ile
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide: SRP1649-C05

<400> SEQUENCE: 56
```

```
Val Pro Asn Gly Gly Tyr
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide: SRP1649-D11

<400> SEQUENCE: 57

Ile Pro Thr Ala Gly Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide: SRP1497-A02

<400> SEQUENCE: 58

Thr Pro Asp Gly Gly Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide: SRP1497-A01

<400> SEQUENCE: 59

Thr Pro Asp Gly Gly Tyr
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide: SRP1497-A05

<400> SEQUENCE: 60

Thr Pro Asp Gly Gly Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide: SRP1649-B06

<400> SEQUENCE: 61

Ser Pro Ala Val Gly Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide: SRP1649-D06

<400> SEQUENCE: 62

Ala Pro Ala Gly Gly Tyr
```

```
<210> SEQ ID NO 63
<211> LENGTH: 6
<212> TYPE: PRT
<213> ORGANISM: Artificial Sequence
<220> FEATURE:
<223> OTHER INFORMATION: Synthetic peptide: SRP1649-H02

<400> SEQUENCE: 63

Thr Pro Ala Gly Gly Asp
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide: SRP1649-B09

<400> SEQUENCE: 64

Thr Pro Ala Gly Gly Tyr
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic peptide: SRP1649-E10

<400> SEQUENCE: 65

Met Pro Gly Gly Gly Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide: SRP1649-E08

<400> SEQUENCE: 66

Ser Pro Asp Gly Gly Phe
1               5

<210> SEQ ID NO 67
<211> LENGTH: 16
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 67

Val Ile Trp Ser Asp Gly Ser Thr Thr Tyr Asn Pro Ser Phe Gln Gly
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic peptide: h22E11-VH1-69-VH

<400> SEQUENCE: 68

Val Ile Trp Ser Asp Gly Ser Thr Thr Tyr Asn Gln Lys Phe Gln Gly
1               5                   10                  15
```

```
<210> SEQ ID NO 69
<211> LENGTH: 16
<212> TYPE: PRT
<213> ORGANISM: Artificial Sequence
<220> FEATURE:
<223> OTHER INFORMATION: Synthetic peptide: 22E11-VH

<400> SEQUENCE: 69

Val Ile Trp Ser Asp Gly Ser Thr Thr Tyr Asn Ser Ala Leu Lys Ser
 1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: Synthetic peptide: h22E11-VH4-30-4-VH

<400> SEQUENCE: 70

Val Ile Trp Ser Asp Gly Ser Thr Thr Tyr Asn Pro Ser Leu Lys Ser
 1               5                  10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 71

Val Ile Trp Ser Asp Gly Ser Thr Thr Tyr Asn Asp Ser Val Lys Gly
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic peptide: h22E11-5-VH

<400> SEQUENCE: 72

Val Ile Trp Ser Asp Gly Ser Thr Thr Tyr Asn Ser Ala Leu Lys Ser
 1               5                  10                  15

<210> SEQ ID NO 73
<211> LENGTH: 17
<212> TYPE: PRT
<213> ORGANISM: Artificial Sequence
<220> FEATURE:
<223> OTHER INFORMATION: Synthetic peptide: 2D5-VH

<400> SEQUENCE: 73

Leu Ile Asn Pro Tyr Asn Gly Ile Thr Thr Tyr Asn Gln Lys Phe Lys
 1               5                  10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic peptide: SRP1649-A01

<400> SEQUENCE: 74

Gly Ile Thr Pro Val Arg Gly Tyr Thr Glu Tyr Ala Asp Ser Val Lys
```

```
1               5                   10                  15
Asp

<210> SEQ ID NO 75
<211> LENGTH: 17
<212> TYPE: PRT
<213> ORGANISM: Artificial Sequence
<220> FEATURE:
<223> OTHER INFORMATION: Synthetic peptide: SRP1649-F06

<400> SEQUENCE: 75

Asp Ile Thr Pro Gly Gln Gly Tyr Thr Glu Tyr Ala Asp Ser Val Lys
1               5                   10                  15
Asp

<210> SEQ ID NO 76
<211> LENGTH: 17
<212> TYPE: PRT
<213> ORGANISM: Artificial Sequence
<220> FEATURE:
<223> OTHER INFORMATION: Synthetic peptide: SRP1649-G08

<400> SEQUENCE: 76

Ala Ile Thr Pro Asp Gly Gly Ile Thr Glu Tyr Ala Asp Ser Val Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic peptide: SRP1649-C05

<400> SEQUENCE: 77

Asp Ile Val Pro Asn Gly Gly Tyr Thr Glu Tyr Ala Asp Ser Val Lys
1               5                   10                  15
Asp

<210> SEQ ID NO 78
<211> LENGTH: 17
<212> TYPE: PRT
<213> ORGANISM: Artificial Sequence
<220> FEATURE:
<223> OTHER INFORMATION: Synthetic peptide: SRP1649-D11

<400> SEQUENCE: 78

Asp Ile Ile Pro Thr Ala Gly Tyr Thr Glu Tyr Ala Asp Ser Val Lys
1               5                   10                  15
Gly

<210> SEQ ID NO 79
<211> LENGTH: 17
<212> TYPE: PRT
<213> ORGANISM: Artificial Sequence
<220> FEATURE:
<223> OTHER INFORMATION: Synthetic peptide: SRP1497-A02

<400> SEQUENCE: 79

Asp Ile Thr Pro Asp Gly Gly Tyr Thr Asp Tyr Ala Asp Ser Val Lys
1               5                   10                  15
Gly
```

<210> SEQ ID NO 80
<211> LENGTH: 17
<212> TYPE: PRT
<213> ORGANISM: Artificial Sequence
<220> FEATURE:
<223> OTHER INFORMATION: Synthetic peptide: SRP1497-A01

<400> SEQUENCE: 80

Asp Ile Thr Pro Asp Gly Gly Tyr Thr Asp Tyr Ala Asp Ser Val Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic peptide: SRP1497-A05

<400> SEQUENCE: 81

Asp Ile Thr Pro Asp Gly Gly Tyr Thr Asp Tyr Ala Asp Ser Val Lys
1               5                   10                  15

Asp

<210> SEQ ID NO 82
<211> LENGTH: 17
<212> TYPE: PRT
<213> ORGANISM: Artificial Sequence
<220> FEATURE:
<223> OTHER INFORMATION: Synthetic peptide: SRP1649-B06

<400> SEQUENCE: 82

Asp Ile Ser Pro Ala Val Gly Tyr Thr Asp Tyr Ala Asp Ser Val Lys
1               5                   10                  15

Asp

<210> SEQ ID NO 83
<211> LENGTH: 17
<212> TYPE: PRT
<213> ORGANISM: Artificial Sequence
<220> FEATURE:
<223> OTHER INFORMATION: Synthetic peptide: SRP1649-D06

<400> SEQUENCE: 83

Asp Ile Ala Pro Ala Gly Gly Tyr Thr Asp Tyr Ala Asp Ser Val Lys
1               5                   10                  15

Asp

<210> SEQ ID NO 84
<211> LENGTH: 17
<212> TYPE: PRT
<213> ORGANISM: Artificial Sequence
<220> FEATURE:
<223> OTHER INFORMATION: Synthetic peptide: SRP1649-H02

<400> SEQUENCE: 84

Asp Ile Thr Pro Ala Gly Gly Asp Thr Glu Tyr Ala Asp Ser Val Lys
1               5                   10                  15

Gly

<210> SEQ ID NO 85
<211> LENGTH: 17
<212> TYPE: PRT

```
<213> ORGANISM: Artificial Sequence
<220> FEATURE:
<223> OTHER INFORMATION: Synthetic peptide: SRP1649-B09

<400> SEQUENCE: 85

Asp Ile Thr Pro Ala Gly Gly Tyr Thr Gly Tyr Ala Asp Ser Val Lys
1               5                   10                  15

Asp

<210> SEQ ID NO 86
<211> LENGTH: 17
<212> TYPE: PRT
<213> ORGANISM: Artificial Sequence
<220> FEATURE:
<223> OTHER INFORMATION: Synthetic peptide: SRP1649-E10

<400> SEQUENCE: 86

Asp Ile Met Pro Gly Gly Gly Ser Thr Asp Tyr Ala Asp Ser Val Lys
1               5                   10                  15

Asp

<210> SEQ ID NO 87
<211> LENGTH: 17
<212> TYPE: PRT
<213> ORGANISM: Artificial Sequence
<220> FEATURE:
<223> OTHER INFORMATION: Synthetic peptide: SRP1649-E08

<400> SEQUENCE: 87

Asp Ile Ser Pro Asp Gly Gly Phe Thr Asp Tyr Ala Asp Ser Val Lys
1               5                   10                  15

Asp

<210> SEQ ID NO 88
<211> LENGTH: 12
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 88

Gln Gly Gly Tyr Arg Tyr Asp Asp Ala Met Asp Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic peptide: h22E11-VH1-69-VH

<400> SEQUENCE: 89

Gln Gly Gly Tyr Arg Tyr Asp Asp Ala Met Asp Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic peptide: 22E11-VH

<400> SEQUENCE: 90

Gln Gly Gly Tyr Arg Tyr Asp Asp Ala Met Asp Tyr
1               5                   10
```

<210> SEQ ID NO 91
<211> LENGTH: 12
<212> TYPE: PRT
<213> ORGANISM: Artificial Sequence
<220> FEATURE:
<223> OTHER INFORMATION: Synthetic peptide: h22E11-VH4-30-4-VH

<400> SEQUENCE: 91

Gln Gly Gly Tyr Arg Tyr Asp Asp Ala Met Asp Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 92

Gln Gly Gly Tyr Arg Tyr Asp Asp Ala Met Asp Tyr
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic peptide: h22E11-5-VH

<400> SEQUENCE: 93

Gln Gly Gly Tyr Arg Tyr Asp Asp Ala Met Asp Tyr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic peptide: 2D5-VH

<400> SEQUENCE: 94

Ser Phe Phe Tyr Gly Ser Ser Asn Asp Trp Leu Val Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic peptide: SRP1649-A01

<400> SEQUENCE: 95

Gly Tyr Val Tyr Arg Met Trp Asp Ser Tyr Asp Tyr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic peptide: SRP1649-F06

<400> SEQUENCE: 96

Gly Tyr Val Tyr Arg Met Trp Asp Ser Tyr Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic peptide: SRP1649-G08

<400> SEQUENCE: 97

Gly Tyr Val Tyr Arg Met Trp Asp Ser Tyr Asp Tyr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic peptide: SRP1649-C05

<400> SEQUENCE: 98

Gly Tyr Val Tyr Arg Met Trp Asp Ser Phe Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic peptide: SRP1649-D11

<400> SEQUENCE: 99

Gly Tyr Val Tyr Arg Met Trp Asp Ser Phe Asp Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic peptide: SRP1497-A02

<400> SEQUENCE: 100

Gly Tyr Val Tyr Arg Met Trp Asp Ser Phe Asp Tyr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic peptide: SRP1497-A01

<400> SEQUENCE: 101

Gly Tyr Val Tyr Arg Met Trp Asp Ser Phe Asp Tyr
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic peptide: SRP1497-A05

<400> SEQUENCE: 102

Gly Tyr Val Tyr Arg Met Trp Asp Ser Phe Asp Tyr
1               5                   10

```
<210> SEQ ID NO 103
<211> LENGTH: 12
<212> TYPE: PRT
<213> ORGANISM: Artificial Sequence
<220> FEATURE:
<223> OTHER INFORMATION: Synthetic peptide: SRP1649-B06

<400> SEQUENCE: 103

Gly Tyr Val Tyr Arg Met Trp Asp Ser Phe Asp His
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic peptide: SRP1649-D06

<400> SEQUENCE: 104

Gly Tyr Val Tyr Arg Met Trp Asp Ser Tyr Asp Tyr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic peptide: SRP1649-H02

<400> SEQUENCE: 105

Gly Tyr Ile Tyr Arg Met Trp Asp Ser Tyr Asp Tyr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic peptide: SRP1649-B09

<400> SEQUENCE: 106

Gly Tyr Ile Tyr Arg Met Trp Asp Ser Leu Asp Tyr
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic peptide: SRP1649-E10

<400> SEQUENCE: 107

Gly Tyr Val Tyr Arg Met Trp Asp Ser Tyr Asp Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic peptide: SRP1649-E08

<400> SEQUENCE: 108

Gly His Val Tyr Arg Leu Trp Asp Ser Phe Asp Tyr
1               5                   10

<210> SEQ ID NO 109
```

```
<211> LENGTH: 15
<212> TYPE: PRT
<213> ORGANISM: Artificial Sequence
<220> FEATURE:
<223> OTHER INFORMATION: Synthetic peptide: h22E11-Vk3-11-VL

<400> SEQUENCE: 109

Lys Ala Ser Gln Ser Val Asp Tyr Asp Gly Asn Ser Tyr Val Asn
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide: h22E11-5-VL

<400> SEQUENCE: 110

Lys Ala Ser Gln Ser Val Asp Tyr Asp Gly Asn Ser Tyr Val Ala
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic peptide: h22E11-Vk1-39-VL

<400> SEQUENCE: 111

Lys Ala Ser Gln Ser Val Asp Tyr Asp Gly Asn Ser Tyr Val Asn
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide: h22E11-Vk4-1-VL

<400> SEQUENCE: 112

Lys Ala Ser Gln Ser Val Asp Tyr Asp Gly Asn Ser Tyr Val Asn
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic peptide: 22E11-VL

<400> SEQUENCE: 113

Lys Ala Ser Gln Ser Val Asp Tyr Asp Gly Asn Ser Tyr Val Asn
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide: h22E11-Vk2-28-VL

<400> SEQUENCE: 114

Lys Ala Ser Gln Ser Val Asp Tyr Asp Gly Asn Ser Tyr Val Asn
1               5                   10                  15

<210> SEQ ID NO 115
<211> LENGTH: 16
```

```
<212> TYPE: PRT
<213> ORGANISM: Artificial Sequence
<220> FEATURE:
<223> OTHER INFORMATION: Synthetic peptide: 2D5-VL

<400> SEQUENCE: 115

Arg Ser Ser Gln Ser Ile Val His Thr Asn Gly Asn Thr Tyr Leu Glu
1               5                   10                  15

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide: h22E11-Vk3-11-VL

<400> SEQUENCE: 116

Ala Ala Ser Asn Leu Glu Ser
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide: h22E11-5-VL

<400> SEQUENCE: 117

Ala Ala Ser Asn Leu Glu Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide: h22E11-Vk1-39-VL

<400> SEQUENCE: 118

Ala Ala Ser Asn Leu Glu Ser
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide: h22E11-Vk4-1-VL

<400> SEQUENCE: 119

Ala Ala Ser Asn Leu Glu Ser
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide: 22E11-VL

<400> SEQUENCE: 120

Ala Ala Ser Asn Leu Glu Ser
1               5

<210> SEQ ID NO 121
<211> LENGTH: 7
<212> TYPE: PRT
```

<213> ORGANISM: Artificial Sequence
<220> FEATURE:
<223> OTHER INFORMATION: Synthetic peptide: h22E11-Vk2-28-VL

<400> SEQUENCE: 121

Ala Ala Ser Asn Leu Glu Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide: 2D5-VL

<400> SEQUENCE: 122

Lys Val Ser Asn Arg Phe Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic peptide: h22E11-Vk3-11-VL

<400> SEQUENCE: 123

Gln Gln Ser Asn Glu Asp Pro Tyr Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide: h22E11-5-VL

<400> SEQUENCE: 124

Gln Gln Ser Asn Glu Asp Pro Tyr Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide: h22E11-Vk1-39-VL

<400> SEQUENCE: 125

Gln Gln Ser Asn Glu Asp Pro Tyr Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide: h22E11-Vk4-1-VL

<400> SEQUENCE: 126

Gln Gln Ser Asn Glu Asp Pro Tyr Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide: 22E11-VL

<400> SEQUENCE: 127

Gln Gln Ser Asn Glu Asp Pro Tyr Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide: h22E11-Vk2-28-VL

<400> SEQUENCE: 128

Gln Gln Ser Asn Glu Asp Pro Tyr Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide: 2D5-VL

<400> SEQUENCE: 129

Phe Gln Gly Ser His Val Pro Trp Thr
1               5

<210> SEQ ID NO 130
<211> LENGTH: 122
<212> TYPE: PRT
<213> ORGANISM: Artificial Sequence
<220> FEATURE:
<223> OTHER INFORMATION: Synthetic peptide: 2D5-VH

<400> SEQUENCE: 130

Glu Val Gln Leu Gln Gln Ser Gly Pro Glu Leu Val Lys Pro Gly Thr
1               5                   10                  15

Ser Met Lys Ile Ser Cys Arg Ala Ser Gly Tyr Pro Phe Ile Gly Tyr
            20                  25                  30

Thr Met Asn Trp Val Lys Gln Ser His Gly Gly Asn Leu Glu Trp Ile
        35                  40                  45

Gly Leu Ile Asn Pro Tyr Asn Gly Ile Thr Thr Tyr Asn Gln Lys Phe
    50                  55                  60

Lys Gly Arg Ala Thr Leu Ser Val Asp Thr Ser Ser Thr Ile Ala Tyr
65                  70                  75                  80

Met Glu Leu Leu Ser Leu Thr Ser Asp Asp Ser Ala Glu Tyr Tyr Cys
                85                  90                  95

Ala Arg Ser Phe Phe Tyr Gly Ser Ser Asn Asp Trp Leu Val Tyr Trp
            100                 105                 110

Gly Gln Gly Thr Leu Val Thr Val Ser Ala
        115                 120

<210> SEQ ID NO 131
<211> LENGTH: 120
<212> TYPE: PRT
<213> ORGANISM: Artificial Sequence
<220> FEATURE:
<223> OTHER INFORMATION: Synthetic peptide: 22E11-VH

<400> SEQUENCE: 131

Gln Val Gln Leu Lys Glu Ser Gly Pro Asp Leu Val Ala Pro Ser Gln

```
                1               5                  10                  15
            Ser Leu Ser Ile Thr Cys Thr Val Ser Gly Phe Ser Leu Thr Ser Tyr
                        20                  25                  30

Gly Val His Trp Val Arg Gln Pro Gly Lys Gly Leu Glu Trp Leu
                        35                  40                  45

Val Val Ile Trp Ser Asp Gly Ser Thr Thr Tyr Asn Ser Ala Leu Lys
                        50                  55                  60

Ser Arg Leu Thr Ile Ser Lys Asp Asn Ser Lys Ser Gln Val Phe Leu
            65                  70                  75                  80

Lys Met Asn Ser Leu Gln Thr Asp Asp Thr Ala Met Tyr Tyr Cys Ala
                        85                  90                  95

Arg Gln Gly Gly Tyr Arg Tyr Asp Asp Ala Met Asp Tyr Trp Gly Gln
                        100                 105                 110

Gly Thr Ser Val Ala Val Ser Ser
                        115                 120

<210> SEQ ID NO 132
<211> LENGTH: 120
<212> TYPE: PRT
<213> ORGANISM: Artificial Sequence
<220> FEATURE:
<223> OTHER INFORMATION: Synthetic peptide: h22E11-VH5-51-VH

<400> SEQUENCE: 132

Glu Val Gln Leu Val Gln Ser Gly Ala Glu Val Lys Lys Pro Gly Glu
            1               5                   10                  15

Ser Leu Lys Ile Ser Cys Lys Val Ser Gly Phe Ser Leu Thr Ser Tyr
                        20                  25                  30

Gly Val His Trp Val Arg Gln Met Pro Gly Lys Gly Leu Glu Trp Leu
                        35                  40                  45

Val Val Ile Trp Ser Asp Gly Ser Thr Thr Tyr Asn Pro Ser Phe Gln
                        50                  55                  60

Gly Gln Val Thr Ile Ser Lys Asp Lys Ser Ile Ser Thr Val Tyr Leu
            65                  70                  75                  80

Gln Trp Ser Ser Leu Lys Ala Ser Asp Thr Ala Met Tyr Tyr Cys Ala
                        85                  90                  95

Arg Gln Gly Gly Tyr Arg Tyr Asp Asp Ala Met Asp Tyr Trp Gly Gln
                        100                 105                 110

Gly Thr Leu Val Thr Val Ser Ser
                        115                 120

<210> SEQ ID NO 133
<211> LENGTH: 120
<212> TYPE: PRT
<213> ORGANISM: Artificial Sequence
<220> FEATURE:
<223> OTHER INFORMATION: Synthetic peptide: h22E11-VH4-30-4-H

<400> SEQUENCE: 133

Gln Val Gln Leu Gln Glu Ser Gly Pro Gly Leu Val Lys Pro Ser Gln
            1               5                   10                  15

Thr Leu Ser Leu Thr Cys Thr Val Ser Gly Phe Ser Leu Thr Ser Tyr
                        20                  25                  30

Gly Val His Trp Ile Arg Gln Pro Pro Gly Lys Gly Leu Glu Trp Leu
                        35                  40                  45

Val Val Ile Trp Ser Asp Gly Ser Thr Thr Tyr Asn Pro Ser Leu Lys
                        50                  55                  60
```

```
Ser Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Gln Gly Gly Tyr Arg Tyr Asp Asp Ala Met Asp Tyr Trp Gly Gln
            100                 105                 110

Gly Thr Leu Val Thr Val Ser Ser
        115                 120

<210> SEQ ID NO 134
<211> LENGTH: 120
<212> TYPE: PRT
<213> ORGANISM: Artificial Sequence
<220> FEATURE:
<223> OTHER INFORMATION: Synthetic peptide: h22E11-VH3-23-VH

<400> SEQUENCE: 134

Glu Val Gln Leu Leu Glu Ser Gly Gly Gly Leu Val Gln Pro Gly Gly
 1               5                  10                  15

Ser Leu Arg Leu Ser Cys Ala Val Ser Gly Phe Ser Leu Thr Ser Tyr
                20                  25                  30

Gly Val His Trp Val Arg Gln Ala Pro Gly Lys Gly Leu Glu Trp Leu
            35                  40                  45

Val Val Ile Trp Ser Asp Gly Ser Thr Thr Tyr Asn Asp Ser Val Lys
        50                  55                  60

Gly Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Gln Gly Gly Tyr Arg Tyr Asp Asp Ala Met Asp Tyr Trp Gly Gln
            100                 105                 110

Gly Thr Leu Val Thr Val Ser Ser
        115                 120

<210> SEQ ID NO 135
<211> LENGTH: 120
<212> TYPE: PRT
<213> ORGANISM: Artificial Sequence
<220> FEATURE:
<223> OTHER INFORMATION: Synthetic peptide: h22E11-VH1-69-VH

<400> SEQUENCE: 135

Gln Val Gln Leu Val Gln Ser Gly Ala Glu Val Lys Lys Pro Gly Ser
 1               5                  10                  15

Ser Val Lys Val Ser Cys Lys Val Ser Gly Phe Ser Leu Thr Ser Tyr
                20                  25                  30

Gly Val His Trp Val Arg Gln Ala Pro Gly Gln Gly Leu Glu Trp Leu
            35                  40                  45

Val Val Ile Trp Ser Asp Gly Ser Thr Thr Tyr Asn Gln Lys Phe Gln
        50                  55                  60

Gly Arg Val Thr Ile Thr Lys Asp Glu Ser Thr Ser Thr Val Tyr Met
 65                  70                  75                  80

Glu Leu Ser Ser Leu Arg Ser Glu Asp Thr Ala Val Tyr Tyr Cys Ala
                 85                  90                  95

Arg Gln Gly Gly Tyr Arg Tyr Asp Asp Ala Met Asp Tyr Trp Gly Gln
            100                 105                 110

Gly Thr Leu Val Thr Val Ser Ser
        115                 120
```

<210> SEQ ID NO 136
<211> LENGTH: 120
<212> TYPE: PRT
<213> ORGANISM: Artificial Sequence
<220> FEATURE:
<223> OTHER INFORMATION: Synthetic peptide: h22E11-5-VH

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Phe Thr Ile Ser Lys Asp Asn Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Arg Gln Gly Gly Tyr Arg Tyr Asp Asp Ala Met Asp Tyr Trp Gly Gln
            100                 105                 110

Gly Thr Leu Val Thr Val Ser Ser
        115                 120

<210> SEQ ID NO 137
<211> LENGTH: 121
<212> TYPE: PRT
<213> ORGANISM: Artificial Sequence
<220> FEATURE:
<223> OTHER INFORMATION: Synthetic peptide: SRP1649-A01

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Arg Tyr
            20                  25                  30

Tyr Ile His Trp Val Arg Gln Ala Pro Gly Lys Gly Leu Glu Trp Val
        35                  40                  45

Ala Gly Ile Thr Pro Val Arg Gly Tyr Thr Glu Tyr Ala Asp Ser Val
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Tyr Asp Tyr Trp Gly
            100                 105                 110

Gln Gly Thr Leu Val Thr Val Ser Ser
        115                 120

<210> SEQ ID NO 138
<211> LENGTH: 121
<212> TYPE: PRT
<213> ORGANISM: Artificial Sequence
<220> FEATURE:
<223> OTHER INFORMATION: Synthetic peptide: SRP1649-B06

<400> SEQUENCE: 138

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn His
            20                  25                  30

Ala Ile His Trp Val Arg Gln Ala Pro Gly Lys Gly Leu Glu Trp Val
        35                  40                  45

Ala Asp Ile Ser Pro Ala Val Gly Tyr Thr Asp Tyr Ala Asp Ser Val
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Phe Asp His Trp Gly
            100                 105                 110

Gln Gly Thr Leu Val Thr Val Ser Ser
        115                 120
```

<210> SEQ ID NO 139
<211> LENGTH: 121
<212> TYPE: PRT
<213> ORGANISM: Artificial Sequence
<220> FEATURE:
<223> OTHER INFORMATION: Synthetic peptide: SRP1649-C05

<400> SEQUENCE: 139

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Lys His
            20                  25                  30

Val Ile His Trp Val Arg Gln Ala Pro Gly Lys Gly Leu Glu Trp Val
        35                  40                  45

Ala Asp Ile Val Pro Asn Gly Gly Tyr Thr Glu Tyr Ala Asp Ser Val
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Phe Asp Tyr Trp Gly
            100                 105                 110

Gln Gly Thr Leu Val Thr Val Ser Ser
        115                 120
```

<210> SEQ ID NO 140
<211> LENGTH: 121
<212> TYPE: PRT
<213> ORGANISM: Artificial Sequence
<220> FEATURE:
<223> OTHER INFORMATION: Synthetic peptide: SRP1649-D06

<400> SEQUENCE: 140

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asn His
            20                  25                  30

Ala Ile His Trp Val Arg Gln Ala Pro Gly Lys Gly Leu Glu Trp Val
        35                  40                  45

Ala Asp Ile Ala Pro Ala Gly Gly Tyr Thr Asp Tyr Ala Asp Ser Val
50                  55                  60
```

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Val Tyr Arg Met Trp Asp Ser Tyr Asp Tyr Trp Gly
            100                 105                 110

Gln Gly Thr Leu Val Thr Val Ser Ser
        115                 120

<210> SEQ ID NO 141
<211> LENGTH: 121
<212> TYPE: PRT
<213> ORGANISM: Artificial Sequence
<220> FEATURE:
<223> OTHER INFORMATION: Synthetic peptide: SRP1649-D11

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Gly Tyr
            20                  25                  30

Val Ile His Trp Val Arg Gln Ala Pro Gly Lys Gly Leu Glu Trp Val
        35                  40                  45

Ala Asp Ile Ile Pro Thr Ala Gly Tyr Thr Glu Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Val Tyr Arg Met Trp Asp Ser Phe Asp Tyr Trp Gly
            100                 105                 110

Gln Gly Thr Leu Val Thr Val Ser Ser
        115                 120

<210> SEQ ID NO 142
<211> LENGTH: 121
<212> TYPE: PRT
<213> ORGANISM: Artificial Sequence
<220> FEATURE:
<223> OTHER INFORMATION: Synthetic peptide: SRP1649-E08

<400> SEQUENCE: 142

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Ser Ile Ser Asn Tyr
            20                  25                  30

Val Ile His Trp Val Arg Gln Ala Pro Gly Lys Gly Leu Glu Trp Val
        35                  40                  45

Ala Asp Ile Ser Pro Asp Gly Gly Phe Thr Asp Tyr Ala Asp Ser Val
    50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly His Val Tyr Arg Leu Trp Asp Ser Phe Asp Tyr Trp Gly
            100                 105                 110

Arg Gly Thr Leu Val Thr Val Ser Ser

-continued

```
            115                 120

<210> SEQ ID NO 143
<211> LENGTH: 121
<212> TYPE: PRT
<213> ORGANISM: Artificial Sequence
<220> FEATURE:
<223> OTHER INFORMATION: Synthetic peptide: SRP1649-E10

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Asn
            20                  25                  30

Val Ile His Trp Val Arg Gln Ala Pro Gly Lys Gly Leu Glu Trp Val
        35                  40                  45

Gly Asp Ile Met Pro Gly Gly Ser Thr Asp Tyr Ala Asp Ser Val
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Tyr Asp Tyr Trp Gly
            100                 105                 110

Gln Gly Thr Leu Val Thr Val Ser Ser
        115                 120

<210> SEQ ID NO 144
<211> LENGTH: 121
<212> TYPE: PRT
<213> ORGANISM: Artificial Sequence
<220> FEATURE:
<223> OTHER INFORMATION: Synthetic peptide: SRP1649-F06

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Asn Tyr
            20                  25                  30

Ala Ile His Trp Val Arg Gln Ala Pro Gly Lys Gly Leu Glu Trp Val
        35                  40                  45

Ala Asp Ile Thr Pro Gly Gln Gly Tyr Thr Glu Tyr Ala Asp Ser Val
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Tyr Asp Tyr Trp Gly
            100                 105                 110

Gln Gly Thr Leu Val Thr Val Ser Ser
        115                 120

<210> SEQ ID NO 145
<211> LENGTH: 121
<212> TYPE: PRT
<213> ORGANISM: Artificial Sequence
<220> FEATURE:
<223> OTHER INFORMATION: Synthetic peptide: SRP1649-G08

<400> SEQUENCE: 145
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
                20                  25                  30

Val Ile His Trp Val Arg Gln Ala Pro Gly Lys Gly Leu Glu Trp Val
            35                  40                  45

Ala Ala Ile Thr Pro Asp Gly Gly Ile Thr Glu Tyr Ala Asp Ser Val
        50                  55                  60

Lys Gly Arg Phe Ala Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Tyr Asp Tyr Trp Gly
                100                 105                 110

Gln Gly Thr Leu Val Thr Val Ser Ser
            115                 120

<210> SEQ ID NO 146
<211> LENGTH: 121
<212> TYPE: PRT
<213> ORGANISM: Artificial Sequence
<220> FEATURE:
<223> OTHER INFORMATION: Synthetic peptide: SRP1649-H02

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ser Tyr
                20                  25                  30

Ala Ile His Trp Val Arg Gln Ala Pro Gly Lys Gly Leu Glu Trp Val
            35                  40                  45

Ala Asp Ile Thr Pro Ala Gly Gly Asp Thr Glu Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Ile Tyr Arg Met Trp Asp Ser Tyr Asp Tyr Trp Gly
                100                 105                 110

Gln Gly Thr Leu Val Thr Val Ser Ser
            115                 120

<210> SEQ ID NO 147
<211> LENGTH: 121
<212> TYPE: PRT
<213> ORGANISM: Artificial Sequence
<220> FEATURE:
<223> OTHER INFORMATION: Synthetic peptide: SRP1649-B09

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asn Asn
                20                  25                  30

Ala Ile His Trp Val Arg Gln Ala Pro Gly Lys Gly Leu Glu Trp Val
            35                  40                  45

Ala Asp Ile Thr Pro Ala Gly Gly Tyr Thr Gly Tyr Ala Asp Ser Val

```
            50                  55                  60
Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Ile Tyr Arg Met Trp Asp Ser Leu Asp Tyr Trp Gly
                100                 105                 110

Gln Gly Thr Leu Val Thr Val Ser Ser
            115                 120

<210> SEQ ID NO 148
<211> LENGTH: 121
<212> TYPE: PRT
<213> ORGANISM: Artificial Sequence
<220> FEATURE:
<223> OTHER INFORMATION: Synthetic peptide: SRP1497-A05

<400> SEQUENCE: 148

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Ser Asn Tyr
                 20                  25                  30

Ala Ile His Trp Val Arg Gln Ala Pro Gly Lys Gly Leu Glu Trp Val
             35                  40                  45

Ala Asp Ile Thr Pro Asp Gly Gly Tyr Thr Asp Tyr Ala Asp Ser Val
         50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Val Tyr Arg Met Trp Asp Ser Phe Asp Tyr Trp Gly
                100                 105                 110

Gln Gly Thr Leu Val Thr Val Ser Ser
            115                 120

<210> SEQ ID NO 149
<211> LENGTH: 121
<212> TYPE: PRT
<213> ORGANISM: Artificial Sequence
<220> FEATURE:
<223> OTHER INFORMATION: Synthetic peptide: SRP1497-A02

<400> SEQUENCE: 149

Glu Val Gln Leu Val Glu Ser Gly Gly Gly Leu Val Arg Pro Gly Gly
  1               5                  10                  15

Ser Leu Arg Leu Ser Cys Ala Ala Ser Gly Phe Asn Ile Ser Asn Tyr
                 20                  25                  30

Ala Ile His Trp Val Arg Gln Ala Pro Gly Lys Gly Leu Glu Trp Val
             35                  40                  45

Ala Asp Ile Thr Pro Asp Gly Gly Tyr Thr Asp Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Val Tyr Arg Met Trp Asp Ser Phe Asp Tyr Trp Gly
                100                 105                 110
```

```
Gln Gly Thr Leu Val Thr Val Ser Ser
        115                 120
```

<210> SEQ ID NO 150
<211> LENGTH: 121
<212> TYPE: PRT
<213> ORGANISM: Artificial Sequence
<220> FEATURE:
<223> OTHER INFORMATION: Synthetic peptide: SRP1497-A01

<400> SEQUENCE: 150

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
            20                  25                  30

Ala Ile His Trp Val Arg Gln Ala Pro Gly Lys Gly Leu Glu Trp Val
        35                  40                  45

Ala Asp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Val Tyr Arg Met Trp Asp Ser Phe Asp Tyr Trp Gly
            100                 105                 110

Gln Gly Thr Leu Val Thr Val Ser Ser
        115                 120
```

<210> SEQ ID NO 151
<211> LENGTH: 112
<212> TYPE: PRT
<213> ORGANISM: Artificial Sequence
<220> FEATURE:
<223> OTHER INFORMATION: Synthetic peptide: 2D5-VL

<400> SEQUENCE: 151

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Thr
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Glu Leu Glu Ile Lys
            100                 105                 110
```

<210> SEQ ID NO 152
<211> LENGTH: 111
<212> TYPE: PRT
<213> ORGANISM: Artificial Sequence
<220> FEATURE:
<223> OTHER INFORMATION: Synthetic peptide: 22E11-VL

<400> SEQUENCE: 152

```
Asp Ile Val Leu Thr Gln Ser Pro Ala Ser Leu Ala Val Ser Leu Gly
```

```
                1               5                   10                  15
Gln Arg Ala Thr Ile Ser Cys Lys Ala Ser Gln Ser Val Asp Tyr Asp
                20                  25                  30

Gly Asn Ser Tyr Val Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
                100                 105                 110

<210> SEQ ID NO 153
<211> LENGTH: 111
<212> TYPE: PRT
<213> ORGANISM: Artificial Sequence
<220> FEATURE:
<223> OTHER INFORMATION: Synthetic peptide: h22E11-Vk4-1-VL

<400> SEQUENCE: 153

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asn Ser Tyr Val Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Val Glu Ile Lys
                100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Synthetic peptide: h22E11-Vk3-11-VL

<400> SEQUENCE: 154

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asn Ser Tyr Val Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95
```

Glu Asp Pro Tyr Thr Phe Gly Gln Gly Thr Lys Val Glu Ile Lys
              100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Synthetic peptide: h22E11-Vk2-28-VL

<400> SEQUENCE: 155

Asp Ile Val Leu Thr Gln Ser Pro Leu Ser Leu Pro Val Thr Pro Gly
1               5                   10                  15

Glu Pro Ala Ser Ile Ser Cys Lys Ala Ser Gln Ser Val Asp Tyr Asp
            20                  25                  30

Gly Asn Ser Tyr Val Asn Trp Tyr Leu Gln Lys Pro Gly Gln Ser Pro
        35                  40                  45

Gln Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Synthetic peptide: h22E11-Vk1-39-VL

<400> SEQUENCE: 156

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asn Ser Tyr Val Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 157
<211> LENGTH: 111
<212> TYPE: PRT
<213> ORGANISM: Artificial Sequence
<220> FEATURE:
<223> OTHER INFORMATION: Synthetic peptide: h22E11-5-VL

<400> SEQUENCE: 157

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ser Val Asp Tyr Asp

```
                    20                  25                  30

Gly Asn Ser Tyr Val Ala Trp Tyr Gln Gln Lys Pro Gly Gln Ala Pro
                35                  40                  45

Arg Leu Leu Ile Tyr Ala Ala Ser Asn Leu Glu Ser Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Asn
                85                  90                  95

Glu Asp Pro Tyr Thr Phe Gly Gln Gly Thr Lys Val Glu Ile Lys
                100                 105                 110

<210> SEQ ID NO 158
<211> LENGTH: 107
<212> TYPE: PRT
<213> ORGANISM: Artificial Sequence
<220> FEATURE:
<223> OTHER INFORMATION: Synthetic peptide: trastuzumab VL

<400> SEQUENCE: 158

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 159
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 HC Constant

<400> SEQUENCE: 159

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
                 100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 160
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human IgG LC Constant Ckappa

<400> SEQUENCE: 160

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 161
```

```
<211> LENGTH: 323
<212> TYPE: PRT
<213> ORGANISM: Mus musculus
<220> FEATURE:
<221> NAME/KEY: misc_feature
<222> LOCATION: (1)..(323)
<223> OTHER INFORMATION: Mouse IgG1 HC Constant

<400> SEQUENCE: 161
```

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly

```
<210> SEQ ID NO 162
<211> LENGTH: 107
<212> TYPE: PRT
<213> ORGANISM: Mus musculus
<220> FEATURE:
<221> NAME/KEY: misc_feature
```

```
<222> LOCATION: (1)..(107)
<223> OTHER INFORMATION: Mouse IgG LC Constant Ckappa

<400> SEQUENCE: 162

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 163
<211> LENGTH: 108
<212> TYPE: PRT
<213> ORGANISM: Artificial Sequence
<220> FEATURE:
<223> OTHER INFORMATION: Synthetic peptide: Kappa LC

<400> SEQUENCE: 163

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 164
<211> LENGTH: 106
<212> TYPE: PRT
<213> ORGANISM: Artificial Sequence
<220> FEATURE:
<223> OTHER INFORMATION: Synthetic peptide: Lambda LD

<400> SEQUENCE: 164

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 165
<211> LENGTH: 252
<212> TYPE: PRT
<213> ORGANISM: Artificial Sequence
<220> FEATURE:
<223> OTHER INFORMATION: Synthetic peptide: IgG1 Fc from scFv-Fc

<400> SEQUENCE: 165

Ala Ala Gly Ser Asp Gln Glu Pro Lys Ser Ser Asp Lys Thr His Thr
 1               5                  10                  15

Cys Pro Pro Cys Ser Ala Pro Glu Leu Leu Gly Gly Ser Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
 50                  55                  60

Lys Phe Asn Trp Tyr Val Asp Gly Val Glu Val His Asn Ala Lys Thr
 65                  70                  75                  80

Lys Pro Arg Glu Glu Gln Tyr Asn Ser Thr Tyr Arg Val Val Ser Val
                 85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys Gly Ser
225                 230                 235                 240

Gly Asp Tyr Lys Asp Asp Asp Lys Gly Ser Gly
                245                 250

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide: FlagHis Tag

<400> SEQUENCE: 166

Gly Ser Gly Asp Tyr Lys Asp Asp Asp Lys Gly Ser Gly His His
 1               5                  10                  15
```

His His His His
        20

<210> SEQ ID NO 167
<211> LENGTH: 15
<212> TYPE: PRT
<213> ORGANISM: Artificial Sequence
<220> FEATURE:
<223> OTHER INFORMATION: Synthetic peptide: Linker

<400> SEQUENCE: 167

Gly Gly Gly Gly Ser Gly Gly Gly Gly Ser Gly Gly Gly Gly Ser
1               5                   10                  15

<210> SEQ ID NO 168
<211> LENGTH: 11
<212> TYPE: PRT
<213> ORGANISM: Artificial Sequence
<220> FEATURE:
<223> OTHER INFORMATION: Synthetic peptide: Linker

<400> SEQUENCE: 168

Ala Ala Gly Ser Asp Gln Glu Pro Lys Ser Ser
1               5                   10

<210> SEQ ID NO 169
<211> LENGTH: 505
<212> TYPE: PRT
<213> ORGANISM: Artificial Sequence
<220> FEATURE:
<223> OTHER INFORMATION: Synthetic peptide: scFv-Fc

<400> SEQUENCE: 169

Met Glu Val Gln Leu Val Gln Ser Gly Ala Glu Val Lys Lys Pro Gly
1               5                   10                  15

Glu Ser Leu Lys Ile Ser Cys Lys Val Ser Gly Phe Ser Leu Thr Ser
                20                  25                  30

Tyr Gly Val His Trp Val Arg Gln Met Pro Gly Lys Gly Leu Glu Trp
            35                  40                  45

Leu Val Val Ile Trp Ser Asp Gly Ser Thr Thr Tyr Asn Pro Ser Phe
        50                  55                  60

Gln Gly Gln Val Thr Ile Ser Lys Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Gln Gly Gly Tyr Arg Tyr Asp Asp Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Leu Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Ser Val Asp Tyr Asp Gly Asn Ser Tyr Val Asn Trp Tyr
                165                 170                 175

Gln Gln Lys Pro Gly Lys Ala Pro Lys Leu Leu Ile Tyr Ala Ala Ser
            180                 185                 190

Asn Leu Glu Ser Gly Val Pro Ser Arg Phe Ser Gly Ser Gly Ser Gly
        195                 200                 205

```
Thr Asp Phe Thr Leu Thr Ile Ser Ser Leu Gln Pro Glu Asp Phe Ala
            210                 215                 220

Thr Tyr Tyr Cys Gln Gln Ser Asn Glu Asp Pro Tyr Thr Phe Gly Gln
225                 230                 235                 240

Gly Thr Lys Val Glu Ile Lys Ala Ala Gly Ser Asp Gln Glu Pro Lys
                245                 250                 255

Ser Ser Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys Gly Ser Gly Asp Tyr Lys Asp Asp Asp Asp Lys
                485                 490                 495

Gly Ser Gly His His His His His His
            500                 505

<210> SEQ ID NO 170
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: X is Y or H
<220> FEATURE:
<221> NAME/KEY: misc_feature
<222> LOCATION: (3)..(3)
<223> OTHER INFORMATION: X is V or I
<220> FEATURE:
<221> NAME/KEY: misc_feature
<222> LOCATION: (6)..(6)
<223> OTHER INFORMATION: X is M, or L
<220> FEATURE:
<221> NAME/KEY: misc_feature
<222> LOCATION: (10)..(10)
```

```
<223> OTHER INFORMATION: X is Y, F, or L
<220> FEATURE:
<221> NAME/KEY: misc_feature
<222> LOCATION: (12)..(12)
<223> OTHER INFORMATION: X is Y or H

<400> SEQUENCE: 170

Gly Xaa Xaa Tyr Arg Xaa Trp Asp Ser Xaa Asp Xaa
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: X is T, I , S, G, or R
<220> FEATURE:
<221> NAME/KEY: misc_feature
<222> LOCATION: (6)..(6)
<223> OTHER INFORMATION: X is S, R, N, K, or G
<220> FEATURE:
<221> NAME/KEY: misc_feature
<222> LOCATION: (7)..(7)
<223> OTHER INFORMATION: X is N, Y or H

<400> SEQUENCE: 171

Gly Phe Asn Ile Xaa Xaa Xaa
1               5

<210> SEQ ID NO 172
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: X is P, Q, S, or D
<220> FEATURE:
<221> NAME/KEY: misc_feature
<222> LOCATION: (13)..(13)
<223> OTHER INFORMATION: X is S, K, or A
<220> FEATURE:
<221> NAME/KEY: misc_feature
<222> LOCATION: (14)..(14)
<223> OTHER INFORMATION: X is F, L, or V
<220> FEATURE:
<221> NAME/KEY: misc_feature
<222> LOCATION: (15)..(15)
<223> OTHER INFORMATION: X is Q or K
<220> FEATURE:
<221> NAME/KEY: misc_feature
<222> LOCATION: (16)..(16)
<223> OTHER INFORMATION: X is G or S

<400> SEQUENCE: 172

Val Ile Trp Ser Asp Gly Ser Thr Thr Tyr Asn Xaa Xaa Xaa Xaa Xaa
1               5                   10                  15

<210> SEQ ID NO 173
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: X is D, A, or G
<220> FEATURE:
<221> NAME/KEY: misc_feature
<222> LOCATION: (3)..(3)
<223> OTHER INFORMATION: X is T, V, I, S, A, or M
<220> FEATURE:
<221> NAME/KEY: misc_feature
<222> LOCATION: (5)..(5)
<223> OTHER INFORMATION: X is V, G, D, N, T, or A
<220> FEATURE:
<221> NAME/KEY: misc_feature
<222> LOCATION: (6)..(6)
<223> OTHER INFORMATION: X is R, Q, G, A, or V
<220> FEATURE:
<221> NAME/KEY: misc_feature
<222> LOCATION: (8)..(8)
<223> OTHER INFORMATION: X is Y, I , D, S, or F
<220> FEATURE:
<221> NAME/KEY: misc_feature
<222> LOCATION: (10)..(10)
<223> OTHER INFORMATION: X is E, D, or G
<220> FEATURE:
<221> NAME/KEY: misc_feature
<222> LOCATION: (17)..(17)
<223> OTHER INFORMATION: X is G or D

<400> SEQUENCE: 173

Xaa Ile Xaa Pro Xaa Xaa Gly Xaa Thr Xaa Tyr Ala Asp Ser Val Lys
1               5                   10                  15

Xaa

<210> SEQ ID NO 174
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: X is N or A

<400> SEQUENCE: 174

Lys Ala Ser Ser Gln Val Asp Tyr Asp Gly Asn Ser Tyr Val Xaa
1               5                   10                  15

<210> SEQ ID NO 175
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(30)
<223> OTHER INFORMATION: "Gly Gly Gly Gly Ser" may or may not be present

<400> SEQUENCE: 175

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 176
<211> LENGTH: 11
<212> TYPE: PRT
<213> ORGANISM: Artificial Sequence
<220> FEATURE:
<223> OTHER INFORMATION: Synthetic

<400> SEQUENCE: 176
```

```
Arg Ala Ser Gln Asp Val Asn Thr Ala Val Ala
1               5                   10
```

<210> SEQ ID NO 177
<211> LENGTH: 7
<212> TYPE: PRT
<213> ORGANISM: Artificial Sequence
<220> FEATURE:
<223> OTHER INFORMATION: Synthetic

<400> SEQUENCE: 177

```
Ser Ala Ser Phe Leu Tyr Ser
1               5
```

<210> SEQ ID NO 178
<211> LENGTH: 9
<212> TYPE: PRT
<213> ORGANISM: Artificial Sequence
<220> FEATURE:
<223> OTHER INFORMATION: Synthetic

<400> SEQUENCE: 178

```
Gln Gln His Tyr Thr Thr Pro Pro Thr
1               5
```